US007326781B2

(12) United States Patent
Davison et al.

(10) Patent No.: US 7,326,781 B2
(45) Date of Patent: Feb. 5, 2008

(54) POLYNUCLEOTIDES ENCODING THE HUMAN CITRON KINASE POLYPEPTIDE, BMSNKC_0020/0021

(75) Inventors: Daniel B. Davison, Yardley, PA (US); John N. Feder, Belle Mead, NJ (US); Liana M. Lee, Somerset, NJ (US); Karl-Heinz Ott, Mercer, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 254 days.

(21) Appl. No.: 10/412,897

(22) Filed: Apr. 11, 2003

(65) Prior Publication Data

US 2003/0220224 A1 Nov. 27, 2003

Related U.S. Application Data

(60) Provisional application No. 60/372,745, filed on Apr. 12, 2002.

(51) Int. Cl.
*C07H 21/04* (2006.01)
(52) U.S. Cl. ............ 536/23.2; 536/23.5; 536/23.4; 536/23.1; 536/24.31
(58) Field of Classification Search ............. 536/23.2, 536/23.5, 24.31; 435/320.1, 325, 419, 252.3, 435/254.11, 194; 530/387.3
See application file for complete search history.

(56) References Cited

U.S. PATENT DOCUMENTS

| | | | |
|---|---|---|---|
| 5,541,087 A * | 7/1996 | Lo et al. ............... | 435/69.7 |
| 6,479,269 B2 | 11/2002 | Webster et al. | |
| 6,638,745 B1 | 10/2003 | Wei et al. | |
| 6,680,188 B2 | 1/2004 | Webster et al. | |
| 6,692,948 B2 | 2/2004 | Wei et al. | |
| 6,734,009 B2 | 5/2004 | Yu et al. | |
| 6,743,619 B1 * | 6/2004 | Tang et al. ........... | 435/233 |
| 2002/0132322 A1 | 9/2002 | Webster et al. | |
| 2003/0022340 A1 | 1/2003 | Webster et al. | |
| 2003/0153525 A1 | 8/2003 | Silos-Santiago et al. | |
| 2003/0170712 A1 * | 9/2003 | Yan et al. ............. | 435/6 |
| 2004/0038223 A1 | 2/2004 | Smithson et al. | |
| 2004/0091993 A1 | 5/2004 | Webster et al. | |

FOREIGN PATENT DOCUMENTS

| | | |
|---|---|---|
| WO | WO 01/38503 | 5/2001 |
| WO | WO 01/75067 | 10/2001 |
| WO | WO 01/96547 | 12/2001 |
| WO | WO 02/26826 | 4/2002 |
| WO | WO 02/33099 | 4/2002 |
| WO | WO 02/34896 | 5/2002 |
| WO | WO 02/059325 | 8/2002 |
| WO | WO02/099062 A2 | 12/2002 |
| WO | WO 03/004523 | 1/2003 |
| WO | WO 03/004629 | 1/2003 |
| WO | WO/03/012034 A2 | 2/2003 |
| WO | WO 03/029424 | 4/2003 |
| WO | WO03/029424 A2 | 4/2003 |
| WO | WO03/087332 A2 | 10/2003 |
| WO | WO2004/006838 A2 | 1/2004 |
| WO | WO2004/065576 A2 | 8/2004 |

OTHER PUBLICATIONS

Chen et al. (2002) Mol Cell Prot 1:304-313.*
"Encyclopedia of Molecular Biology" Creighton, T.E., John Wiley and Sons, Inc., New York, 1999, p. 632.*
Scott et al. (1999) Nat Genet 21:440-443.*
Brenner (1999) Trends Genet 15:132-133.*
Zuercher et al. (2000) Mech Develop 93:175-177.*
Brosius et al., PNAS 81:6929-6933, 1984.*
New England Biolabs 1996/97 Catalog, p. 147.*
NCBI Entrez Accession No. gi|AC002563, Connell, M. et al., Sep. 26, 1997.
NCBI Entrez Accession No. gi|AF086823, Di Cunto, F. et al., Nov. 11, 1998.
NCBI Entrez Accession No. gi|AF086824, Di Cunto, F. et al., Nov. 11, 1998.
NCBI Entrez Accession No. gi|NP_009105, Liu, H. et al., Oct. 29, 2003.
NCBI Entrez Accession No. gi|3360512, Madaule, P. et al., Jul. 31, 1998.
NCBI Entrez Accession No. gi|30088970, Huang, C.Q. et al., Apr. 23, 2003.
Di Cunto, F. et al., "Citron Rho-interacting Kinase, a Novel Tissue-specific Ser/Thr Kinase Encompassing the Rho-Rac-binding Protein Citron", The Journal of Biological Chemistry, vol. 273, No. 45, pp. 29706-29711 (1998).
Liu, H. et al., "Citron Kinase Is a Cell Cycle-dependent, Nuclear Protein Required for $G_2$/M Transition of Hepatocytes", The Journal of Biological Chemistry, vol. 278, No. 4, pp. 2541-2548 (2003).
Daigle, et al., "Aminoglycoside antibiotic phosphotransferases are also serine protein kinases", Chem. Biol., vol. 6(1), pp. 11-18 (1999).
Dancey, et al., "Issues and Progress with Protein Kinase Inhibitors for Cancer Treatment", Nature, vol. 2, pp. 296-313 (2003).
DiCunto, et al., "Defective Neurogenesis in Citron Kinase Knock-out Mice by Altered Cytokinesis and Massive Apoptosis", Neuron, vol. 28, pp. 115-127 (2000).

(Continued)

*Primary Examiner*—David J. Steadman
(74) *Attorney, Agent, or Firm*—Stephen C. D'Amico

(57) ABSTRACT

The present invention describes a novel human protein kinase related to citron kinase, and its encoding polynucleotide. Also described are expression vectors, host cells, antisense molecules, and antibodies associated with the protein kinase polynucleotide and/or polypeptide of this invention. In addition, methods for treating, diagnosing, preventing, and screening for disorders or diseases associated with abnormal biological activity of the protein kinase are described, as are methods for screening for modulators, e.g., agonists or antagonists, of the protein kinase activity and/or function.

5 Claims, 18 Drawing Sheets

OTHER PUBLICATIONS

Döbeli, et al., "Role of carboxy-terminal sequence on the biological activity of human immune interferon (IFN-γ)", J Biotech., vol. 7, pp. 199-216 (1988).
Drier, et al., "Nuclear import of the *Drosophila* Rel protein Dorsal is regulated by phosphorylation", Genes Develop., vol. 13, pp. 556-568 (1999).
Falquet, et al., "The Prosite databasse, its status in 2002", Nucleic Acids Res., vol. 30(1), pp. 235-238 (2002).
Fry, et al., "The NIMA Kinase Joins Forces with Cdc2", Curr. Biol., vol. 5(10), pp. 1122-1125 (1995).
Gayle, et al., "Identification of Regions in Interleukin-1α Important for Activity", JBC, vol. 268(29), pp. 22105-22111 (1993).
Ghosh, et al., "Cdc2-Independent Induction of Premature Mitosis by Okadaic Acid in HeLa Cells", Exp. Cell Res., vol. 242, pp. 1-9 (1998).
Gilman, A.G., "A Protein Binding Assay for Adenosine 3':5'-Cyclic Monophosphate", PNAS, vol. 67(1), pp. 306-312 (1970).
Krien, et al., "A NIMA homologue promotes chromatin condensation in fission yeast", J Cell Science, vol. 111, pp. 967-976 (1998).
Lu, et al., "The NIMA kinase: A mitotic regulator in *Aspergillus nidulans* and vertebrate cells", Prog. Cell. Cycle Res., vol. 1, pp. 187-205 (1995).
Lu, et al., "A human peptidyl-prolyl isomerase essential for regulation of mitosis", Nature, vol. 380, pp. 544-547 (1996).
Lu, et al., "Function of WW Domains as Phosphoserine- or Phosphothreonine-Binding Modules", Science, vol. 283, pp. 1325-1328 (1999).
Madaule, et al., "A novel partner for the GTP-bound forms of *rho* and *rac*", Febs Let., vol. 377, pp. 243-248 (1995).
Morrison, et al., "The complexity of Raf-I regulation", Curr. Opin. Cell Biol., vol. 9, pp. 174-179 (1997).
Navas, et al., "RIP2 Is a Raf1-activated Mitogen-activated Protein Kinase Kinase", JBC, vol. 274(47), pp. 33684-33690 (1999).
Ron, et al., "Expression of Biologically Active Recombinant Keratinocyte Growth Factor", JBC, vol. 268(4), pp. 2984-2988 (1993).
Plowman, et al., "The protein kinases of Caenorhabditis elegans: A model for signal transduction in multicellular organisms", PNAS, vol. 96(24), pp. 13603-13610 (1999).
Ronco, et al., "Identification of Conserved Amino Acids in the Human Granulocyte-Macrophage Colony-stimulating Factor Receptor α Subunit Critical for Function", JBC, vol. 269(1), pp. 277-283 (1994).
Silljé, et al., "Mammalian homologues of the plant *Tousled* gene code for cell-cycle-regulated kinases with maximal activities linked to ongoing DNA replication", EMBO J., vol. 18(20), pp. 5691-5702 (1999).
Songyang, et al., "A Structural Basis for Substrate Specificities of Protein Ser/Thr Kinases: Primary Sequence Preference of Casein Kinases I and II, NIMA, Phosphorylase Kinase, Calmodulin-Dependent Kinase II, CDK5, and Erk1", Molec. Cell. Biol., vol. 16(11), pp. 6486-6493 (1996).
Aelst, et al., "Rho GTPases and signaling networks", Genes Develop., vol. 11, pp. 2295-2322 (1997).
NCBI Entrez Accession No. AAC27933 (gi:3360514), Madaule, et al., Jul. 31, 1998.
NCBI Entrez Accession No. AAC72822 (gi:3599507), DiCunto, et al., Nov. 10, 1998.
NCBI Entrez Accession No. AAN98600 (gi:27302422), Webster, et al., Dec. 20, 2002.
NCBI Entrez Accession No. AAP43922 (gi:37784567), Mao, et al., Feb. 1, 2004.
NCBI Entrez Accession No. AAR68726 (gi:40164454), Wei, et al., Dec. 18, 2003.
NCBI Entrez Accession No. AAR68728 (gi:40164456), Wei, et al., Dec. 18, 2003.
NCBI Entrez Accession No. AAR68729 (gi:40164457), Wei, et al., Dec. 18, 2003.
NCBI Entrez Accession No. AAS30451 (gi:42686146), Webster, et al., Feb. 20, 2004.
NCBI Entrez Accession No. AAS37164 (gi:42714912), Wei, et al., Feb. 20, 2004.
NCBI Entrez Accession No. AAS37165 (gi:42714913), Wei, et al., Feb. 20, 2004.
NCBI Entrez Accession No. AAS37166 (gi:42714914), Wei, et al., Feb. 20, 2004.
NCBI Entrez Accession No. AB023166 (gi:58257671), Nagase, et al., Jan. 28, 2005.
NCBI Entrez Accession No. AC004813 (gi:4926912), Waterson, R.H., May 29,1999.
NCBI Entrez Accession No. AC004815 (gi:5836220), Waterson, R.H., Sep. 8, 1999.
NCBI Entrez Accession No. AC026363 (gi:19718575), Muzny, et al., Mar. 26, 2002.
NCBI Entrez Accession No. AC079317 (gi:19807685), Muzny, et al., Apr. 2, 2002.
NCBI Entrez Accession No. AC079455 (gi:21591798), Muzny, et al., Sep. 3, 2002.
NCBI Entrez Accession No. AF070065 (gi:3360511), Madaule, et al., Jul. 31, 1998.
NCBI Entrez Accession No. AF070066 (gi:3360513), Madaule, et al., Jul. 31, 1998.
NCBI Entrez Accession No. NM_007174 (gi:32698687), Liu, et al., Apr. 23, 2005.
NCBI Entrez Accession No. NP_009105 (gi:32698688), Liu, et al., Apr. 23, 2005.
NCBI Entrez Accession No. NP_009195 (gi:6005705), Xu, et al., Apr. 23, 2005.
NCBI Entrez Accession No. O14578 (gi:6225217), Connell, et al., Jun. 15, 2002.
NCBI Entrez Accession No. O14578 (gi:57015279), Huang, et al., May 1. 2005.
NCBI Entrez Accession No. P49025 (gi:57015300) Madaule, et al., May 1, 2005.
NCBI Entrez Accession No. XP_132275 (gi:20841360), NCBI Annotation Project, Feb. 24, 2003.
NCBI Entrez Accession No. XP_213796 (gi:34872621), NCBI Annotation Project, Oct. 23, 2003.
NCBI Entrez Accession No. XP_213796 (gi:27666020), NCBI Annotation Project, Jan. 28, 2003.
NCBI Entrez Accession No. XP_509420 (gi:55639043), NCBI Annotation Project, Nov. 9, 2004.
NCBI Entrez Accession No. XP_543422 (gi:57105894), NCBI Annotation Project, Jan. 4, 2005.
NCBI Entrez Accession No. AAS37167 (gi:42714915), Wei, et al., Feb. 20, 2004.
Eda, et al., "Rho-dependent transfer of Citron-kinase to the cleavage furrow of dividing cells", J. Cell Science, vol. 114, pp. 3273-3284 (2001).
Madaule, et al., "Role of citron kinase as a target of the small GTPase Rho in cytokinesis", Nature, vol. 394, pp. 491-494 (1998).

* cited by examiner

FIG. 1

```
  1  ATGTTGAAGTTCAAATATGGAGCGCGGAATCCTTTGGATGCTGGTGCTGCTGAACCCATT    60
  1   M  L  K  F  K  Y  G  A  R  N  P  L  D  A  G  A  A  E  P  I    20

61  GCCAGCCGGGCCTCCAGGCTGAATCTGTTCTTCCAGGGGAAACCACCCTTTATGACTCAA   120
 21   A  S  R  A  S  R  L  N  L  F  F  Q  G  K  P  P  F  M  T  Q    40

121  CAGCAGATGTCTCCTCTTTCCCGAGAAGGGATATTAGATGCCCTCTTTGTTCTCTTTGAA   180
 41   Q  Q  M  S  P  L  S  R  E  G  I  L  D  A  L  F  V  L  F  E    60

181  GAATGCAGTCAGCCTGCTCTGATGAAGATTAAGCACGTGAGCAACTTTGTCCGGAAGTAT   240
 61   E  C  S  Q  P  A  L  M  K  I  K  H  V  S  N  F  V  R  K  Y    80

241  TCCGACACCATAGCTGAGTTACAGGAGCTCCAGCCTTCGGCAAAGGACTTCGAAGTCAGA   300
 81   S  D  T  I  A  E  L  Q  E  L  Q  P  S  A  K  D  F  E  V  R   100

301  AGTCTTGTAGGTTGTGGTCACTTTGCTGAAGTGCAGGTGGTAAGAGAGAAAGCAACCGGG   360
101   S  L  V  G  C  G  H  F  A  E  V  Q  V  V  R  E  K  A  T  G   120

361  GACATCTATGCTATGAAAGTGATGAAGAAGAAGGCTTTATTGGCCCAGGAGCAGGTTTCA   420
121   D  I  Y  A  M  K  V  M  K  K  K  A  L  L  A  Q  E  Q  V  S   140

421  TTTTTTGAGGAAGAGCGGAACATATTATCTCGAAGCACAAGCCCGTGGATCCCCCAATTA   480
141   F  F  E  E  E  R  N  I  L  S  R  S  T  S  P  W  I  P  Q  L   160

481  CAGTATGCCTTTCAGGACAAAAATCACCTTTATCTGGTCATGGAATATCAGCCTGGAGGG   540
161   Q  Y  A  F  Q  D  K  N  H  L  Y  L  V  M  E  Y  Q  P  G  G   180

541  GACTTGCTGTCACTTTTGAATAGATATGAGGACCAGTTAGATGAAAACCTGATACAGTTT   600
181   D  L  L  S  L  L  N  R  Y  E  D  Q  L  D  E  N  L  I  Q  F   200

601  TACCTAGCTGAGCTGATTTTGGCTGTTCACAGCGTTCATCTGATGGGATACGTGCATCGA   660
201   Y  L  A  E  L  I  L  A  V  H  S  V  H  L  M  G  Y  V  H  R   220

661  GACATCAAGCCTGAGAACATTCTCGTTGACCGCACAGGACACATCAAGCTGGTGGATTTT   720
221   D  I  K  P  E  N  I  L  V  D  R  T  G  H  I  K  L  V  D  F   240

721  GGATCTGCCGCGAAAATGAATTCAAACAAGATGGTGAATGCCAAACTCCCGATTGGGACC   780
241   G  S  A  A  K  M  N  S  N  K  M  V  N  A  K  L  P  I  G  T   260

781  CCAGATTACATGGCTCCTGAAGTGCTGACTGTGATGAACGGGGATGGAAAAGGCACCTAC   840
261   P  D  Y  M  A  P  E  V  L  T  V  M  N  G  D  G  K  G  T  Y   280

841  GGCCTGGACTGTGACTGGTGGTCAGTGGGCGTGATTGCCTATGAGATGATTTATGGGAGA   900
281   G  L  D  C  D  W  W  S  V  G  V  I  A  Y  E  M  I  Y  G  R   300

901  TCCCCCTTCGCAGAGGGAACCTCTGCCAGAACCTTCAATAACATTATGAATTTCCAG    957
301   S  P  F  A  E  G  T  S  A  R  T  F  N  N  I  M  N  F  Q    319
```

FIG. 2

```
  1 YQTIKIIGKGAFGEVKLVQKKADGKVYAMKSLIKTEMFKKDQLAHVRAER  50
    ::   ::| | | ||..|..|| |  :||||  :  |   :  |  .    ||
  1 FEVRSLVGCGHFAEVQVVREKATGDIYAMKVMKKKALLAQEQ.SFFEEER  49

51 DILAESDSPWVVKLYTTFQDANFLYMLMEFLPGGDLMTMLIKYE.IFSED  99
    .||. | |||: .|   ||| | || |||: ||||:..| :||    |.
 50 NILSRSTSPWIPQLQYAFQDKNHLY.LMEYQPGGDLLSLLNRYEDQLDEN  98

100 ITRFYIAEIVLAIDAVHKLGFIHRDIKPDNILLDRGGHVKLTDFGLSTGF 149
    : .||:||::||: .|| :|::||||||:|||.|| ||:|| |||  .
 99 LIQFYLAELILAVHSVHLMGYVHRDIKPENILVDRTGHIKLVDFGSAA.. 146

150 HKLHDNNYYTQLLQGKSMAYSTVGTPDYIAPEIFT.....GHG.YSFDCD 193
    |:. |        | |  :|||||.|||: |     | |  |||
147 .KMNSN........KMNAKLPIGTPDYMAPEVLTVMNGDGKGTYGLDCD 186

194 WWSLGTIMFECLVGWPPFCAEDSHDTYRKIVNWRHSLYFPDDITLGVDAE 243
    |||.| | :| : | ||    | |: |.|..
187 WWSVGVIAYEMIYGRSPFAEGTSARTFNNIMNFQ................ 220
```

FIG. 3A

```
citronkina  ---------- ---------- ---------- ---------- ----------
cot1        ---------- ---------- ---------- ---------- ----------
Mus         PFVPTLKSDD DTSNFDEPEK NSWVSSSVCQ LSPSGFSGEE LPFVGFSYSK citronkina  ---------- ---------- ---------- ---------- ----------
cot1        ---------- ---------- ---------- ---------- ----------
Mus         ALGYLGRSES VVSSLDSPAK VSSMEKKLLI KSKELQDSQD KCHKMEQEMT citronkina  ---------- --------ML KFKYGARNPL DAGAAEPIAS RASRLNLFFQ
cot1        ---------- ---------- ---------- ---------- ----------
Mus         RLHRRVSEVE AVLSQKEVEL KASETQRSLL EQDLATYITE CSSLKRSLEQ citronkina  GKPPFMTQQQ MSPLSREGIL DALFVLFEEC SQPALMKIKH VSNFVRKYSD
cot1        ---------- ---------- ---------- ---------- ----------
Mus         ARMEVSQEDD KALQLLHDIR EQSRKLQEIK EQEYQAQVEE MRLMMNQLEE citronkina  TIAELQ---- ----ELQPSA KDFEVRSLVG CGHFAEVQVV REKATGDIYA
cot1        ---------- ---------- --YQTIKIIG KGAFGEVKLV QKKADGKVYA
Mus         DLVSARRRSD LYESELRESR LAAEEFKRKA NECQHKLMKA KDQGKPEVGE citronkina  MKVMKKKALL AQEQVSFFEE ERNILSRSTS PWIPQLQYAF QDKNHLYLVM
cot1        MKSLIKTEMF KKDQLAHVRA ERDILAESDS PWVVKLYTTF QDANFLYMLM
Mus         YSKLEKINAE QQLKIQELQE KLEKAVKAST EATELLQNIR QAKERAEREL citronkina  EYQPGGDLLS LLNRYEDQLD ENLIQFYLAE LILAVHSVHL MGYVHRDIKP
cot1        EFLPGGDLMT MLIKYE-IFS EDITRFYIAE IVLAIDAVHK LGFIHRDIKP
Mus         EKLHNREDSS EGIKKKLVEA EELEEKHREA QVSAQHLEVH LKQKEQHYEE citronkina  ENILVDRTGH IKLVDFGSAA ---KMNSNKM VNAKLP---- ----IGTPDY
cot1        DNILLDRGGH VKLTDFGLST GFHKLHDNNY YTQLLQGKSM AYSTVGTPDY
Mus         KIKVLDNQIK KDLADKESLE NMMQRHEEEA HEKGKILSEQ ----KAMINA citronkina  MAPEVLTVMN GDGKGTYGLD CDWWSVGVIA YEMIYGRSPF AEGTSARTFN
cot1        IAPEIFTGHG ------YSFD CDWWSLGTIM FECLVGWPPF CAEDSHDTYR
Mus         MDSKIRSLEQ RIVELSEANK LAANSSLFTQ RNMKAQEEMI SELRQQKFYL citronkina  NIMNFQ---- ---------- ---------- ---------- ----------
cot1        KIVNWRHSLY FPDDITLGVD AENLIRSLIC NTENRLGRGG AHEIKSHAFF
Mus         ETQAGKLEAQ NRKLEEQLEK ISHQDHSDKS RLLELETRLR EVSLEHEEQK citronkina  ---------- ---------- ---------- ---------- ----------
cot1        ---------- ---------- ---------- ---------- ----------
Mus         LELKRQLTEL QLSLQERESQ LTALQAARAA LESQLRQAKT ELEETTAEAE citronkina  ---------- ---------- ---------- ---------- ----------
cot1        ---------- ---------- ---------- ---------- ----------
Mus         EEIQALTAHR DEIQRKFDAL RNSCTVITDL EEQLNQLTED NAELNNQNFY citronkina  ---------- ---------- ---------- ---------- ----------
cot1        ---------- ---------- ---------- ---------- ----------
Mus         LSKQLDEASG ANDEIVQLRS EVDHLRREIT EREMQLTSQK QTMEALKTTC citronkina  ---------- ---------- ---------- ---------- ----------
cot1        ---------- ---------- ---------- ---------- ----------
Mus         TMLEFQVLDL EALNDELLEK ERQWEAWRSV LGDEKSQFEC RVRELQRMLD
```

FIG. 3B

```
citronkina  ----------  ----------  ----------  ----------  ----------
cot1        ----------  ----------  ----------  ----------  ----------
Mus         TEKQSRARAD  QRITESRQVV  ELAVKEHKAE  ILALQQALKE  QKLKAESLSD citronkina  ----------  ----------  ----------  ----------  ----------
cot1        ----------  ----------  ----------  ----------  ----------
Mus         KLNDLEKKHA  MLEMNARSLQ  QKLETERELK  QRLLEEQAKL  QQQMDLQKNH citronkina  ----------  ----------  ----------  ----------  ----------
cot1        ----------  ----------  ----------  ----------  ----------
Mus         IFRLTQGLQE  ALDRADLLKT  ERSDLEYQLE  NIQVLYSHEK  VKMEGTISQQ citronkina  ----------  ----------  ----------  ----------  ----------
cot1        ----------  ----------  ----------  ----------  ----------
Mus         TKLIDFLQAK  MDQPAKKKKV  PLQYNELKLA  LEKEKARCAE  LEEALQKTRI citronkina  ----------  ----------  ----------  ----------  ----------
cot1        ----------  ----------  ----------  ----------  ----------
Mus         ELRSAREEAA  HRKATDHPHP  STPATARQQI  AMSAIVRSPE  HQPSAMSLLA citronkina  ----------  ----------  ----------  ----------  ----------
cot1        ----------  ----------  ----------  ----------  ----------
Mus         PPSSRRKESS  TPEEFSRRLK  ERMHHNIPHR  FNVGLNMRAT  KCAVCLDTVH citronkina  ----------  ----------  ----------  ----------  ----------
cot1        ----------  ----------  ----------  ----------  ----------
Mus         FGRQASKCLE  CQVMCHPKCS  TCLPATCGLP  AEYATHFTEA  FCRDKMNSPG citronkina  ----------  ----------  ----------  ----------  ----------
cot1        ----------  ----------  ----------  ----------  ----------
Mus         LQSKEPGSSL  HLEGWMKVPR  NNKRGQQGWD  RKYIVLEGSK  VLIYDNEARE citronkina  ----------  ----------  ----------  ----------  ----------
cot1        ----------  ----------  ----------  ----------  ----------
Mus         AGQRPVEEFE  LCLPDGDVSI  HGAVGASELA  NTAKADVPYI  LKMESHPHTT citronkina  ----------  ----------  ----------  ----------  ----------
cot1        ----------  ----------  ----------  ----------  ----------
Mus         CWPGRTLYLL  APSFPDKQRW  VTALESVVAG  GRVSREKAEA  DAKLLGNSLL citronkina  ----------  ----------  ----------  ----------  ----------
cot1        ----------  ----------  ----------  ----------  ----------
Mus         KLEGDDRLDM  NCTLPFSDQV  VLVGTEEGLY  ALNVLKNSLT  HIPGIGAVFQ citronkina  ----------  ----------  ----------  ----------  ----------
cot1        ----------  ----------  ----------  ----------  ----------
Mus         IYIIKDLEKL  LMIAGEERAL  CLVDVKKVKQ  SLAQSHLPAQ  PDVSPNIFEA citronkina  ----------  ----------  ----------  ----------  ----------
cot1        ----------  ----------  ----------  ----------  ----------
Mus         VKGCHLFAAG  KIENSLCICA  AMPSKVVILR  YNDNLSKYCI  RKEIETSEPC citronkina  ----------  ----------  ----------  ----------  ----------
cot1        ----------  ----------  ----------  ----------  ----------
Mus         SCIHFTNYST  LIGTNKFYEI  DMKQYTLDEF  LDKNDHSLAP  AVFASSSNSF
```

FIG. 3C

```
citronkina  ---------- ---------- ---------- ---------- ----------
cot1        ---------- ---------- ---------- ---------- ----------
Mus         PVSIVQANSA GQREEYLLCF HEFGVFVDSY GRRSRTDDLK WSRLPLAFAY citronkina  ---------- ---------- ---------- ---------- ----------
cot1        ---------- ---------- ---------- ---------- ----------
Mus         REPYLFVTHF NSLEVIEIQA RSSLGSPARA YLEIPNPRYL GPAISSGAIY citronkina  ---------- ---------- ---------- ---------- ----------
cot1        ---------- ---------- ---------- ---------- ----------
Mus         LASSYQDKLR VICCKGNLVK ESGTEQHRVP STSRSSPNKR GPPTYNEHIT citronkina  ---------- ---------- ---------- ---------- ----------
cot1        ---------- ---------- ---------- ---------- ----------
Mus         KRVASSPAPP EGPSHPREPS TPHRYRDREG RTELRRDKSP GRPLEREKSP citronkina  ---------- ---------- ---------- ---------- -----
cot1        ---------- ---------- ---------- ---------- -----
Mus         GRMLSTRRER SPGRLFEDSS RGRLPAGAVR TPLSQVNKVW DQSSV
```

SEQUENCE LISTING

```
<160> NUMBER OF SEQ ID NOS: 77

<210> SEQ ID NO 1
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 1 atg ttg aag ttc aaa tat gga gcg cgg aat cct ttg gat gct ggt gct      48
Met Leu Lys Phe Lys Tyr Gly Ala Arg Asn Pro Leu Asp Ala Gly Ala
1               5                  10                  15 gct gaa ccc att gcc agc cgg gcc tcc agg ctg aat ctg ttc ttc cag      96
Ala Glu Pro Ile Ala Ser Arg Ala Ser Arg Leu Asn Leu Phe Phe Gln
            20                  25                  30 ggg aaa cca ccc ttt atg act caa cag cag atg tct cct ctt tcc cga     144
Gly Lys Pro Pro Phe Met Thr Gln Gln Gln Met Ser Pro Leu Ser Arg
        35                  40                  45 gaa ggg ata tta gat gcc ctc ttt gtt ctc ttt gaa gaa tgc agt cag     192
Glu Gly Ile Leu Asp Ala Leu Phe Val Leu Phe Glu Glu Cys Ser Gln
    50                  55                  60 cct gct ctg atg aag att aag cac gtg agc aac ttt gtc cgg aag tat     240
Pro Ala Leu Met Lys Ile Lys His Val Ser Asn Phe Val Arg Lys Tyr
65                  70                  75                  80 tcc gac acc ata gct gag tta cag gag ctc cag cct tcg gca aag gac     288
Ser Asp Thr Ile Ala Glu Leu Gln Glu Leu Gln Pro Ser Ala Lys Asp
                85                  90                  95 ttc gaa gtc aga agt ctt gta ggt tgt ggt cac ttt gct gaa gtg cag     336
Phe Glu Val Arg Ser Leu Val Gly Cys Gly His Phe Ala Glu Val Gln
            100                 105                 110 gtg gta aga gag aaa gca acc ggg gac atc tat gct atg aaa gtg atg     384
Val Val Arg Glu Lys Ala Thr Gly Asp Ile Tyr Ala Met Lys Val Met
        115                 120                 125 aag aag aag gct tta ttg gcc cag gag cag gtt tca ttt ttt gag gaa     432
Lys Lys Lys Ala Leu Leu Ala Gln Glu Gln Val Ser Phe Phe Glu Glu
    130                 135                 140 gag cgg aac ata tta tct cga agc aca agc ccg tgg atc ccc caa tta     480
Glu Arg Asn Ile Leu Ser Arg Ser Thr Ser Pro Trp Ile Pro Gln Leu
145                 150                 155                 160
```

-continued

| | | |
|---|---|---|
| cag tat gcc ttt cag gac aaa aat cac ctt tat ctg gtc atg gaa tat<br>Gln Tyr Ala Phe Gln Asp Lys Asn His Leu Tyr Leu Val Met Glu Tyr<br>                      165                  170                175 | | 528 |
| cag cct gga ggg gac ttg ctg tca ctt ttg aat aga tat gag gac cag<br>Gln Pro Gly Gly Asp Leu Leu Ser Leu Leu Asn Arg Tyr Glu Asp Gln<br>        180                      185                  190 | | 576 |
| tta gat gaa aac ctg ata cag ttt tac cta gct gag ctg att ttg gct<br>Leu Asp Glu Asn Leu Ile Gln Phe Tyr Leu Ala Glu Leu Ile Leu Ala<br>            195                    200                  205 | | 624 |
| gtt cac agc gtt cat ctg atg gga tac gtg cat cga gac atc aag cct<br>Val His Ser Val His Leu Met Gly Tyr Val His Arg Asp Ile Lys Pro<br>      210                    215                    220 | | 672 |
| gag aac att ctc gtt gac cgc aca gga cac atc aag ctg gtg gat ttt<br>Glu Asn Ile Leu Val Asp Arg Thr Gly His Ile Lys Leu Val Asp Phe<br>225                      230                    235                240 | | 720 |
| gga tct gcc gcg aaa atg aat tca aac aag atg gtg aat gcc aaa ctc<br>Gly Ser Ala Ala Lys Met Asn Ser Asn Lys Met Val Asn Ala Lys Leu<br>                      245                  250                255 | | 768 |
| ccg att ggg acc cca gat tac atg gct cct gaa gtg ctg act gtg atg<br>Pro Ile Gly Thr Pro Asp Tyr Met Ala Pro Glu Val Leu Thr Val Met<br>        260                      265                  270 | | 816 |
| aac ggg gat gga aaa ggc acc tac ggc ctg gac tgt gac tgg tgg tca<br>Asn Gly Asp Gly Lys Gly Thr Tyr Gly Leu Asp Cys Asp Trp Trp Ser<br>            275                    280                  285 | | 864 |
| gtg ggc gtg att gcc tat gag atg att tat ggg aga tcc ccc ttc gca<br>Val Gly Val Ile Ala Tyr Glu Met Ile Tyr Gly Arg Ser Pro Phe Ala<br>      290                    295                    300 | | 912 |
| gag gga acc tct gcc aga acc ttc aat aac att atg aat ttc cag<br>Glu Gly Thr Ser Ala Arg Thr Phe Asn Asn Ile Met Asn Phe Gln<br>305                      310                    315 | | 957 |

<210> SEQ ID NO 2
<211> LENGTH: 319
<212> TYPE: PRT
<213> ORGANISM: Homo sapiens

<400> SEQUENCE: 2

Met Leu Lys Phe Lys Tyr Gly Ala Arg Asn Pro Leu Asp Ala Gly Ala
1               5                   10                  15

Ala Glu Pro Ile Ala Ser Arg Ala Ser Arg Leu Asn Leu Phe Phe Gln
            20                  25                  30

Gly Lys Pro Pro Phe Met Thr Gln Gln Met Ser Pro Leu Ser Arg
        35                  40                  45

Glu Gly Ile Leu Asp Ala Leu Phe Val Leu Phe Glu Glu Cys Ser Gln
    50                  55                  60

Pro Ala Leu Met Lys Ile Lys His Val Ser Asn Phe Val Arg Lys Tyr
65                  70                  75                  80

Ser Asp Thr Ile Ala Glu Leu Gln Glu Leu Gln Pro Ser Ala Lys Asp
                85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
            115                 120                 125

Lys Lys Lys Ala Leu Leu Ala Gln Glu Gln Val Ser Phe Phe Glu Glu
        130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr

```
                 165                 170                 175
Gln Pro Gly Gly Asp Leu Leu Ser Leu Leu Asn Arg Tyr Glu Asp Gln
            180                 185                 190

Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
    210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Met Val Asn Ala Lys Leu
                245                 250                 255

Pro Ile Gly Thr Pro Asp Tyr Met Ala Pro Glu Val Leu Thr Val Met
            260                 265                 270

Asn Gly Asp Gly Lys Gly Thr Tyr Gly Leu Asp Cys Asp Trp Trp Ser
        275                 280                 285

Val Gly Val Ile Ala Tyr Glu Met Ile Tyr Gly Arg Ser Pro Phe Ala
    290                 295                 300

Glu Gly Thr Ser Ala Arg Thr Phe Asn Asn Ile Met Asn Phe Gln
305                 310                 315

<210> SEQ ID NO 3
<211> LENGTH: 1441
<212> TYPE: PRT
<213> ORGANISM: Homo sapiens

<400> SEQUENCE: 3

Asp Leu Val Ser Ala Arg Arg Ser Asp Leu Tyr Glu Ser Glu Leu
1               5                   10                  15

Arg Glu Ser Arg Leu Ala Ala Glu Glu Phe Lys Arg Lys Ala Asn Glu
            20                  25                  30

Cys Gln His Lys Leu Met Lys Ala Lys Asp Gln Gly Lys Pro Glu Val
        35                  40                  45

Gly Glu Tyr Ser Lys Leu Glu Lys Ile Asn Ala Glu Gln Gln Leu Lys
    50                  55                  60

Ile Gln Glu Leu Gln Glu Lys Leu Glu Lys Ala Val Lys Ala Ser Thr
65                  70                  75                  80

Glu Ala Thr Glu Leu Leu Gln Asn Ile Arg Gln Ala Lys Glu Arg Ala
                85                  90                  95

Glu Arg Glu Leu Glu Lys Leu His Asn Arg Glu Asp Ser Ser Glu Gly
            100                 105                 110

Ile Lys Lys Lys Leu Val Glu Ala Glu Glu Leu Glu Glu Lys His Arg
        115                 120                 125

Glu Ala Gln Val Ser Ala Gln His Leu Glu Val His Leu Lys Gln Lys
    130                 135                 140

Glu Gln His Tyr Glu Glu Lys Ile Lys Val Leu Asp Asn Gln Ile Lys
145                 150                 155                 160

Lys Asp Leu Ala Asp Lys Glu Ser Leu Glu Asn Met Met Gln Arg His
                165                 170                 175

Glu Glu Glu Ala His Glu Lys Gly Lys Ile Leu Ser Glu Gln Lys Ala
            180                 185                 190

Met Ile Asn Ala Met Asp Ser Lys Ile Arg Ser Leu Glu Gln Arg Ile
        195                 200                 205

Val Glu Leu Ser Glu Ala Asn Lys Leu Ala Ala Asn Ser Ser Leu Phe
    210                 215                 220
```

```
Thr Gln Arg Asn Met Lys Ala Gln Glu Glu Met Ile Ser Glu Leu Arg
225                 230                 235                 240

Gln Gln Lys Phe Tyr Leu Glu Thr Gln Ala Gly Lys Leu Glu Ala Gln
                245                 250                 255

Asn Arg Lys Leu Glu Glu Gln Leu Glu Lys Ile Ser His Gln Asp His
                260                 265                 270

Ser Asp Lys Ser Arg Leu Leu Glu Leu Glu Thr Arg Leu Arg Glu Val
            275                 280                 285

Ser Leu Glu His Glu Glu Gln Lys Leu Glu Leu Lys Arg Gln Leu Thr
    290                 295                 300

Glu Leu Gln Leu Ser Leu Gln Glu Arg Glu Ser Gln Leu Thr Ala Leu
305                 310                 315                 320

Gln Ala Ala Arg Ala Ala Leu Glu Ser Gln Leu Arg Gln Ala Lys Thr
                325                 330                 335

Glu Leu Glu Glu Thr Thr Ala Glu Ala Glu Glu Ile Gln Ala Leu
                340                 345                 350

Thr Ala His Arg Asp Glu Ile Gln Arg Lys Phe Asp Ala Leu Arg Asn
            355                 360                 365

Ser Cys Thr Val Ile Thr Asp Leu Glu Glu Gln Leu Asn Gln Leu Thr
    370                 375                 380

Glu Asp Asn Ala Glu Leu Asn Asn Gln Asn Phe Tyr Leu Ser Lys Gln
385                 390                 395                 400

Leu Asp Glu Ala Ser Gly Ala Asn Asp Glu Ile Val Gln Leu Arg Ser
                405                 410                 415

Glu Val Asp His Leu Arg Arg Glu Ile Thr Glu Arg Glu Met Gln Leu
                420                 425                 430

Thr Ser Gln Lys Gln Thr Met Glu Ala Leu Lys Thr Thr Cys Thr Met
            435                 440                 445

Leu Glu Glu Gln Val Leu Asp Leu Glu Ala Leu Asn Asp Glu Leu Leu
450                 455                 460

Glu Lys Glu Arg Gln Trp Glu Ala Trp Arg Ser Val Leu Gly Asp Glu
465                 470                 475                 480

Lys Ser Gln Phe Glu Cys Arg Val Arg Glu Leu Gln Arg Met Leu Asp
                485                 490                 495

Thr Glu Lys Gln Ser Arg Ala Arg Ala Asp Gln Arg Ile Thr Glu Ser
            500                 505                 510

Arg Gln Val Val Glu Leu Ala Val Lys Glu His Lys Ala Glu Ile Leu
    515                 520                 525

Ala Leu Gln Gln Ala Leu Lys Glu Gln Lys Leu Lys Ala Glu Ser Leu
    530                 535                 540

Ser Asp Lys Leu Asn Asp Leu Glu Lys Lys His Ala Met Leu Glu Met
545                 550                 555                 560

Asn Ala Arg Ser Leu Gln Gln Lys Leu Glu Thr Glu Arg Glu Leu Lys
                565                 570                 575

Gln Arg Leu Leu Glu Glu Gln Ala Lys Leu Gln Gln Met Asp Leu
                580                 585                 590

Gln Lys Asn His Ile Phe Arg Leu Thr Gln Gly Leu Gln Glu Ala Leu
            595                 600                 605

Asp Arg Ala Asp Leu Leu Lys Thr Glu Arg Ser Asp Leu Glu Tyr Gln
    610                 615                 620

Leu Glu Asn Ile Gln Val Leu Tyr Ser His Glu Lys Val Lys Met Glu
625                 630                 635                 640

Gly Thr Ile Ser Gln Gln Thr Lys Leu Ile Asp Phe Leu Gln Ala Lys
```

```
                        645             650                 655
Met Asp Gln Pro Ala Lys Lys Lys Val Pro Leu Gln Tyr Asn Glu
                660                 665                 670
Leu Lys Leu Ala Leu Glu Lys Glu Lys Ala Arg Cys Ala Glu Leu Glu
                675                 680                 685
Glu Ala Leu Gln Lys Thr Arg Ile Glu Leu Arg Ser Ala Arg Glu Glu
            690                 695                 700
Ala Ala His Arg Lys Ala Thr Asp His Pro His Pro Ser Thr Pro Ala
705                 710                 715                 720
Thr Ala Arg Gln Gln Ile Ala Met Ser Ala Ile Val Arg Ser Pro Glu
                725                 730                 735
His Gln Pro Ser Ala Met Ser Leu Leu Ala Pro Pro Ser Ser Arg Arg
                740                 745                 750
Lys Glu Ser Ser Thr Pro Glu Glu Phe Ser Arg Arg Leu Lys Glu Arg
                755                 760                 765
Met His His Asn Ile Pro His Arg Phe Asn Val Gly Leu Asn Met Arg
                770                 775                 780
Ala Thr Lys Cys Ala Val Cys Leu Asp Thr Val His Phe Gly Arg Gln
785                 790                 795                 800
Ala Ser Lys Cys Leu Glu Cys Gln Val Met Cys His Pro Lys Cys Ser
                805                 810                 815
Thr Cys Leu Pro Ala Thr Cys Gly Leu Pro Ala Glu Tyr Ala Thr His
                820                 825                 830
Phe Thr Glu Ala Phe Cys Arg Asp Lys Met Asn Ser Pro Gly Leu Gln
                835                 840                 845
Ser Lys Glu Pro Gly Ser Ser Leu His Leu Glu Gly Trp Met Lys Val
                850                 855                 860
Pro Arg Asn Asn Lys Arg Gly Gln Gln Gly Trp Asp Arg Lys Tyr Ile
865                 870                 875                 880
Val Leu Glu Gly Ser Lys Val Leu Ile Tyr Asp Asn Glu Ala Arg Glu
                885                 890                 895
Ala Gly Gln Arg Pro Val Glu Glu Phe Glu Leu Cys Leu Pro Asp Gly
                900                 905                 910
Asp Val Ser Ile His Gly Ala Val Gly Ala Ser Glu Leu Ala Asn Thr
            915                 920                 925
Ala Lys Ala Asp Val Pro Tyr Ile Leu Lys Met Glu Ser His Pro His
            930                 935                 940
Thr Thr Cys Trp Pro Gly Arg Thr Leu Tyr Leu Leu Ala Pro Ser Phe
945                 950                 955                 960
Pro Asp Lys Gln Arg Trp Val Thr Ala Leu Glu Ser Val Val Ala Gly
                965                 970                 975
Gly Arg Val Ser Arg Glu Lys Ala Glu Ala Asp Ala Lys Leu Leu Gly
                980                 985                 990
Asn Ser Leu Leu Lys Leu Glu Gly Asp Asp Arg Leu Asp Met Asn Cys
                995                 1000                1005
Thr Leu Pro Phe Ser Asp Gln Val Val Leu Val Gly Thr Glu Glu
                1010                1015                1020
Gly Leu Tyr Ala Leu Asn Val Leu Lys Asn Ser Leu Thr His Ile
                1025                1030                1035
Pro Gly Ile Gly Ala Val Phe Gln Ile Tyr Ile Ile Lys Asp Leu
                1040                1045                1050
Glu Lys Leu Leu Met Ile Ala Gly Glu Glu Arg Ala Leu Cys Leu
                1055                1060                1065
```

-continued

```
Val Asp Val Lys Lys Val Lys Gln Ser Leu Ala Gln Ser His Leu
1070            1075                1080

Pro Ala Gln Pro Asp Val Ser Pro Asn Ile Phe Glu Ala Val Lys
1085            1090                1095

Gly Cys His Leu Phe Ala Ala Gly Lys Ile Glu Asn Ser Leu Cys
1100            1105                1110

Ile Cys Ala Ala Met Pro Ser Lys Val Val Ile Leu Arg Tyr Asn
1115            1120                1125

Asp Asn Leu Ser Lys Tyr Cys Ile Arg Lys Glu Ile Glu Thr Ser
1130            1135                1140

Glu Pro Cys Ser Cys Ile His Phe Thr Asn Tyr Ser Ile Leu Ile
1145            1150                1155

Gly Thr Asn Lys Phe Tyr Glu Ile Asp Met Lys Gln Tyr Thr Leu
1160            1165                1170

Asp Glu Phe Leu Asp Lys Asn Asp His Ser Leu Ala Pro Ala Val
1175            1180                1185

Phe Ala Ser Ser Ser Asn Ser Phe Pro Val Ser Ile Val Gln Ala
1190            1195                1200

Asn Ser Ala Gly Gln Arg Glu Glu Tyr Leu Leu Cys Phe His Glu
1205            1210                1215

Phe Gly Val Phe Val Asp Ser Tyr Gly Arg Arg Ser Arg Thr Asp
1220            1225                1230

Asp Leu Lys Trp Ser Arg Leu Pro Leu Ala Phe Ala Tyr Arg Glu
1235            1240                1245

Pro Tyr Leu Phe Val Thr His Phe Asn Ser Leu Glu Val Ile Glu
1250            1255                1260

Ile Gln Ala Arg Ser Ser Leu Gly Ser Pro Ala Arg Ala Tyr Leu
1265            1270                1275

Glu Ile Pro Asn Pro Arg Tyr Leu Gly Pro Ala Ile Ser Ser Gly
1280            1285                1290

Ala Ile Tyr Leu Ala Ser Ser Tyr Gln Asp Lys Leu Arg Val Ile
1295            1300                1305

Cys Cys Lys Gly Asn Leu Val Lys Glu Ser Gly Thr Glu Gln His
1310            1315                1320

Arg Val Pro Ser Thr Ser Arg Ser Ser Pro Asn Lys Arg Gly Pro
1325            1330                1335

Pro Thr Tyr Asn Glu His Ile Thr Lys Arg Val Ala Ser Ser Pro
1340            1345                1350

Ala Pro Pro Glu Gly Pro Ser His Pro Arg Glu Pro Ser Thr Pro
1355            1360                1365

His Arg Tyr Arg Asp Arg Glu Gly Arg Thr Glu Leu Arg Arg Asp
1370            1375                1380

Lys Ser Pro Gly Arg Pro Leu Glu Arg Glu Lys Ser Pro Gly Arg
1385            1390                1395

Met Leu Ser Thr Arg Arg Glu Arg Ser Pro Gly Arg Leu Phe Glu
1400            1405                1410

Asp Ser Ser Arg Gly Arg Leu Pro Ala Gly Ala Val Arg Thr Pro
1415            1420                1425

Leu Ser Gln Val Asn Lys Val Trp Asp Gln Ser Ser Val
1430            1435                1440
```

<210> SEQ ID NO 4
<211> LENGTH: 271

```
<212> TYPE: PRT
<213> ORGANISM: Homo sapiens

<400> SEQUENCE: 4

Tyr Gln Thr Ile Lys Ile Ile Gly Lys Gly Ala Phe Gly Val Lys
1               5                   10                  15

Leu Val Gln Lys Lys Ala Asp Gly Lys Val Tyr Ala Met Lys Ser Leu
            20                  25                  30

Ile Lys Thr Glu Met Phe Lys Lys Asp Gln Leu Ala His Val Arg Ala
        35                  40                  45

Glu Arg Asp Ile Leu Ala Glu Ser Asp Ser Pro Trp Val Val Lys Leu
    50                  55                  60

Tyr Thr Thr Phe Gln Asp Ala Asn Phe Leu Tyr Met Leu Met Glu Phe
65                  70                  75                  80

Leu Pro Gly Gly Asp Leu Met Thr Met Leu Ile Lys Tyr Glu Ile Phe
                85                  90                  95

Ser Glu Asp Ile Thr Arg Phe Tyr Ile Ala Glu Ile Val Leu Ala Ile
            100                 105                 110

Asp Ala Val His Lys Leu Gly Phe Ile His Arg Asp Ile Lys Pro Asp
        115                 120                 125

Asn Ile Leu Leu Asp Arg Gly His Val Lys Leu Thr Asp Phe Gly
    130                 135                 140

Leu Ser Thr Gly Phe His Lys Leu His Asp Asn Asn Tyr Tyr Thr Gln
145                 150                 155                 160

Leu Leu Gln Gly Lys Ser Met Ala Tyr Ser Thr Val Gly Thr Pro Asp
                165                 170                 175

Tyr Ile Ala Pro Glu Ile Phe Thr Gly His Gly Tyr Ser Phe Asp Cys
            180                 185                 190

Asp Trp Trp Ser Leu Gly Thr Ile Met Phe Glu Cys Leu Val Gly Trp
        195                 200                 205

Pro Pro Phe Cys Ala Glu Asp Ser His Asp Thr Tyr Arg Lys Ile Val
    210                 215                 220

Asn Trp Arg His Ser Leu Tyr Phe Pro Asp Asp Ile Thr Leu Gly Val
225                 230                 235                 240

Asp Ala Glu Asn Leu Ile Arg Ser Leu Ile Cys Asn Thr Glu Asn Arg
                245                 250                 255

Leu Gly Arg Gly Gly Ala His Glu Ile Lys Ser His Ala Phe Phe
            260                 265                 270

<210> SEQ ID NO 5
<211> LENGTH: 96
<212> TYPE: DNA
<213> ORGANISM: Homo sapiens

<400> SEQUENCE: 5
atgttgaagt tcaaatatgg agcgcggaat cctttggatg ctggtgctgc tgaacccatt      60
gccagccggg cctccaggct gaatctgttc ttccag                                96

<210> SEQ ID NO 6
<211> LENGTH: 142
<212> TYPE: DNA
<213> ORGANISM: Homo sapiens

<400> SEQUENCE: 6
gggaaaccac cctttatgac tcaacagcag atgtctcctc tttcccgaga agggatatta     60
gatgccctct tgttctctct tgaagaatgc agtcagcctg ctctgatgaa gattaagcac    120
```

```
gtgagcaact ttgtccggaa gt                                              142

<210> SEQ ID NO 7
<211> LENGTH: 176
<212> TYPE: DNA
<213> ORGANISM: Homo sapiens

<400> SEQUENCE: 7
attccgacac catagctgag ttacaggagc tccagccttc ggcaaaggac ttcgaagtca     60
gaagtcttgt aggttgtggt cactttgctg aagtgcaggt ggtaagagag aaagcaaccg    120
gggacatcta tgctatgaaa gtgatgaaga agaaggcttt attggcccag gagcag        176

<210> SEQ ID NO 8
<211> LENGTH: 102
<212> TYPE: DNA
<213> ORGANISM: Homo sapiens

<400> SEQUENCE: 8
gtttcatttt ttgaggaaga gcggaacata ttatctcgaa gcacaagccc gtggatcccc    60
caattacagt atgcctttca ggacaaaaat cacctttatc tg                       102

<210> SEQ ID NO 9
<211> LENGTH: 143
<212> TYPE: DNA
<213> ORGANISM: Homo sapiens

<400> SEQUENCE: 9
gtcatggaat atcagcctgg aggggacttg ctgtcacttt tgaatagata tgaggaccag    60
ttagatgaaa acctgataca gttttaccta gctgagctga ttttggctgt tcacagcgtt   120
catctgatgg gatacgtgca tcg                                            143

<210> SEQ ID NO 10
<211> LENGTH: 94
<212> TYPE: DNA
<213> ORGANISM: Homo sapiens

<400> SEQUENCE: 10
agacatcaag cctgagaaca ttctcgttga ccgcacagga cacatcaagc tggtggattt    60
tggatctgcc gcgaaaatga attcaaacaa gatg                                94

<210> SEQ ID NO 11
<211> LENGTH: 204
<212> TYPE: DNA
<213> ORGANISM: Homo sapiens

<400> SEQUENCE: 11
gtgaatgcca aactcccgat tgggacccca gattacatgg ctcctgaagt gctgactgtg    60
atgaacgggg atggaaaagg cacctacggc ctggactgtg actggtggtc agtgggcgtg   120
attgcctatg agatgattta tgcagatcc cccttcgcag agggaacctc tgccagaacc    180
ttcaataaca ttatgaattt ccag                                           204

<210> SEQ ID NO 12
<211> LENGTH: 13
<212> TYPE: PRT
<213> ORGANISM: Homo sapiens

<400> SEQUENCE: 12
```

-continued

Gln Glu Leu Gln Pro Ser Ala Lys Asp Phe Glu Val Arg
1               5                   10

<210> SEQ ID NO 13
<211> LENGTH: 13
<212> TYPE: PRT
<213> ORGANISM: Homo sapiens

<400> SEQUENCE: 13

Ala Ala Lys Met Asn Ser Asn Lys Met Val Asn Ala Lys
1               5                   10

<210> SEQ ID NO 14
<211> LENGTH: 13
<212> TYPE: PRT
<213> ORGANISM: Homo sapiens

<400> SEQUENCE: 14

Phe Ala Glu Gly Thr Ser Ala Arg Thr Phe Asn Asn Ile
1               5                   10

<210> SEQ ID NO 15
<211> LENGTH: 34
<212> TYPE: PRT
<213> ORGANISM: Homo sapiens

<400> SEQUENCE: 15

Glu Val Arg Ser Leu Val Gly Cys Gly His Phe Ala Glu Val Gln Val
1               5                   10                  15

Val Arg Glu Lys Ala Thr Gly Asp Ile Tyr Ala Met Lys Val Met Lys
            20                  25                  30

Lys Lys

<210> SEQ ID NO 16
<211> LENGTH: 23
<212> TYPE: PRT
<213> ORGANISM: Homo sapiens

<400> SEQUENCE: 16

Val His Leu Met Gly Tyr Val His Arg Asp Ile Lys Pro Glu Asn Ile
1               5                   10                  15

Leu Val Asp Arg Thr Gly His
            20

<210> SEQ ID NO 17
<211> LENGTH: 14
<212> TYPE: PRT
<213> ORGANISM: Homo sapiens

<400> SEQUENCE: 17

Val Ser Asn Phe Val Arg Lys Tyr Ser Asp Thr Ile Ala Glu
1               5                   10

<210> SEQ ID NO 18
<211> LENGTH: 14
<212> TYPE: PRT
<213> ORGANISM: Homo sapiens

<400> SEQUENCE: 18

Arg Lys Tyr Ser Asp Thr Ile Ala Glu Leu Gln Glu Leu Gln
1               5                   10

<210> SEQ ID NO 19

```
<211> LENGTH: 14
<212> TYPE: PRT
<213> ORGANISM: Homo sapiens

<400> SEQUENCE: 19

Gln Glu Leu Gln Pro Ser Ala Lys Asp Phe Glu Val Arg Ser
1               5                   10

<210> SEQ ID NO 20
<211> LENGTH: 13
<212> TYPE: PRT
<213> ORGANISM: Homo sapiens

<400> SEQUENCE: 20

Ala Gln Glu Gln Val Ser His Glu Glu Glu Arg Asn Ile
1               5                   10

<210> SEQ ID NO 21
<211> LENGTH: 16
<212> TYPE: PRT
<213> ORGANISM: Homo sapiens

<400> SEQUENCE: 21

Pro Leu Ser Arg Glu Gly Ile Leu Asp Ala Leu Phe Val Leu Phe Glu
1               5                   10                  15

<210> SEQ ID NO 22
<211> LENGTH: 20
<212> TYPE: DNA
<213> ORGANISM: Homo sapiens

<400> SEQUENCE: 22
tgaagttcaa atatggagcg                                              20

<210> SEQ ID NO 23
<211> LENGTH: 21
<212> TYPE: DNA
<213> ORGANISM: Homo sapiens

<400> SEQUENCE: 23
ctggaagaac agattcagcc t                                            21

<210> SEQ ID NO 24
<211> LENGTH: 20
<212> TYPE: DNA
<213> ORGANISM: Homo sapiens

<400> SEQUENCE: 24
tgaagttcaa atatggagcg                                              20

<210> SEQ ID NO 25
<211> LENGTH: 20
<212> TYPE: DNA
<213> ORGANISM: Homo sapiens

<400> SEQUENCE: 25
tggaagaaca gattcagcct                                              20

<210> SEQ ID NO 26
<211> LENGTH: 20
<212> TYPE: DNA
<213> ORGANISM: Homo sapiens

<400> SEQUENCE: 26
```
gcagatgtct cctctttccc                          20

<210> SEQ ID NO 27
<211> LENGTH: 20
<212> TYPE: DNA
<213> ORGANISM: Homo sapiens

<400> SEQUENCE: 27
gacaaagttg ctcacgtgct                          20

<210> SEQ ID NO 28
<211> LENGTH: 20
<212> TYPE: DNA
<213> ORGANISM: Homo sapiens

<400> SEQUENCE: 28
agatgtctcc tctttcccga                          20

<210> SEQ ID NO 29
<211> LENGTH: 20
<212> TYPE: DNA
<213> ORGANISM: Homo sapiens

<400> SEQUENCE: 29
gacaaagttg ctcacgtgct                          20

<210> SEQ ID NO 30
<211> LENGTH: 20
<212> TYPE: DNA
<213> ORGANISM: Homo sapiens

<400> SEQUENCE: 30
gttacaggag ctccagcctt                          20

<210> SEQ ID NO 31
<211> LENGTH: 20
<212> TYPE: DNA
<213> ORGANISM: Homo sapiens

<400> SEQUENCE: 31
cccggttgct ttctctctta                          20

<210> SEQ ID NO 32
<211> LENGTH: 20
<212> TYPE: DNA
<213> ORGANISM: Homo sapiens

<400> SEQUENCE: 32
ttacaggagc tccagccttc                          20

<210> SEQ ID NO 33
<211> LENGTH: 20
<212> TYPE: DNA
<213> ORGANISM: Homo sapiens

<400> SEQUENCE: 33
cccggttgct ttctctctta                          20

<210> SEQ ID NO 34
<211> LENGTH: 20
<212> TYPE: DNA
<213> ORGANISM: Homo sapiens

<400> SEQUENCE: 34

-continued tcatggaata tcagcctgga                                              20

<210> SEQ ID NO 35
<211> LENGTH: 20
<212> TYPE: DNA
<213> ORGANISM: Homo sapiens

<400> SEQUENCE: 35
cgtatcccat cagatgaacg                                              20

<210> SEQ ID NO 36
<211> LENGTH: 20
<212> TYPE: DNA
<213> ORGANISM: Homo sapiens

<400> SEQUENCE: 36
tcatggaata tcagcctgga                                              20

<210> SEQ ID NO 37
<211> LENGTH: 20
<212> TYPE: DNA
<213> ORGANISM: Homo sapiens

<400> SEQUENCE: 37
gatgcacgta tcccatcaga                                              20

<210> SEQ ID NO 38
<211> LENGTH: 20
<212> TYPE: DNA
<213> ORGANISM: Homo sapiens

<400> SEQUENCE: 38
cctccaggct caatctgttc                                              20

<210> SEQ ID NO 39
<211> LENGTH: 20
<212> TYPE: DNA
<213> ORGANISM: Homo sapiens

<400> SEQUENCE: 39
ggctgactgc attcttcaaa                                              20

<210> SEQ ID NO 40
<211> LENGTH: 20
<212> TYPE: DNA
<213> ORGANISM: Homo sapiens

<400> SEQUENCE: 40
cctccaggct gaatctgttc                                              20

<210> SEQ ID NO 41
<211> LENGTH: 20
<212> TYPE: DNA
<213> ORGANISM: Homo sapiens

<400> SEQUENCE: 41
gacaaagttg ctcacgtgct                                              20

<210> SEQ ID NO 42
<211> LENGTH: 20
<212> TYPE: DNA
<213> ORGANISM: Homo sapiens

```
<400> SEQUENCE: 42
tttgaagaat gcagtcagcc                                              20

<210> SEQ ID NO 43
<211> LENGTH: 20
<212> TYPE: DNA
<213> ORGANISM: Homo sapiens

<400> SEQUENCE: 43
cagcaaagtg accacaacct                                              20

<210> SEQ ID NO 44
<211> LENGTH: 20
<212> TYPE: DNA
<213> ORGANISM: Homo sapiens

<400> SEQUENCE: 44
gcagatgtct cctctttccc                                              20

<210> SEQ ID NO 45
<211> LENGTH: 20
<212> TYPE: DNA
<213> ORGANISM: Homo sapiens

<400> SEQUENCE: 45
cagcaaagtg accacaacct                                              20

<210> SEQ ID NO 46
<211> LENGTH: 20
<212> TYPE: DNA
<213> ORGANISM: Homo sapiens

<400> SEQUENCE: 46
aggttgtggt cactttgctg                                              20

<210> SEQ ID NO 47
<211> LENGTH: 20
<212> TYPE: DNA
<213> ORGANISM: Homo sapiens

<400> SEQUENCE: 47
tatgttccgc tcttcctcaa                                              20

<210> SEQ ID NO 48
<211> LENGTH: 20
<212> TYPE: DNA
<213> ORGANISM: Homo sapiens

<400> SEQUENCE: 48
taagagagaa agcaaccggg                                              20

<210> SEQ ID NO 49
<211> LENGTH: 20
<212> TYPE: DNA
<213> ORGANISM: Homo sapiens

<400> SEQUENCE: 49
tatgttccgc tcttcctcaa                                              20

<210> SEQ ID NO 50
<211> LENGTH: 20
<212> TYPE: DNA
<213> ORGANISM: Homo sapiens
```

```
<400> SEQUENCE: 50
ttgaggaaga gcggaacata                                                    20

<210> SEQ ID NO 51
<211> LENGTH: 20
<212> TYPE: DNA
<213> ORGANISM: Homo sapiens

<400> SEQUENCE: 51
tccaggctga tattccatga                                                    20

<210> SEQ ID NO 52
<211> LENGTH: 20
<212> TYPE: DNA
<213> ORGANISM: Homo sapiens

<400> SEQUENCE: 52
ttgaggaaga gcggaacata                                                    20

<210> SEQ ID NO 53
<211> LENGTH: 20
<212> TYPE: DNA
<213> ORGANISM: Homo sapiens

<400> SEQUENCE: 53
cctccaggct gatattccat                                                    20

<210> SEQ ID NO 54
<211> LENGTH: 20
<212> TYPE: DNA
<213> ORGANISM: Homo sapiens

<400> SEQUENCE: 54
gctgttcaca gcgttcatct                                                    20

<210> SEQ ID NO 55
<211> LENGTH: 20
<212> TYPE: DNA
<213> ORGANISM: Homo sapiens

<400> SEQUENCE: 55
aaatccacca gcttgatgtg                                                    20

<210> SEQ ID NO 56
<211> LENGTH: 20
<212> TYPE: DNA
<213> ORGANISM: Homo sapiens

<400> SEQUENCE: 56
cgttcatctg atgggatacg                                                    20

<210> SEQ ID NO 57
<211> LENGTH: 20
<212> TYPE: DNA
<213> ORGANISM: Homo sapiens

<400> SEQUENCE: 57
aaatccacca gcttgatgtg                                                    20

<210> SEQ ID NO 58
<211> LENGTH: 80
<212> TYPE: DNA
```

<213> ORGANISM: Homo sapiens

<400> SEQUENCE: 58
tgtccccggt tgctttctct cttaccacct gcacttcagc aaagtgacca caacctacaa    60
gacttctgac ttcgaagtcc                                                 80

<210> SEQ ID NO 59
<211> LENGTH: 80
<212> TYPE: DNA
<213> ORGANISM: Homo sapiens

<400> SEQUENCE: 59
tgatattcca tgaccagata aggtgattt ttgtcctgaa aggcatactg taattggggg     60
atccacgggc ttgtgcttcg                                                 80

<210> SEQ ID NO 60
<211> LENGTH: 20
<212> TYPE: DNA
<213> ORGANISM: Homo sapiens

<400> SEQUENCE: 60
taatacgact cactataggg                                                 20

<210> SEQ ID NO 61
<211> LENGTH: 18
<212> TYPE: DNA
<213> ORGANISM: Homo sapiens

<400> SEQUENCE: 61
atttaggtga cactatag                                                   18

<210> SEQ ID NO 62
<211> LENGTH: 20
<212> TYPE: DNA
<213> ORGANISM: Homo sapiens

<400> SEQUENCE: 62
gcagatgtct cctctttccc                                                 20

<210> SEQ ID NO 63
<211> LENGTH: 20
<212> TYPE: DNA
<213> ORGANISM: Homo sapiens

<400> SEQUENCE: 63
gacaaagttg ctcacgtgct                                                 20

<210> SEQ ID NO 64
<211> LENGTH: 20
<212> TYPE: DNA
<213> ORGANISM: Homo sapiens

<400> SEQUENCE: 64
gttacaggag ctccagcctt                                                 20

<210> SEQ ID NO 65
<211> LENGTH: 20
<212> TYPE: DNA
<213> ORGANISM: Homo sapiens

<400> SEQUENCE: 65
cccggttgct ttctctctta                                                 20

<210> SEQ ID NO 66
<211> LENGTH: 20
<212> TYPE: DNA
<213> ORGANISM: Homo sapiens

<400> SEQUENCE: 66
cagtcagcct gctctgatga                                              20

<210> SEQ ID NO 67
<211> LENGTH: 20
<212> TYPE: DNA
<213> ORGANISM: Homo sapiens

<400> SEQUENCE: 67
tcagcaaagt gaccacaacc                                              20

<210> SEQ ID NO 68
<211> LENGTH: 5
<212> TYPE: PRT
<213> ORGANISM: Homo sapiens

<400> SEQUENCE: 68

His Arg Asp Leu Lys
1               5

<210> SEQ ID NO 69
<211> LENGTH: 20
<212> TYPE: DNA
<213> ORGANISM: Homo sapiens

<400> SEQUENCE: 69
gaatgccaaa ctcccgattg                                              20

<210> SEQ ID NO 70
<211> LENGTH: 20
<212> TYPE: DNA
<213> ORGANISM: Homo sapiens

<400> SEQUENCE: 70
ccatccccgt tcatcacagt                                              20

<210> SEQ ID NO 71
<211> LENGTH: 28
<212> TYPE: DNA
<213> ORGANISM: Homo sapiens

<400> SEQUENCE: 71
ccccagatta catggctcct gaagtgct                                     28

<210> SEQ ID NO 72
<211> LENGTH: 733
<212> TYPE: DNA
<213> ORGANISM: homo sapiens

<400> SEQUENCE: 72
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300

```
ggctgaatgg caaggagtac aagtgcaagg tctccaacaa agccctccca accccccatcg    360 agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733

<210> SEQ ID NO 73
<211> LENGTH: 8
<212> TYPE: PRT
<213> ORGANISM: bacteriophage T7

<400> SEQUENCE: 73

Asp Tyr Lys Asp Asp Asp Asp Lys
1               5

<210> SEQ ID NO 74
<211> LENGTH: 39
<212> TYPE: DNA
<213> ORGANISM: Homo sapiens

<400> SEQUENCE: 74
gcagcagcgg ccgcgacttc gaagtcagaa gtcttgtag                            39

<210> SEQ ID NO 75
<211> LENGTH: 37
<212> TYPE: DNA
<213> ORGANISM: Homo sapiens

<400> SEQUENCE: 75
gcagcagtcg acctggaaat tcataatgtt attgaag                              37

<210> SEQ ID NO 76
<211> LENGTH: 39
<212> TYPE: DNA
<213> ORGANISM: Homo sapiens

<400> SEQUENCE: 76
gcagcagcgg ccgcatgttg aagttcaaat atggagcgc                            39

<210> SEQ ID NO 77
<211> LENGTH: 37
<212> TYPE: DNA
<213> ORGANISM: Homo sapiens

<400> SEQUENCE: 77
gcagcagtcg acaatgttat tgaaggttct ggcagag                              37
```

US 7,326,781 B2

POLYNUCLEOTIDES ENCODING THE HUMAN CITRON KINASE POLYPEPTIDE, BMSNKC_0020/0021

This application claims benefit to provisional application U.S. Ser. No. 60/372,745 filed Apr. 12, 2002, under 35 U.S.C. 119(e). The entire teachings of the referenced applications are incorporated herein by reference.

FIELD OF THE INVENTION

The present invention relates to a new protein kinase polypeptide, nucleotide sequences encoding the kinase polypeptide, as well as various products and methods useful for the diagnosis and treatment of various kinase-related diseases and conditions.

BACKGROUND OF THE INVENTION

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function.

Protein phosphorylation plays a pivotal role in cellular signal transduction. Among the biological functions controlled by this type of postranslational modification are: cell division, differentiation, and death (apoptosis); cell motility and cytoskeletal structure; control of DNA replication, transcription, splicing and translation; protein translocation events from the endoplasmic reticulum and Golgi apparatus to the membrane and extracellular space; protein nuclear import and export; and regulation of metabolic reactions, etc. Abnormal protein phosphorylation is widely recognized to be causally linked to the etiology of many diseases including cancer as well as immunologic, neuronal and metabolic disorders.

The presence of a phosphate moiety can modulate protein function in multiple ways. For example, common mechanism includes alterations in the catalytic properties ($V_{max}$ and $K_m$) of an enzyme, leading to its activation or inactivation. A second widely recognized mechanism involves promoting protein-protein interactions. One example is the tyrosine autophosphorylation of the ligand-activated EGF receptor tyrosine kinase. This event triggers high-affinity binding to the phosphotyrosine residue of the receptor's C-terminal intracellular domain to the SH2 motif of the adaptor molecule Grb2. Grb2, in turn, binds through its SH3 motif to a second adaptor molecule, such as SHC. The formation of this ternary complex activates the signaling events that are responsible for the biological effects of EGF. Serine and threonine phosphorylation events also have been recently recognized to exert their biological function through protein-protein interaction events that are mediated by the high-affinity binding of phosphoserine and phosphothreonine to WW motifs present in a large variety of proteins (Lu, P. J. et al (1999) *Science* 283:1325-1328).

A third important outcome of protein phosphorylation is changes in the subcellular localization of the substrate. As an example, nuclear import and export events in a large diversity of proteins are regulated by protein phosphorylation (Drier E. A. et al (1999) *Genes Dev* 13: 556-568).

Protein kinases are one of the largest families of eukaryotic proteins with several thousand known members. These proteins share a 250-300 amino acid domain that can be subdivided into 12 distinct subdomains that comprise the common catalytic core structure. These conserved protein motifs have recently been exploited using PCR-based and bioinformatic strategies leading to a significant expansion of the known kinases. Multiple alignment of the sequences in the catalytic domain of protein kinases and subsequent parsimony analysis permits their segregation into subfamilies of related kinases.

The best characterized protein kinases in eukaryotes phosphorylate proteins on the hydroxyl substituent of serine, threonine and tyrosine residues, which are the most common phospho-acceptor amino acid residues. However, phosphorylation on histidine has also been observed in bacteria.

Kinases fall largely into two groups: those specific for phosphorylating serines and threonines, and those specific for phosphorylating tyrosines. Some kinases, referred to as "dual specificity" kinases, are able to phosphorylate tyrosine as well as serine/threonine residues. Protein kinases can also be characterized by their location within the cell. Some kinases are transmembrane receptor-type proteins capable of directly altering their catalytic activity in response to the external environment, such as the binding of a ligand. Other kinases are non-receptor type proteins lacking any transmembrane domain; they can be found in a variety of cellular compartments from the inner surface of the cell membrane to the nucleus.

Many kinases are involved in regulatory cascades. The substrates of such kinases can include other kinases whose activities are regulated by their phosphorylation state. Ultimately, the activity of some downstream effector is modulated by phosphorylation resulting from activation of such a pathway. The conserved protein motifs of these kinases have recently been exploited using PCR-based cloning strategies leading to a significant expansion of the known kinases.

Multiple alignment of the sequences in the catalytic domain of protein kinases and subsequent parsimony analysis permits the segregation of related kinases into distinct branches of subfamilies including: tyrosine kinases (PTK's), dual-specificity kinases, and serine/threonine kinases (STK's). The latter subfamily includes cyclic nucleotide-dependent kinases, calcium/calmodulin kinases, cyclin-dependent kinases (CDKs), MAP kinases, serine-threonine kinase receptors, as well as and several other subfamilies.

The protein kinases can be classified into several major groups including AGC, CAMK, Casein kinase 1, CMGC, STE, tyrosine kinases, and atypical kinases (Plowman, G D et al., *Proceedings of the National Academy of Sciences*, USA, Vol. 96, Issue 24, 13603-13610, Nov. 23, 1999). In addition, there are a number of minor yet distinct families, including families related to worm- or fungal-specific kinases, and a family designated "other" to represent several smaller families. Within each group are several distinct families of more closely related kinases. In addition, an "atypical" family represents those protein kinases whose catalytic domain has little or no primary sequence homology to conventional kinases, including the A6 kinases and PI3 kinases.

The AGC kinases are basic amino acid-directed enzymes that phosphorylate residues found proximal to Arg and Lys. Examples within this group include the G protein-coupled receptor kinases (GRKs), the cyclic nucleotide-dependent kinases (PKA, PKC, PKG), NDR or DBF2 kinases, ribosomal S6 kinases, AKT kinases, myotonic dystrophy kinases (DMPKs), MAPK interacting kinases (NINKs), MAST kinases, and others.

The CAMK kinases ($Ca^{2+}$/calmodulin-regulated kinases) are also basic amino acid-directed kinases. They include the Ca$^{2+}$/calmodulin-regulated and AMP-dependent protein kinases (AMPK), myosin light chain kinases (MLCK), MAP kinase activating protein kinases (MAPKAPKs), checkpoint 2 kinases (CHK2), death-associated protein kinases (DAPKs), phosphorylase kinase (PHK), Rac and Rho-binding Trio kinases, a "unique" family of CAMKs, and the EMK-related protein kinases. The EMK family of STKs are involved in the control of cell polarity, microtubule stability and cancer. One member of the EMK family, C-TAK1, has been reported to control entry into mitosis by activating Cdc25C which in turn dephosphorylates Cdc2. Also included in the EMK family is MAKV, which has been shown to be overexpressed in metastatic tumors (Korobko IV, Kabishev A A, Kiselev S L. *Dokl. Akad. Nauk* 354 (4), 554-556 (1997)).

The CMGC kinases "proline-directed" enzymes that phosphorylate residues which exist in a proline-rich context. They include the cyclin-dependent kinases (CDKs), mitogen-activated protein kinases (MAPKs), glycogen synthase kinases-3 (GSK3s), RNA Dependent Helicase Kinase, and CDC-like kinase (CLK). Most CMGC kinases have larger than average kinase domains owing to the presence of insertions within subdomains X and XI. CDKs play a pivotal role in the regulation of mitosis during cell division. The process of cell division occurs in four stages: S phase, the period during which chromosomes duplicate, G2, mitosis (M), and G1 or interphase. During mitosis the duplicated chromosomes are evenly segregated allowing each daughter cell to receive a complete copy of the genome. A key mitotic regulator in all eukaryotic cells is the STK cdc2, a CDK regulated by cyclin B. However some CDK-like kinases, such as CDK5 are not cyclin associated, nor are they cell cycle regulated.

MAPKs play a pivotal role in many cellular signaling pathways, including stress response and mitogenesis (Lewis, T. S., Shapiro, P. S., and Ahn, N. G. (1998) *Adv. Cancer Res.* 74, 49-139). Growth factors such as EGF, and cytokines such as TNF-alpha, can activate MAP kinases. In response to EGF, Ras becomes activated and recruits Rafl to the membrane where Rafl is activated by mechanisms that can involve phosphorylation and conformational changes (Morrison, D. K., and Cutler, R. E. (1997) *Curr. Opin. Cell Biol.* 9, 174-179). Active Rafl phosphorylates MEK1 (MAP kinase kinase) which in turn phosphorylates and activates extracellular signal-regulated protein kinase (ERKs).

The tyrosine kinase group encompasses both cytoplasmic (e.g. src) as well as transmembrane receptor tyrosine kinases (e.g. EGF receptor). These kinases play a pivotal role in the signal transduction processes that mediate cell proliferation, differentiation, and apoptosis.

The STE family refers to the three classes of protein kinases that lie sequentially upstream of the MAPKs. This group includes STE7 (MEK or MAPKK) kinases, STE11 (MEKK or MAPKKK) kinases and STE20 (MEKKK) kinases. In humans, several protein kinase families that bear only distant homology with the STE11 family also operate at the level of MAPKKKs including RAF, MLK, TAK1, and COT. Since crosstalk takes place between protein kinases functioning at different levels of the MAPK cascade, the large number of STE family kinases could translate into an enormous potential for upstream signal specificity. The prototype, STE20 from baker's yeast, is regulated by hormone receptor signaling to directly affect cell cycle progression through the modulation of CDK activity. STE20 also coordinately regulates changes in the cytoskeleton and in transcriptional programs in a bifurcating pathway. In a similar manner, the homologous kinases in humans are likely to play a role in extracellular regulation of growth, cell adhesion and migration, and changes in transcriptional programs, all three of which have critical roles in tumorigenesis. Mammalian STE20-related protein kinases have been implicated in response to growth factors or cytokines, oxidative-, UV-, or irradiation-related stress pathways, inflammatory signals (e.g. TNFα), apoptotic stimuli (e.g. Fas), T and B cell costimulation, the control of cytoskeletal architecture, and cellular transformation.

Typically, the STE20-related kinases serve as upstream regulators of MAPK cascades. Examples include: HPK1, a protein-serine/threonine kinase (STK) having a STE20-like kinase domain that activates a protein kinase pathway leading to the stress-activated protein kinase, SAPK/JNK; PAK1, an STK with an upstream CDC42-binding domain that interacts with Rac and plays a role in cellular transformation through the Ras-MAPK pathway; and murine NIK, which interacts with upstream receptor tyrosine kinases and connects with downstream STE 11 family kinases.

NEK kinases are related to NIMA which is required for entry into mitosis in the filamentous fungus, *A. nidulans*. Mutations in the nimA gene cause the nim ("never in mitosis") G2 arrest phenotype in this fungus (Fry, A. M. and Nigg, E. A. (1995) *Current* Biology 5: 1122-1125). Several observations suggest that higher eukaryotes can have a NIMA functional counterpart(s): (1) expression of a dominant-negative form of NIMA in HeLa cells causes a G2 arrest; (2) overexpression of NIMA causes chromatin condensation, not only in *A. nidulans*, but also in yeast, *Xenopus oocytes* and HeLa cells (Lu, K. P. and Hunter, T. (1995) *Prog. Cell Cycle* Res. 1, 187-205); (3) NIMA, when expressed in mammalian cells, interacts with pinl, a phosphorylation-specific prolyl isomerase that functions in cell cycle regulation (Lu, K. P. et al. (1996) *Nature* 380, 544-547); (4) okadaic acid inhibitor studies suggests the presence of cdc2-independent mechanism to induce mitosis (Ghosh, S. et al.(1998) Exp. *Cell Res.* 242, 1-9); and (5) a NIMA-like kinase (fin 1) exists in another eukaryote besides *Aspergillus, Saccharomyces pombe* (Krien, M. J. E. et al.(1998) *J. Cell Sci.* 111, 967-976).

Four mammalian NIMA-like kinases have been identified: NEK1, NEK2, NEK3 and NRK2. Despite the similarity of the mammalian NIMA-related kinases to NIMA over the catalytic region, the mammalian kinases are structurally different from NIMA over the extracatalytic regions. In addition, the mammalian kinases do not complement the nim phenotype in *Aspergillus* nimA mutants.

The casein kinase, CK1, family represents a distant branch of the protein kinase family. One or more forms are ubiquitously distributed in mammalian tissues and cell lines. CK1 kinases are found in cytoplasm, in nuclei, membrane-bound, and associated with the cytoskeleton. Splice variants differ in their subcellular distribution.

Several families cluster within a group of unrelated kinases termed "Other". Included are: CHK1; Elongation 2 factor kinases (EIFK); homologues of the yeast sterile family kinases (STE), which refers to 3 classes of kinases which lie sequentially upstream of the MAPKs; Calcium-calmodulin kinase kinases (CAMKK); dual-specific tyrosine kinases (DYRK); IkB kinases (IKK); Integrin receptor kinase (IRAK); endoribonuclease-associated kinases (IRE); Mixed lineage kinase (MLK); LIM-domain containing kinase (LIMK); MOS; PIM; Receptor interacting kinase (RIP); SR-protein specific kinase (SRPK); RAF; Serine-threonine kinase receptors (STKR); TAK1; Testis specific kinase (TSK); tousled-related kinase (TSL); UNC51-related kinase (UNC); VRK; WEE; mitotic kinases (BUB 1, AURORA, PLK, and NIMA/NEK); several families that are close homologues to worm (C26C2.1, YQ09, ZC581.9, YFL033c, C24A1.3); Drosophila (SLOB), or yeast (YDOD sp, YGR262 sc) kinases; and others that are "unique," and do not cluster into any obvious family. Additional families, first identified in lower eukaryotes such as yeast or worms, include YNL020, YPL236, YQ09, YWY3, SCY1, CO1H6.9, and C26C2.1.

RIP2 is a serine-threonine kinase associated with the tumor necrosis factor (TNF) receptor complex and is implicated in the activation of NF-kappa B and cell death in mammalian cells. It has recently been demonstrated that RIP2 activates the MAPK pathway (Navas, et al., *J. Biol. Chem.* 1999 Nov. 19; 274(47):33684-33690). RIP2 activates AP-1 and serum response element-regulated expression by inducing the activation of the Elk1 transcription factor. RIP2 directly phosphorylates and activates ERK2 in vivo and in vitro. RIP2, in turn, is activated through its interaction with Ras-activated Rafl. These results highlight the integrated nature of kinase signaling pathways.

The tousled (TSL) kinase was first identified in the plant *Arabidopsis thaliana*. TSL encodes a serine/threonine kinase that is essential for proper flower development. Human tousled-like kinases (Tlks) are cell-cycle-regulated enzymes, displaying maximal activities during S phase. This regulated activity suggests that Tlk function is linked to ongoing DNA replication (Sillje, et al., *EMBO*. 1999 Oct. 15;18(20):5691-5702).

The "histidine" kinases are abundant in prokaryotes, with more than 20 representatives in *E. coli*, and have also been identified in yeast, molds, and plants. In response to external stimuli, these kinases act as part of two-component systems to regulate DNA replication, cell division, and differentiation through phosphorylation of an aspartate in the target protein. To date, no "histidine" kinases have been identified in metazoans, although mitochondria pyruvate dehydrogenase kinase (PDK) and branched chain alpha-ketoacid dehydrogenase (BCKD) kinase, have sequence homology. PDK and BCKD kinases represent a unique family of atypical protein kinases involved in the regulation of glycolysis, the citric acid cycle, and protein synthesis during protein malnutrition. Structurally, they conserve only the C-terminal portion of "histidine" kinases including the G box regions. BCKD kinase phosphorylates the Ela subunit of the BCKD complex on Ser-293, proving it to be a functional protein kinase.

There are several proteins with protein kinase activity that appear to be structurally unrelated to the eukaryotic protein kinases. These include: *Dictyostelium myosin* heavy chain kinase A (MHCKA); *Physarum polycephalum* actin-fragmin kinase; the human A6 PTK; human BCR; mitochondria pyruvate dehydrogenase and branched chain fatty acid dehydrogenase kinase; and the prokaryotic "histidine" protein kinase family. The slime mold, worm, and human eEF-2 kinase homologues have all been demonstrated to have protein kinase activity, yet they bear little resemblance to conventional protein kinases except for the presence of an identified GxGxxG ATP binding motif.

Several other proteins contain protein kinase-like homology including: receptor guanylyl cyclases, diacylglycerol kinases, choline/ethanolamine kinases, and YLK1-related antibiotic resistance kinases. Each of these families contains short motifs that were recognized by profile searches with low scoring E-values, but a priori would not be expected to function as protein kinases. Instead, the similarity could simply reflect the modular nature of protein evolution and the primal role of ATP binding in diverse phosphotransfer enzymes. However, studies of a bacterial homologue of the YLK1 family suggests that the aminoglycoside phosphotransferases (APHs) are structurally and functionally related to protein kinases (Daigle, D. M., McKay, G. A., Thompson, P. R., Wright, G. D, *Chem. Biol.,* 6(1):11-8, (1999)). There are over 40 APHs identified from bacteria that are resistant to aminoglycosides such as kanamycin, gentamycin, or amikacin. The crystal structure of one well characterized APH reveals that it shares greater than 40% structural identity with the 2 lobed structure of the catalytic domain of cAMP-dependent protein kinase (PKA), including an N-terminal lobe composed of a 5-stranded antiparallel beta sheet, and the core of the C-terminal lobe including several invariant segments found in all protein kinases. APHs lack the GxGxxG consensus sequence normally present in the loop between beta strands 1 and 2, but contain 7 of the 12 strictly conserved residues present in most protein kinases, including the HGDxxxN signature sequence in kinase subdomain VIB. Furthermore, APH also has been shown to exhibit protein serine/threonine kinase activity, suggesting that other YLK-related molecules can indeed be functional protein kinases.

The eukaryotic lipid kinases (PI3Ks, PI4Ks, and PIPKs) also contain several short motifs similar to protein kinases, but otherwise share minimal primary sequence similarity. However, once again, structural analysis of PIPKII-beta defines a conserved ATP-binding core that is strikingly similar to conventional protein kinases. Three residues are conserved among all of these enzymes including (relative to the PKA sequence) Lys-72 which binds the gamma phosphate of ATP, Asp-166, which is part of the HRDLK (SEQ ID NO:68) motif, and Asp-184 from the conserved $Mg^{2+}$ or $Mn^{2+}$-binding DFG motif. The worm genome contains 12 phosphatidylinositol kinases, including three PI3-kinases, two PI4-kinases, four PIP5-kinases, and 4 PI3-kinase-related kinases. The latter group has 4 mammalian members (DNA-PK, FRAP/TOR, ATM, and ATR), which have been shown to participate in the maintenance of genomic integrity in response to DNA damage, and exhibit true protein kinase activity, thus suggesting that other PI-kinases can also act as protein kinases. Regardless of whether they have true protein kinase activity, PI3-kinases are tightly linked to protein kinase signaling, as evidenced by their downstream involvement with many growth factor receptors and as upstream activators of the cell survival response mediated by the AKT protein kinase.

Human citron kinase is a serine-threonine protein kinase involved in cytokinesis and apoptosis. The mouse ortholog was described in citron-kinase knockout mice studies (Di Cunto, et al. *Neuron* 28:115-127, 2000) and proposed by in vitro studies to be a crucial effector of Rho in regulation of cytokinesis. In the study by Di Cunto, et al., citron-K knock-out mice grew at slower rates, were severly ataxic, and died before adulthood as a consequence of fatal seizures. Their brains displayed defective neurogenesis, with depleted specific neuronal populations. These types of abnormalities typically arise during development of the central nervous system due to altered cytokinesis and massive apoptosis. Thus, human citron kinase can be of great value in the treatment and prevention of central nervous system-related diseases, disorders, and conditions.

The following abbreviations are used to represent the kinases described throughout the present disclosure: CitK: Citron Kinase; DM: myotonic dystrophy kinase; PsPK5: *Pisum sativum* protein kinase 5; SGK1: Serum and glucocorticoid-regulated kinase; COT-1; COUP transcription factor 1 (also called COUP-TF1, COUP-TF I, and V-ERBA related protein EAR-3); MAST250: Microtubule-associated Kinase; ATPK5: *Arabidopsis thaliana* protein kinase 5; ATPK64: *Arabidopsis thaliana* Protein kinase 64; ATPK67: *Arabidopsis thaliana* protein kinase 67, and EGFR kinase: Epidermal Growth Factor receptor kinase.

SUMMARY OF THE INVENTION

The present invention provides a novel human protein kinase, BMSNKC_0020/0021 (also referred to herein as CitK). Based on sequence homology, the protein kinase is 61% similar and 47.4% identical to COT-1 kinase (AF070066) and, more particularly, to murine citron kinase (CitK; P1_310805), i.e. 89.9% identical and 93.1% similar at the amino acid level. A phosphorylation site, an ATP protein kinase domain, and a serine/threonine protein kinase site, which are characteristic features of a protein kinase, have been identified in the BMSNKC_0020/0021 protein sequence. Preferably, the kinase of this invention is a serine-threonine kinase.

The present invention provides a polynucleotide, preferably full-length, and its encoded human citron protein kinase polypeptide. The protein kinase polynucleotide and encoded polypeptide product, can be involved in a variety of diseases, disorders and conditions associated with protein kinase activity, particularly, citron kinase activity. In one embodiment, the present invention is concerned with the modulation of the protein kinase polynucleotide and encoded product, particularly in providing treatments and therapies for relevant diseases. Antagonizing or inhibiting the action of the protein kinase polynucleotide and polypeptide is especially encompassed by the present invention.

It is an aspect of this invention to provide the isolated protein kinase polynucleotide as depicted in SEQ ID NO:1. Another aspect of this invention is to provide the protein kinase polypeptide, encoded by the polynucleotide of SEQ ID NO:1 and having the encoded amino acid sequence of SEQ ID NO:2, peptides thereof, or a functional or biologically active portion of this sequence. One aspect of the invention features an identified, isolated, enriched, or purified nucleic acid molecule of SEQ ID NO:1 encoding the novel protein kinase polypeptide (SEQ ID NO:2).

It is yet another aspect of the invention to provide compositions comprising the protein kinase polynucleotide sequence of this invention, or fragments thereof, or the encoded protein kinase polypeptide, or fragments or portions thereof. Preferably, a fragment or portion of the protein kinase polynucleotide and polypeptide is functional or active. In addition, this invention provides pharmaceutical compositions comprising the protein kinase polynucleotide or polypeptide as described herein, or a functional portion thereof, wherein the compositions further comprise a pharmaceutically and physiologically acceptable carrier, excipient, or diluent.

A further aspect of this invention provides a polynucleotide sequence comprising the complement of SEQ ID NO:1, or variants thereof. In addition, the invention encompasses variations or modifications of the protein kinase sequence which are a result of degeneracy of the genetic code, where the polynucleotide sequence can hybridize under moderate or high stringency conditions to the polynucleotide sequence of SEQ ID NO:1.

In another aspect, the present invention provides a nucleic acid sequence encoding the novel protein kinase polypeptide and antisense of the nucleic acid sequence, as well as oligonucleotides, fragments, or portions of the nucleic acid molecule or antisense molecule. Also provided are expression vectors and host cells comprising the polynucleotide that encodes the protein kinase polypeptide of the invention.

Another aspect of the invention is to provide methods for producing a polypeptide comprising the amino acid sequence of SEQ ID NO:2, or a fragment thereof, preferably, a functional fragment or portion thereof, comprising the steps of: a) cultivating a host cell containing an expression vector containing at least a functional fragment of the polynucleotide sequence encoding the protein kinase according to this invention under conditions suitable for the expression of the polypeptide; and b) recovering the polypeptide from the host cell.

Another aspect of this invention is to provide a substantially purified modulator, preferably an antagonist or inhibitor, of the protein kinase polypeptide of SEQ ID NO:2. In this regard, and by way of example, a purified antibody, or antigenic epitope thereof, that binds to a polypeptide comprising the amino acid sequence of SEQ ID NO:2, or a homologue encoded by a polynucleotide having a nucleic acid sequence as set forth in SEQ ID NO:1, or degenerate sequence thereof, is provided.

As yet another aspect the present invention provides a protein kinase nucleic acid sequence, its encoded polypeptide, peptides thereof, and antibodies directed against the polypeptide or peptides, for use in the diagnosis and/or screening of disorders or diseases associated with expression of one or more of the protein kinase polynucleotides and their encoded polypeptide products as described herein.

Another aspect of this invention is to provide diagnostic probes or primers for detecting disorders and/or diseases associated with the activity of the protein kinase of this invention, and/or for monitoring a patient's response to therapy. The probe or primer sequences comprise nucleic acid or amino acid sequences of the protein kinase described herein.

It is a further aspect of the present invention to provide a method for detecting a polynucleotide that encodes the described protein kinase polypeptide in a biological sample comprising the steps of: a) hybridizing the complement of the polynucleotide sequence encoding SEQ ID NO:2 to the nucleic acid material of a biological sample, thereby forming a hybridization complex; and b) detecting the hybridization complex, wherein the presence of the complex correlates with the presence of a polynucleotide encoding the protein kinase polypeptide in the biological sample. The nucleic acid material can be further amplified by the polymerase chain reaction prior to hybridization.

Another aspect of this invention is to provide methods for screening for agents which modulate the protein kinase polypeptide of the present invention, e.g., agonists and antagonists, particularly those that are obtained from the screening methods as described.

In yet a further aspect, the invention provides methods for detecting genetic predisposition, susceptibility, and response to therapy of diseases, disorders, or conditions that are associated with the activity of the protein kinase described herein.

It is another aspect of the present invention to provide a method for the treatment or prevention of several protein kinase-associated diseases or disorders including, but not limited to, cancers, and/or cardiovascular, immune, or neurological diseases or disorders. The method involves administering to an individual in need of such treatment or prevention an effective amount of a purified modulator, e.g. antagonist, of the disclosed protein kinase polypeptide.

It is yet another aspect of this invention to provide diagnostic kits for the determination of the nucleotide sequences of alleles of the human protein kinase described herein. The kits can comprise reagents and instructions for amplification-based assays, nucleic acid probe assays, protein nucleic acid probe assays, antibody assays or any combination thereof. Such kits are suitable for screening and diagnosing disorders associated with aberrant or uncontrolled cellular development and with the expression of the protein kinase polynucleotide and encoded protein kinase polypeptide, as described herein.

Further aspects, features, and advantages of the present invention will be better understood upon a reading of the detailed description of the invention when considered in connection with the accompanying figures or drawings.

The invention further relates to a polynucleotide encoding a polypeptide fragment of SEQ ID NO:2, or a polypeptide fragment encoded by the cDNA sequence included in the deposited clone, which is hybridizable to SEQ ID NO:1.

The invention further relates to a polynucleotide encoding a polypeptide domain of SEQ ID NO:2 or a polypeptide domain encoded by the cDNA sequence included in the deposited clone, which is hybridizable to SEQ ID NO:1.

The invention further relates to a polynucleotide encoding a polypeptide epitope of SEQ ID NO:2 or a polypeptide epitope encoded by the cDNA sequence included in the deposited clone, which is hybridizable to SEQ ID NO:1.

The invention further relates to a polynucleotide encoding a polypeptide of SEQ ID NO:2 or the cDNA sequence included in the deposited clone, which is hybridizable to SEQ ID NO:1, having biological activity.

The invention further relates to a polynucleotide which is a variant of SEQ ID NO:1.

The invention further relates to a polynucleotide which is an allelic variant of SEQ ID NO:1.

The invention further relates to a polynucleotide which encodes a species homologue of the SEQ ID NO:2.

The invention further relates to a polynucleotide which represents the complimentary sequence (antisense) of SEQ ID NO:1.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, wherein the polynucleotide fragment comprises a nucleotide sequence encoding an BMSNKC_0020/0021 protein.

The invention further relates to an isolated nucleic acid molecule of SEQ ID NO:1, wherein the polynucleotide fragment comprises a nucleotide sequence encoding the sequence identified as SEQ ID NO:2 or the polypeptide encoded by the cDNA sequence included in the deposited clone, which is hybridizable to SEQ ID NO:1.

The invention further relates to an isolated nucleic acid molecule of of SEQ ID NO:1, wherein the polynucleotide fragment comprises the entire nucleotide sequence of SEQ ID NO:1 or the cDNA sequence included in the deposited clone, which is hybridizable to SEQ ID NO:1.

The invention further relates to an isolated nucleic acid molecule of SEQ ID NO:1, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2 or the encoded sequence included in the deposited clone.

The invention further relates to a polypeptide fragment of SEQ ID NO:2 or the encoded sequence included in the deposited clone, having biological activity.

The invention further relates to a polypeptide domain of SEQ ID NO:2 or the encoded sequence included in the deposited clone.

The invention further relates to a polypeptide epitope of SEQ ID NO:2 or the encoded sequence included in the deposited clone.

The invention further relates to a full length protein of SEQ ID NO:2 or the encoded sequence included in the deposited clone.

The invention further relates to a variant of SEQ ID NO:2.

The invention further relates to an allelic variant of SEQ ID NO:2.

The invention further relates to a species homologue of SEQ ID NO:2.

The invention further relates to the isolated polypeptide of of SEQ ID NO:2, wherein the full length protein comprises sequential amino acid deletions from either the C-terminus or the N-terminus.

The invention further relates to an isolated antibody that binds specifically to the isolated polypeptide of SEQ ID NO:2.

The invention further relates to a method for preventing, treating, or ameliorating a medical condition, comprising administering to a mammalian subject a therapeutically effective amount of the polypeptide of SEQ ID NO:2 or the polynucleotide of SEQ ID NO:1.

The invention further relates to a method of diagnosing a pathological condition or a susceptibility to a pathological condition in a subject comprising the steps of (a) determining the presence or absence of a mutation in the polynucleotide of SEQ ID NO:1; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of of SEQ ID NO:2 in a biological sample; and diagnosing a pathological condition or a susceptibility to a pathological condition based on the presence or amount of expression of the polypeptide.

The invention further relates to a method for identifying a binding partner to the polypeptide of SEQ ID NO:2 comprising the steps of (a) contacting the polypeptide of SEQ ID NO:2 with a binding partner; and (b) determining whether the binding partner effects an activity of the polypeptide.

The invention further relates to a gene corresponding to the cDNA sequence of SEQ ID NO:1.

The invention further relates to a method of identifying an activity in a biological assay, wherein the method comprises the steps of (a) expressing SEQ ID NO:1 in a cell, (b) isolating the supernatant; (c) detecting an activity in a biological assay; and (d) identifying the protein in the supernatant having the activity.

The invention further relates to a process for making polynucleotide sequences encoding gene products having altered SEQ ID NO:2 activity comprising the steps of (a) shuffling a nucleotide sequence of SEQ ID NO:1, (b) expressing the resulting shuffled nucleotide sequences and, (c) selecting for altered activity as compared to the activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of SEQ ID NO:2 activity.

The invention further relates to a method for preventing, treating, or ameliorating a medical condition with the polypeptide provided as SEQ ID NO:2, in addition to, its encoding nucleic acid, or a modulator thereof, wherein the medical condition is selected from the group consisting of: lung cancer or related proliferative condition of the lung; ovarian cancer or related proliferative condition of the ovary; breast cancer or related proliferative condition of the breast; colon cancer or related proliferative condition of the colon; skin cancer or related proliferative condition of the skin; melonoma; immune disorders; hematopoetic disorders; developmental disorders; brain developmental disorders; male reproductive disorders; testicular disorders; testicular cancer; disorders associated with the chromosome 12q24 1-3 locus; brain disorders; brain cancer; CNS disorders; neurogenesis disorders; cytokinesis disorders; apoptosis disorders; longevity disorders; epilepsy; movement disorders; gaits; jerks; disorders associated with aberrant cyclin D1 regulation; disorders associated with aberrant apoptosis regulation; disorders associated with aberrant caspase-3 regulation; lissencephalies; disorders associated with reductions in the level of function of GABA-ergic interneurons; disorders associated with reduction in the amount or function of the hippocampal dentate gyrus; and disorders associated with reduction in the amount or function of the amygala.

The invention further relates to a method of diagnosing a pathological condition or a susceptibility to a pathological condition in a subject comprising the steps of (a) determining the presence or amount of expression of the polypeptide of of SEQ ID NO:2 in a biological sample; (b) and diagnosing a pathological condition or a susceptibility to a pathological condition based on the presence or amount of expression of the polypeptide relative to a control, wherein said condition is a member of the group consisting of: lung cancer or related proliferative condition of the lung; ovarian cancer or related proliferative condition of the ovary; breast cancer or related proliferative condition of the breast; colon cancer or related proliferative condition of the colon; skin cancer or related proliferative condition of the skin; melonoma; immune disorders; hematopoetic disorders; developmental disorders; brain developmental disorders; male reproductive disorders; testicular disorders; testicular cancer; disorders associated with the chromosome 12q24 1-3 locus; brain disorders; brain cancer; CNS disorders; neurogenesis disorders; cytokinesis disorders; apoptosis disorders; longevity disorders; epilepsy; movement disorders; gaits; jerks; disorders associated with aberrant cyclin D1 regulation; disorders associated with aberrant apoptosis regulation; disorders associated with aberrant caspase-3 regulation; lissencephalies; disorders associated with reductions in the level of function of GABA-ergic interneurons; disorders associated with reduction in the amount or function of the hippocampal dentate gyrus; and disorders associated with reduction in the amount or function of the amygala.

The invention further relates to a method of identifying a compound that modulates the biological activity of BMSNKC_0020/0021, comprising the steps of, (a) combining a candidate modulator compound with BMSNKC_0020/0021 having the sequence set forth in one or more of SEQ ID NO:2; and measuring an effect of the candidate modulator compound on the activity of BMSNKC_0020/0021.

The invention further relates to a method of identifying a compound that modulates the biological activity of a serine/threonine kinase, comprising the steps of, (a) combining a candidate modulator compound with a host cell expressing BMSNKC_0020/0021 having the sequence as set forth in SEQ ID NO:2; and, (b) measuring an effect of the candidate modulator compound on the activity of the expressed BMSNKC_0020/0021.

The invention further relates to a method of identifying a compound that modulates the biological activity of BMSNKC_0020/0021, comprising the steps of, (a) combining a candidate modulator compound with a host cell containing a vector described herein, wherein BMSNKC_0020/0021 is expressed by the cell; and, (b) measuring an effect of the candidate modulator compound on the activity of the expressed BMSNKC_0020/0021.

The invention further relates to a method of screening for a compound that is capable of modulating the biological activity of BMSNKC_0020/0021, comprising the steps of: (a) providing a host cell described herein; (b) determining the biological activity of BMSNKC_0020/0021 in the absence of a modulator compound; (c) contacting the cell with the modulator compound; and (d) determining the biological activity of BMSNKC_0020/0021 in the presence of the modulator compound; wherein a difference between the activity of BMSNKC_0020/0021 in the presence of the modulator compound and in the absence of the modulator compound indicates a modulating effect of the compound.

The invention further relates to a method of screening for a compound that is capable of modulating the biological activity of BMSNKC_0020/0021, comprising any one of the method steps described herein, further comprising a member of the group consisting of: Rho, Rac, vector capable of expressing Rho, vector capable of expressing Rac, host cells capable of expression Rho endogenously or recombinately, host cells capable of expression Rac endogenously or recombinately, modulators of Rho, and modulators of Rac.

The invention further relates to a compound that modulates the biological activity of human BMSNKC_0020/0021 as identified by the methods described herein.

BRIEF DESCRIPTION OF THE FIGURES

FIG. 1 shows the polynucleotide sequence (SEQ ID NO:1) and deduced amino acid sequence (SEQ ID NO:2) of the novel human protein kinase, BMSNKC_0020/0021 of the present invention. The standard one-letter abbreviation for amino acids is used to illustrate the deduced amino acid sequence. The polynucleotide sequence contains a sequence of 957 nucleotides (SEQ ID NO:1), encoding a polypeptide of 319 amino acids (SEQ ID NO:2). An analysis of the BMSNKC_0020/0021 polypeptide determined that it comprised the following features: a kinase domain located from about amino acid 96 to about amino acid 319 of SEQ ID NO:2, represented by double underlining.GenewiseDB was employed in this determination.

FIG. 2 presents the sequence alignment of the translated sequence of the protein kinase compared with other kinase sequences. The GCG pileup program was used to generate the alignment. The solid vertical bars represent identical amino acids. The amino acid sequences are aligned as follows. Citron protein kinase (SEQ ID NO:2) is the full length predicted amino acid sequence of the novel human citron kinase-related kinase of the invention (bottom line; BMSNKC_0020/0021); and kinase 310805 (top line; SEQ ID NO:3) is the known mouse (*Mus musculus*) citron kinase from GENBANK.

FIGS. 3A-C present a protein sequence alignment of the novel human protein kinase (citronkina; BMSNKC_0020/0021; SEQ ID NO:2), cot1 (SEQ ID NO:4 from the SDSC Kinase website), and the mouse citron kinase sequence from GenBank (Mus; kinase 310805; SEQ ID NO:3).

DESCRIPTION OF THE INVENTION

Figure 4:
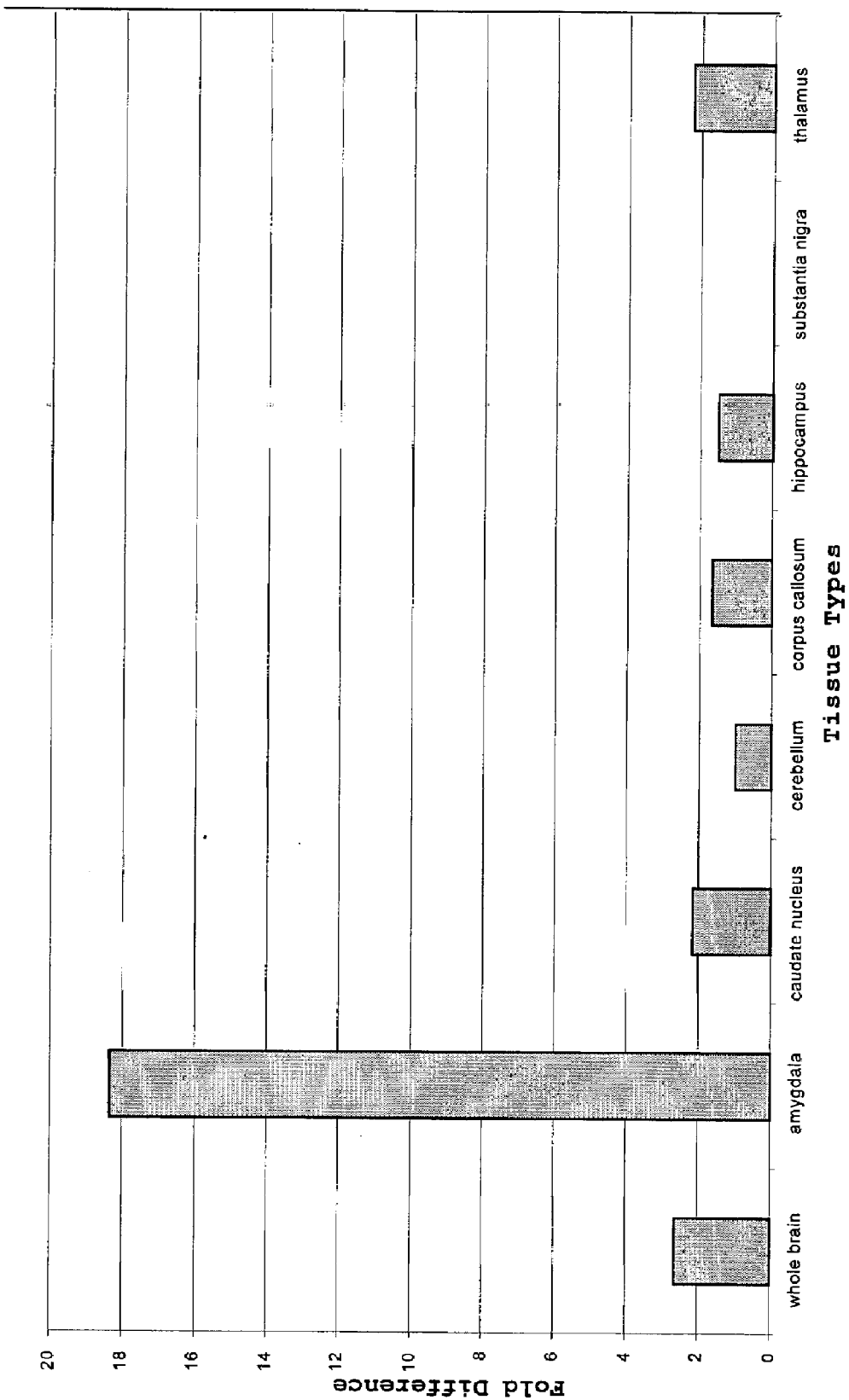
FIG. 4 shows expression profiling in brain of the novel human protein kinase as described in Example 4 using the Batch 1 primers of SEQ ID NOS: 64 and 65.
Figure 5:
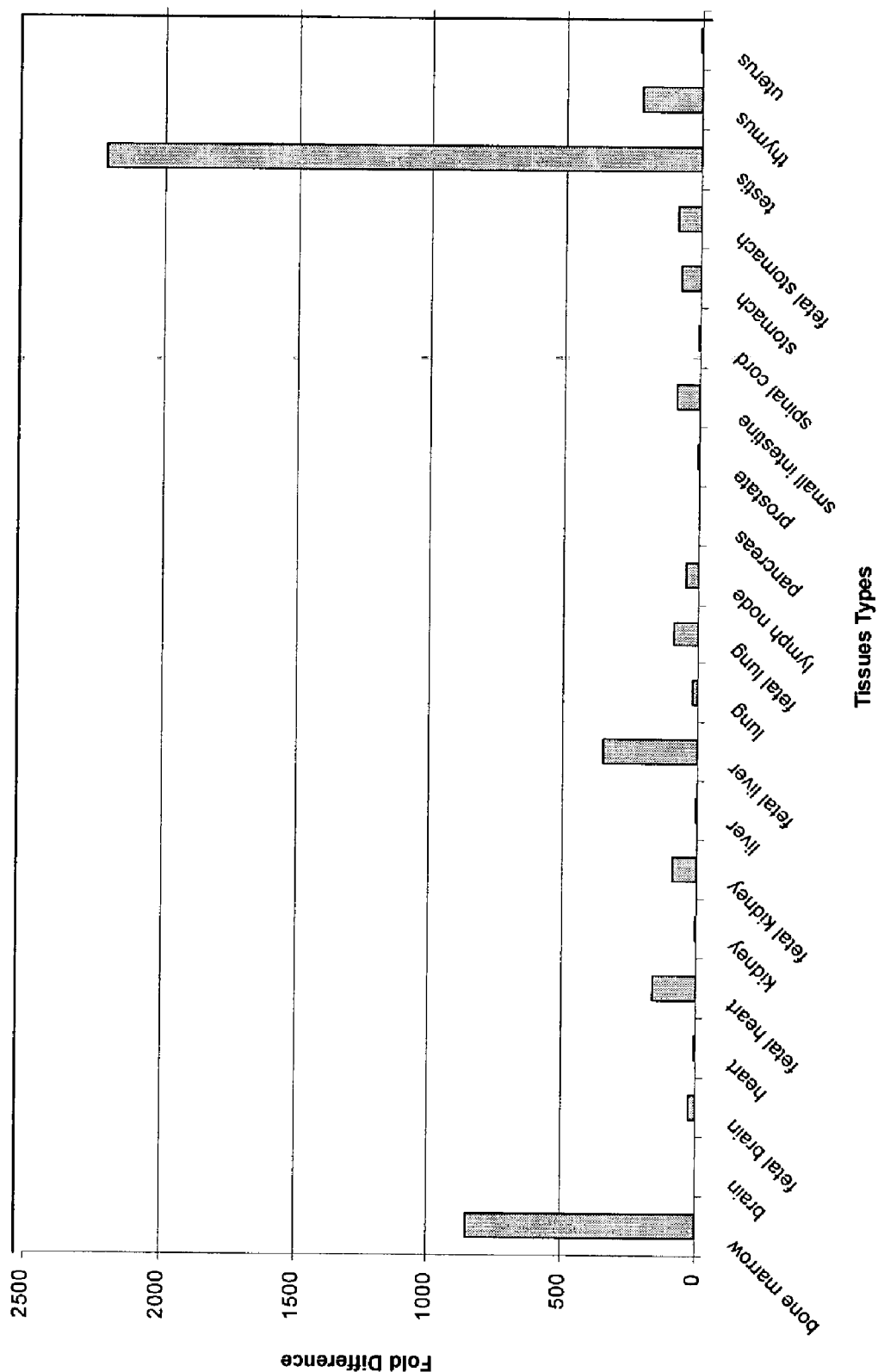
FIG. 5 shows expression profiling of the novel human protein kinase as expressed in various human adult and fetal tissues using the Batch 1 primers of SEQ ID NOS: 64 and 65.
Figure 6:
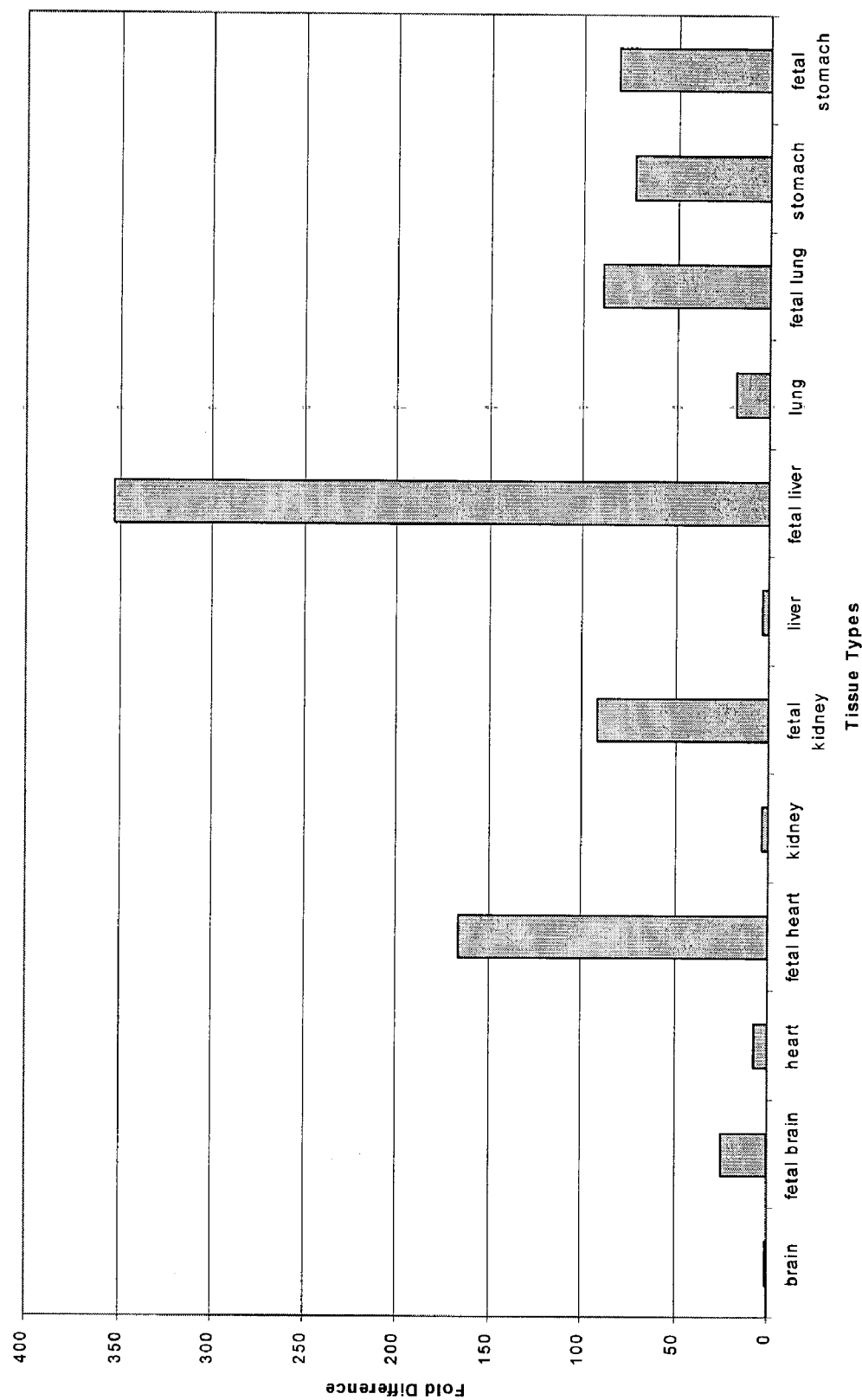
FIG. 6 shows expression profiling of the novel human protein kinase as expressed in human adult and fetal brain, heart, kidney, liver, and stomach tissues using the Batch 1 primers of SEQ ID NOS: 64 and 65.
Figure 7:
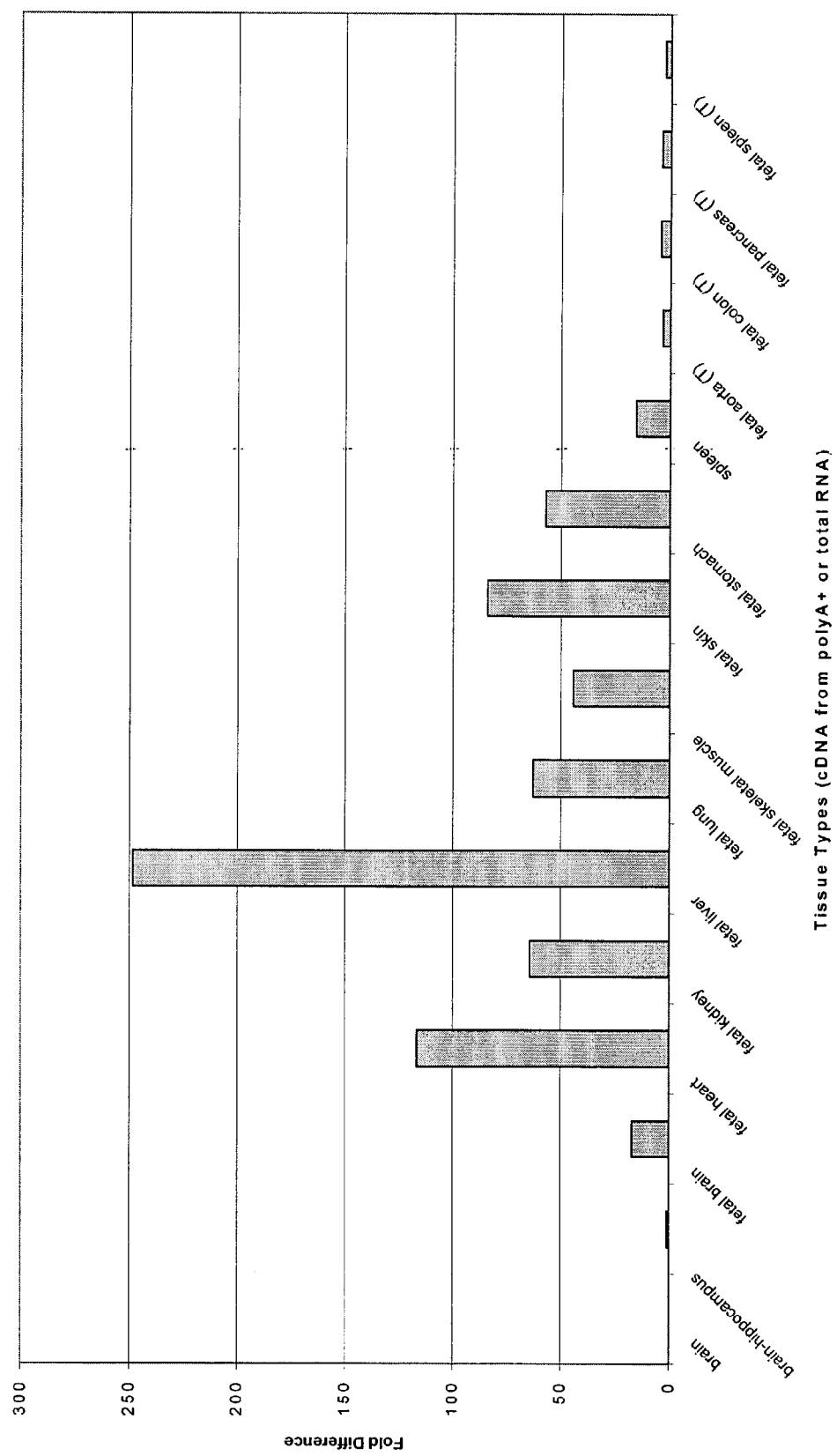
FIG. 7 shows expression profiling of the novel human protein kinase as expressed in various human fetal tissues compared to adult brain and spleen tissues (cDNA is from polyA+ or total RNA) using the Batch 1 primers of SEQ ID NOS: 64 and 65.
Figure 8:
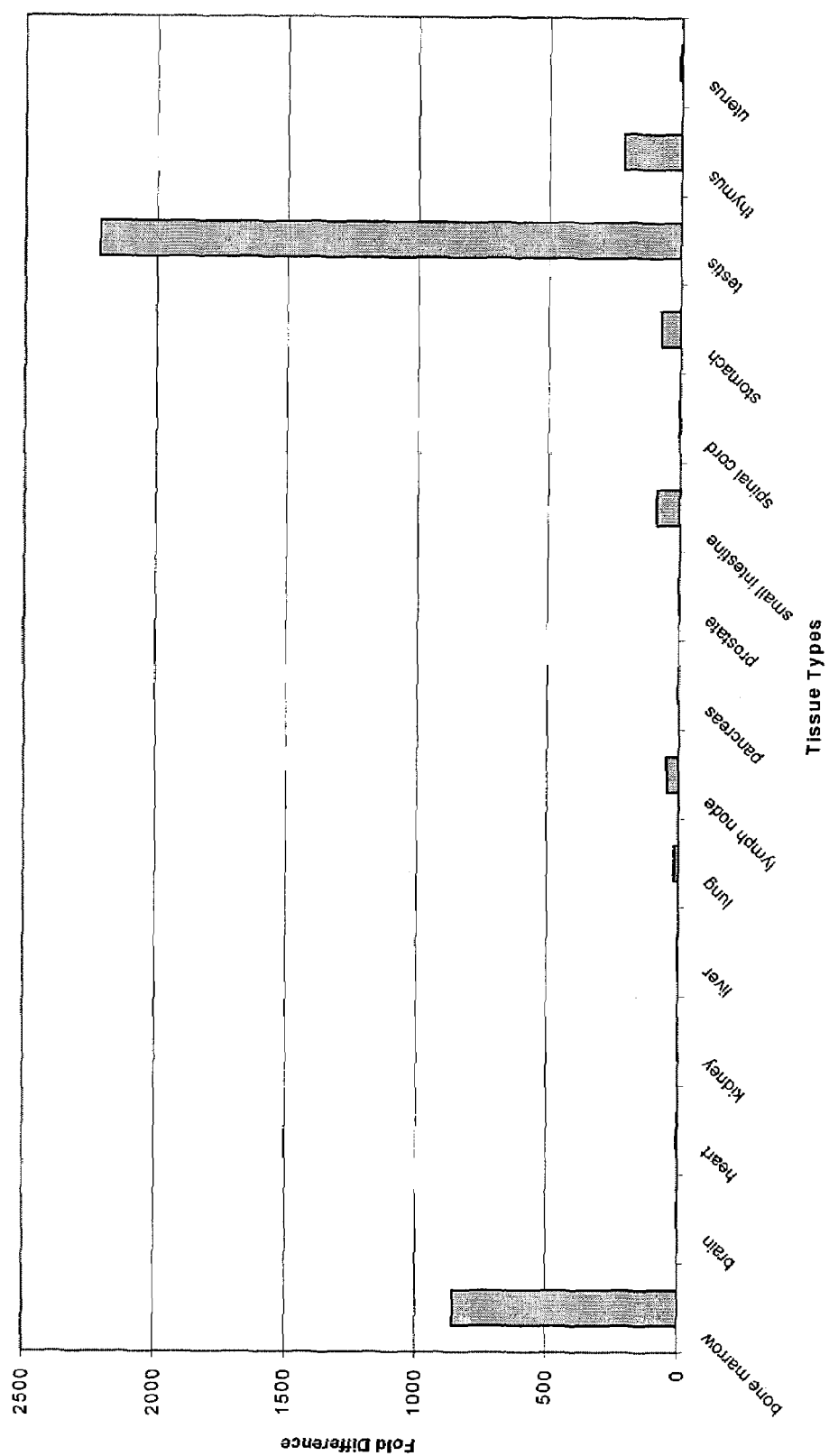
FIG. 8 shows expression profiling of the novel human protein kinase as expressed in various human adult tissues (with testis) using the Batch 2 primers of SEQ ID NOS: 66 and 67.
Figure 9:
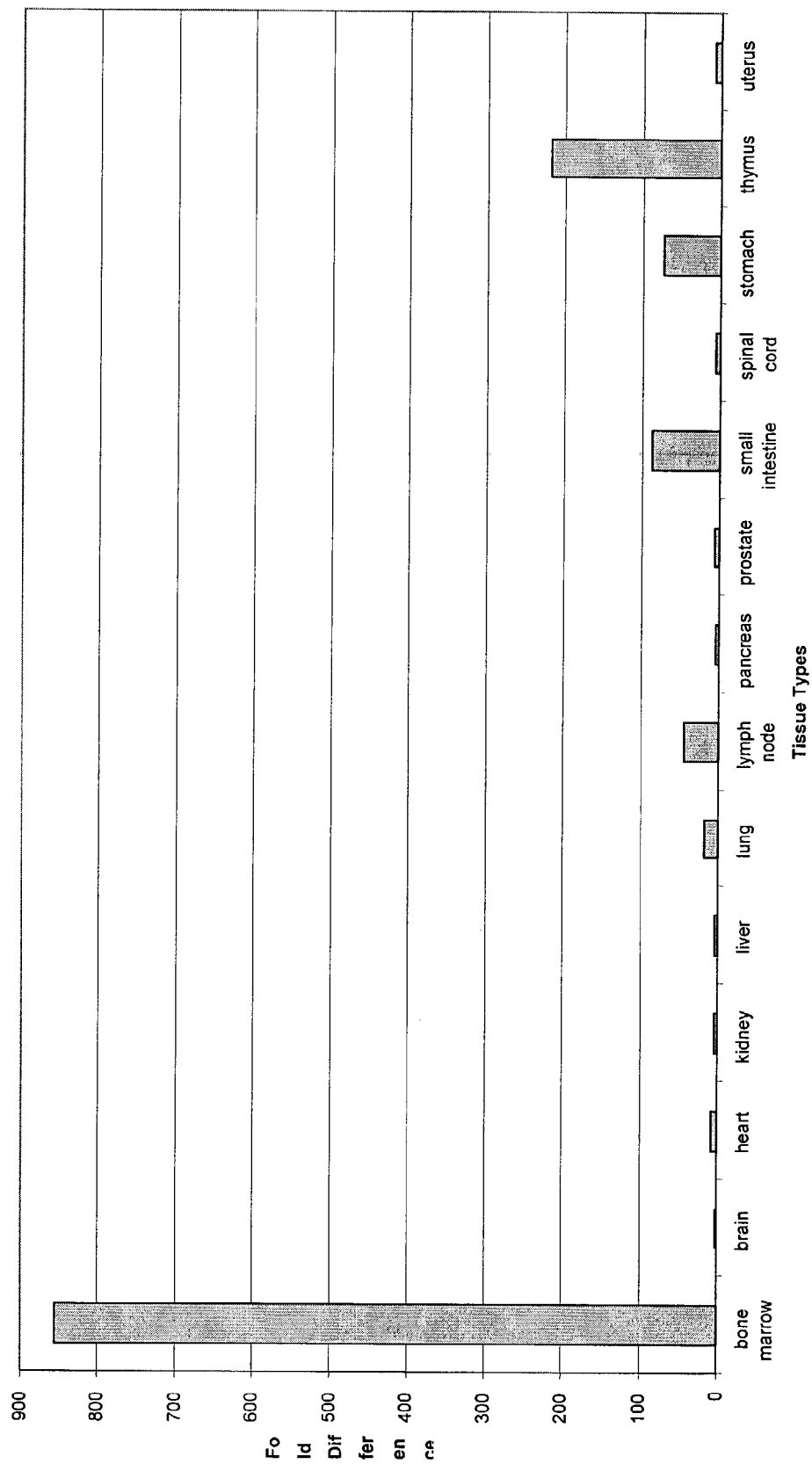
FIG. 9 shows expression profiling of the novel human protein kinase as expressed in various human adult tissues (without testis) using the Batch 2 primers of SEQ ID NOS: 66 and 67.
Figure 10:
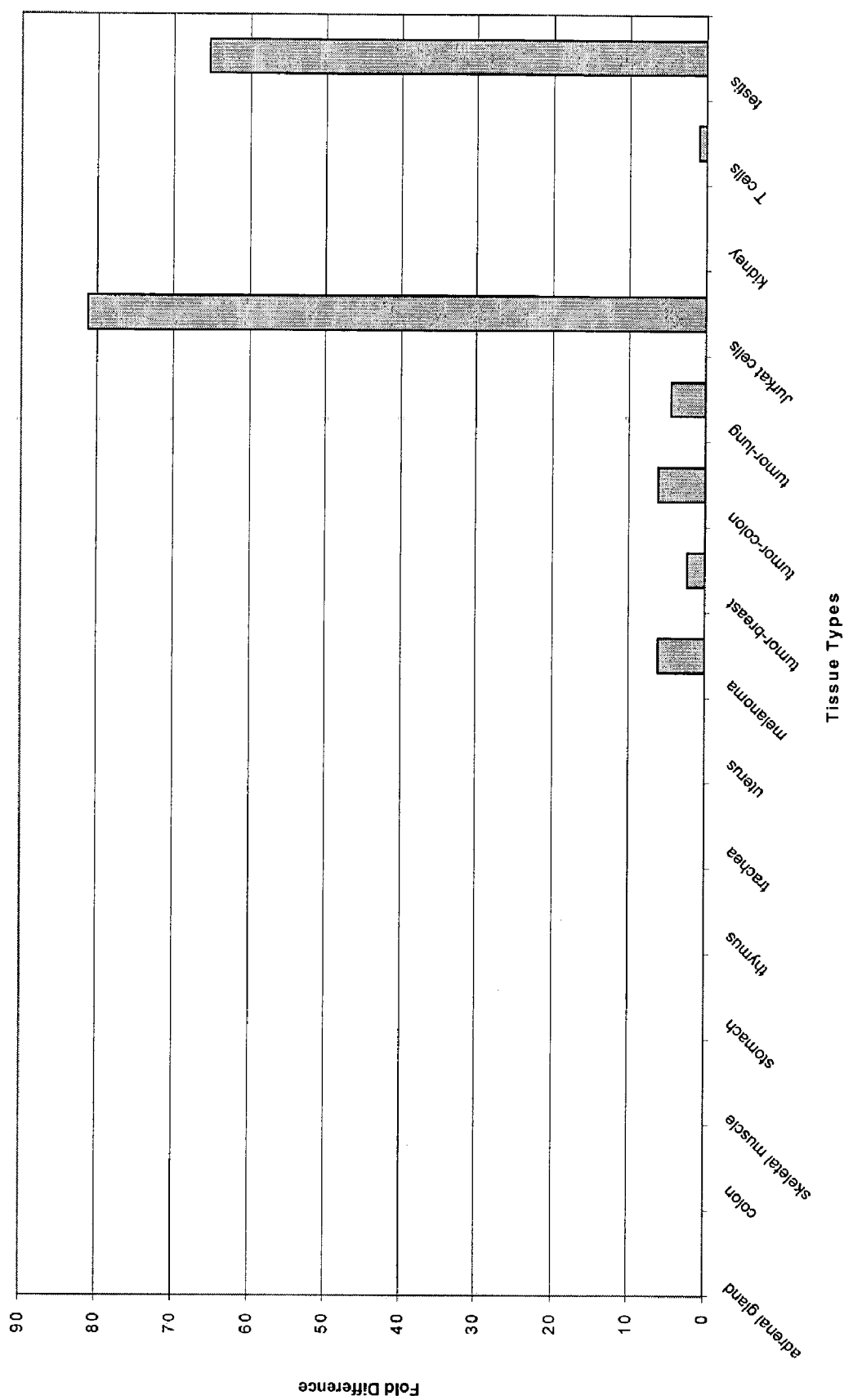
FIG. 10 shows expression profiling of the novel human protein kinase as expressed in various human adult cancerous and non-cancerous tissues using the Batch 1 primers of SEQ ID NOS: 64 and 65.
Figure 11:
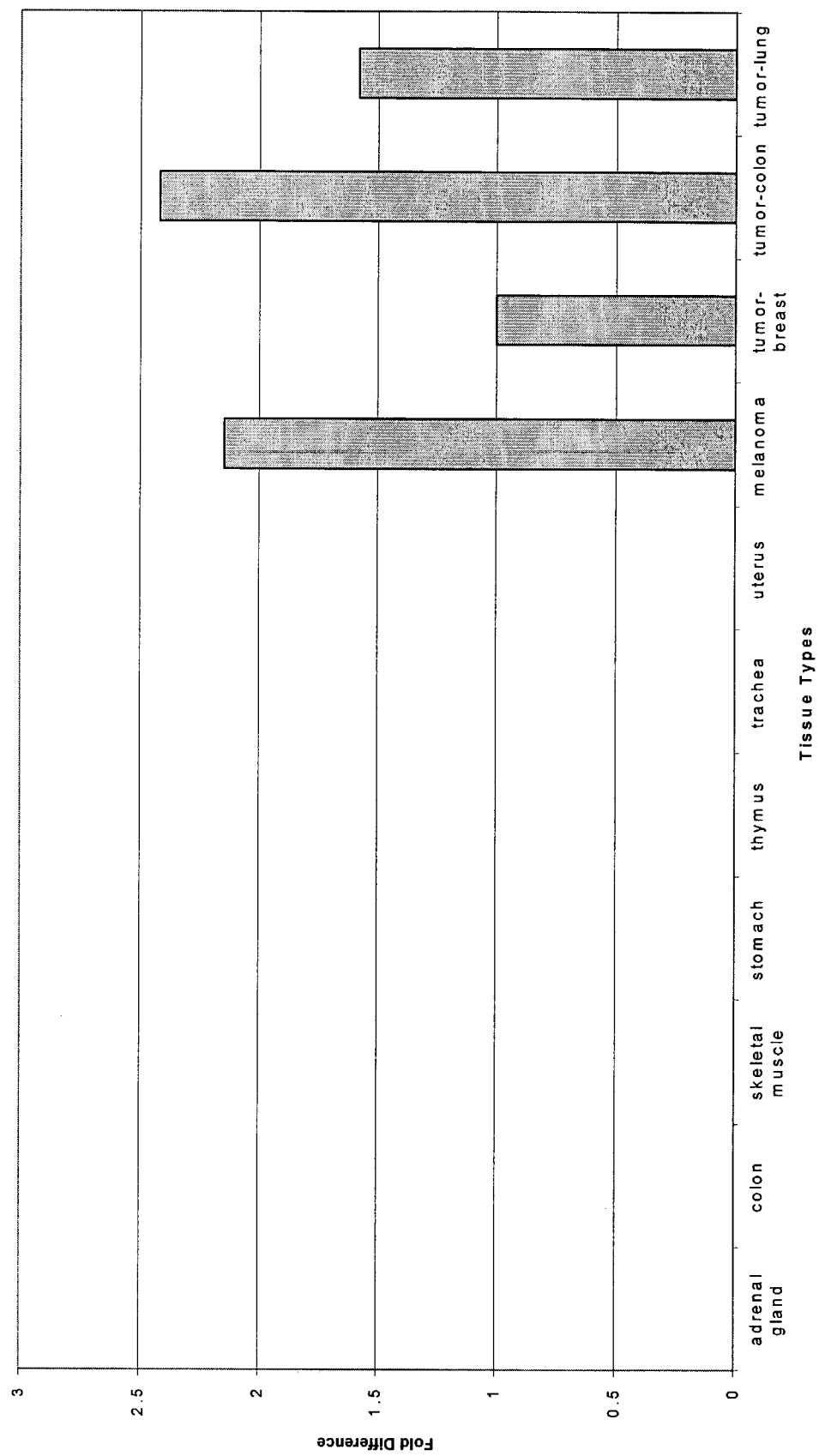
FIG. 11 shows expression profiling of the novel human protein kinase as expressed in various human adult cancerous and non-cancerous tissues (without Jurkat cells, kidney, T cells, and testis) using the Batch 1 primers of SEQ ID NOS: 64 and 65.
Figure 12:
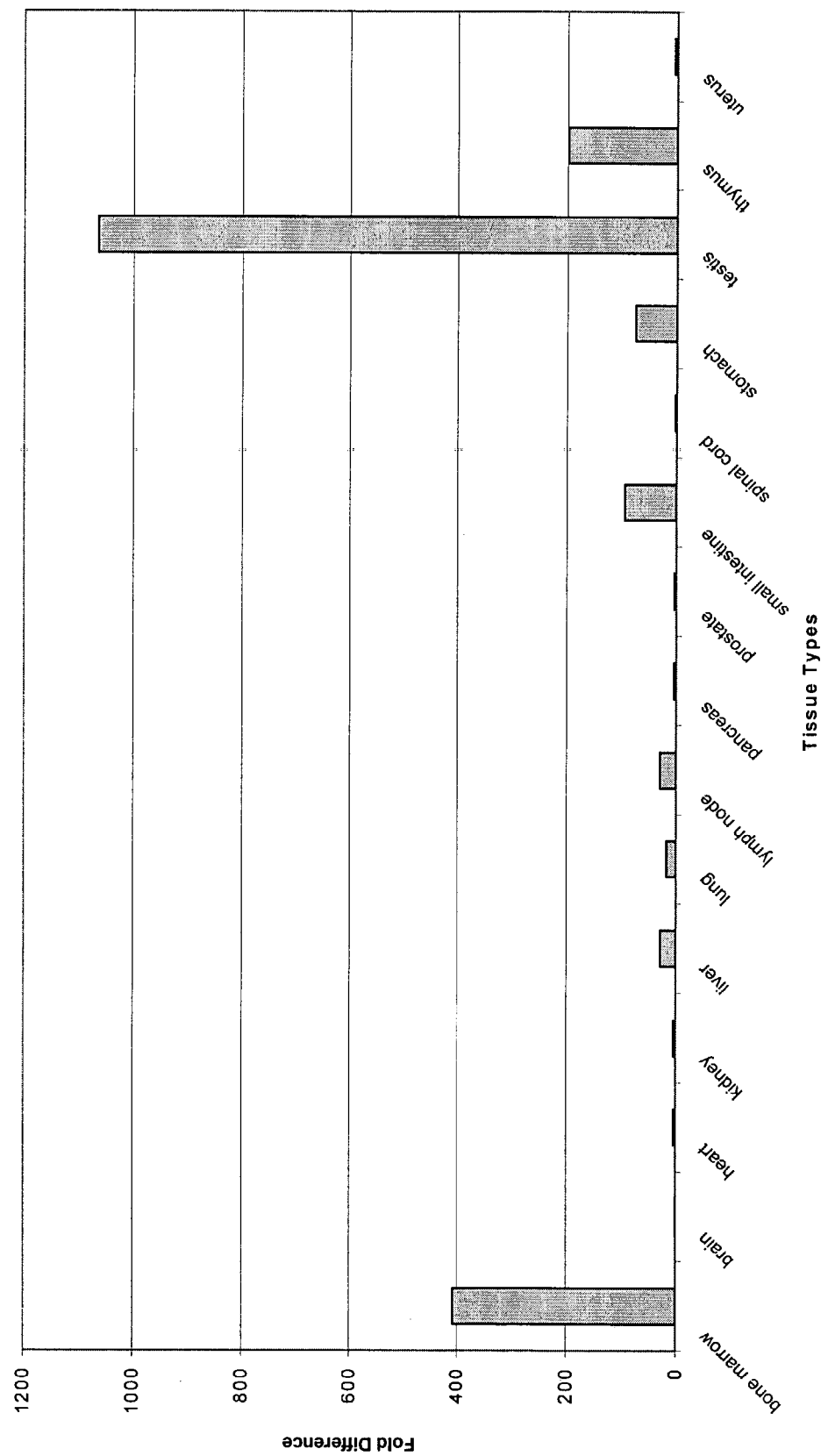
FIG. 12 shows expression profiling of the novel human protein kinase as expressed in various human adult tissues (with testis) using the Batch 1 primers of SEQ ID NOS: 64 and 65.
Figure 13:
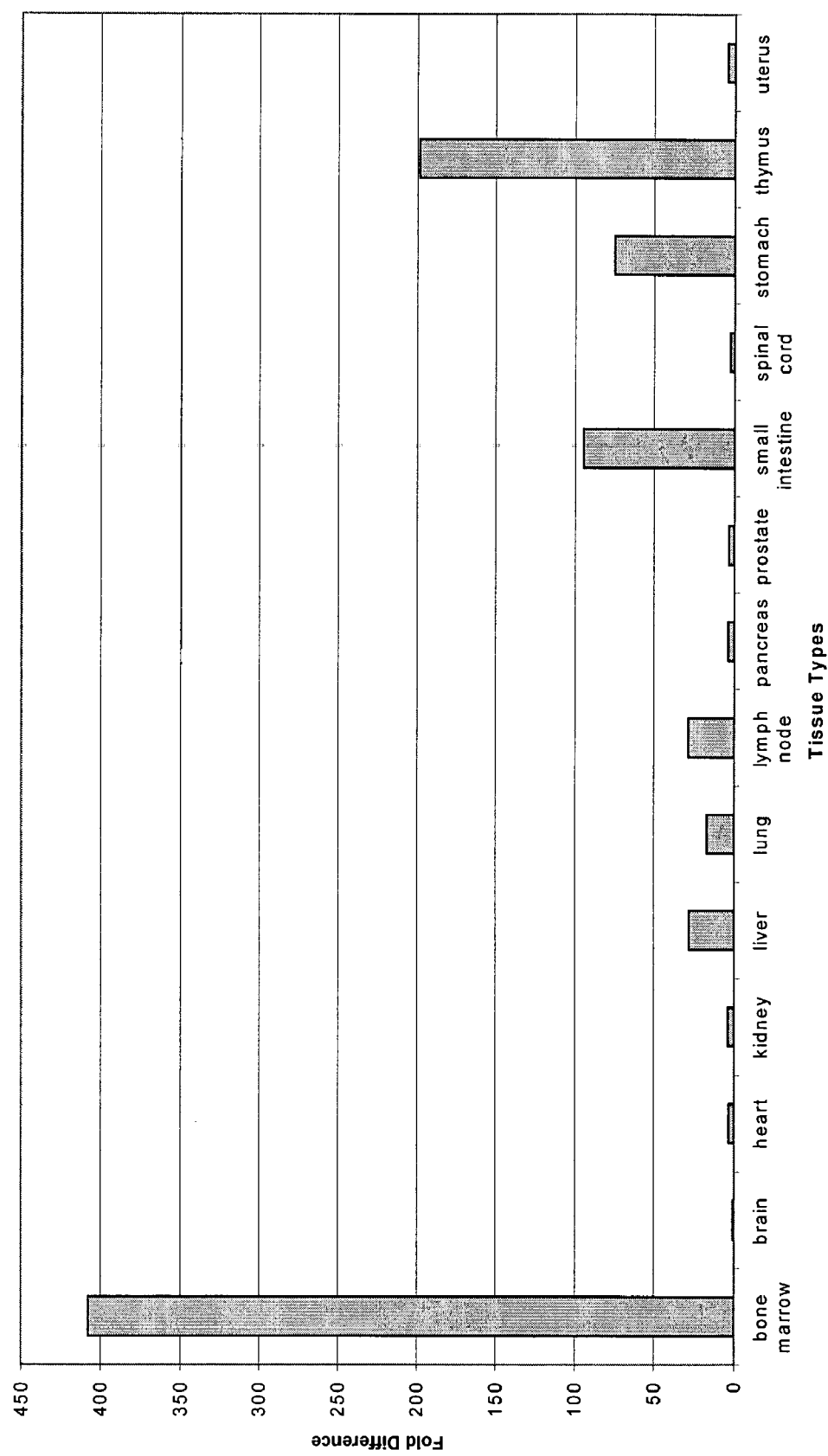
FIG. 13 shows expression profiling of the novel human protein kinase as expressed in various human adult tissues (without testis) using the Batch 1 primers of SEQ ID NOS: 64 and 65.

The present invention provides a new human protein kinase polynucleotide (nucleic acid) sequence which encodes a protein kinase polypeptide, preferably a full-length protein kinase polypeptide. In particular, the novel human protein kinase of the invention, also referred to herein as BMSNKC_0020/0021, is a citron kinase (CitK)-related protein kinase. The invention further relates to fragments and portions of the CitK-related nucleic acid sequence and its encoded amino acid sequence as described herein. Preferably, the fragments and portions of the protein kinase polypeptide are functional or active. The invention also provides methods of using the citron protein kinase polynucleotide sequence and its encoded polypeptide for genetic screening and for the treatment of diseases, disorders, conditions, or syndromes associated with protein kinase activity and function.

DEFINITIONS

The following definitions are provided to more fully describe the present invention in its various aspects. The definitions are intended to be useful for guidance and elucidation, and are not intended to limit the disclosed invention or its embodiments.

"Amino acid sequence" as used herein can refer to an oligopeptide, peptide, polypeptide, or protein sequence, and fragments or portions thereof, as well as to naturally occurring or synthetic molecules, preferably the isolated polypeptide of the protein kinase. Amino acid sequence fragments are typically from about 4 to about 30, preferably from about 5 to about 15, more preferably from about 5 to about 15 amino acids in length, but can include all amino acids except for one, and preferably retain the biological activity or function of a protein kinase polypeptide. The human CitK-related kinase, BMSNKC_0020/0021, amino acid sequence of this invention is set forth in SEQ ID NO:2 and in the description of the Figures. The terms "BMSNKC_0020/0021 polypeptide", "BMSNKC_0020/0021 protein", "citron kinase-related kinase polypeptide", and "citron kinase-related kinase protein" are used interchangeably herein to refer to the encoded product of the CitK-related kinase (BMSNKC_0020/0021) nucleic acid sequence according to the present invention.

An isolated CitK-related kinase polypeptide refers to the amino acid sequence of substantially purified protein kinase of this invention, which can be obtained from any species, preferably mammalian, such as, mice, rats, rabbits, sheep, goats, and more preferably, cats, dogs, monkeys, and apes, and most preferably humans, and from a variety of sources, including natural, synthetic, semi-synthetic, or recombinant. More particularly, the protein kinase polypeptide of this invention is identified in SEQ ID NO:2. Fragments of the CitK-related kinase (BMSNKC_0020/0021) polypeptide are also embraced by the present invention.

By a "kinase polypeptide" is meant 32, preferably 40, more preferably 45, and most preferably 55, or more contiguous amino acids in a polypeptide having an amino acid sequence seleted from SEQ ID NO:1. In certain aspects, a polypeptide of 100, 200, 300, 400, 450, or more amino acids is preferred. The kinase polypeptide can be encoded by a full-length nucleic acid sequence, as long as a functional activity of the polypeptide is retained, including, for example, a catalytic domain, as defined herein, or a portion thereof. One skilled in the art would be able to select those catalytic domains, or portions thereof, which exhibit a kinase or kinase-like activity, e.g., catalytic activity, as defined herein. It is well known in the art that due to the degeneracy of the genetic code numerous different nucleic acid sequences can code for the same amino acid sequence.

"Similar" amino acids are those which have the same or comparable physical properties and in many cases, the function is conserved with similar residues. For example, the amino acids lysine and arginine are similar; while residues such as proline and cysteine do not share any physical property and are not considered to be similar. Further information regarding making amino acid exchanges which have only slight, if any, effects on the overall protein can be found in Bowie et al., Science, 1990, 247, 1306-1310, which is incorporated herein by reference in its entirety including any figures, tables, or drawings. In all cases, all permutations are intended to be covered by this disclosure.

The term "consensus" refers to a sequence that reflects the most common choice of base or amino acid at each position among a series of related DNA, RNA or protein sequences. Areas of particularly good agreement often represent conserved functional domains.

A "variant" of a polypeptide refers to an amino acid sequence that is altered by one or more amino acids. The variant can have "conservative" changes, in which a substituted amino acid has similar structural or chemical properties, e.g., replacement of leucine with isoleucine. More rarely, a variant can have "non-conservative" changes, for example, replacement of a glycine with a tryptophan. The encoded protein can also contain deletions, insertions, or substitutions of amino acid residues, which produce a silent change and result in a functionally equivalent protein kinase protein. Deliberate amino acid substitutions can be made on the basis of similarity in polarity, charge, solubility, hydrophobicity, hydrophilicity, and/or the amphipathic nature of the residues, as long as the biological activity of the citron kinase-related kinase protein is retained. For example, negatively charged amino acids can include aspartic acid and glutamic acid; positively charged amino acids can include lysine and arginine; and amino acids with uncharged polar head groups having similar hydrophilicity values can include leucine, isoleucine, and valine; glycine and alanine; asparagine and glutamine; serine and threonine; and phenylalanine and tyrosine. Guidance in determining which amino acid residues can be substituted, inserted, or deleted without abolishing functional biological or immunological activity can be found using computer programs well known in the art, for example, DNASTAR, Inc. software (Madison, Wis.).

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

In addition, the present invention also encompasses the conservative substitutions provided below.

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

"Similarity" is measured by dividing the number of identical residues plus the number of conservatively substituted residues (Bowie, et al. (1999) Science. 247:1306-1310, incorporated herein by reference in its entirety, including any drawings, figures, or tables) by the total number of residues and gaps and multiplying the product by 100.

The term "mimetic", as used herein, refers to a molecule, having a structure which is developed from knowledge of the structure of a CitK-related kinase protein, or portions thereof, and as such, is able to affect some or all of the actions of the protein kinase protein. A mimetic can comprise a synthetic peptide or an organic molecule.

"Nucleic acid or polynucleotide sequence", as used herein, refers to an isolated oligonucleotide ("oligo"), nucleotide, or polynucleotide, and fragments thereof, and to DNA or RNA of genomic or synthetic origin which can be single- or double-stranded, and represent the sense or anti-sense strand, preferably of the protein kinase. By way of non-limiting examples, fragments include nucleic acid sequences that are greater than 20-60 nucleotides in length, and preferably include fragments that are at least 70-100 nucleotides, or which are at least 1000 nucleotides or greater in length. The protein kinase nucleic acid sequence of this invention is specifically identified in SEQ ID NO:1 and illustrated in FIG. 1.

An "allele" or "allelic sequence" is an alternative form of the protein kinase nucleic acid sequence of the invention. Alleles can result from at least one mutation in the protein kinase nucleic acid sequence and can yield altered mRNAs or a polypeptide whose structure or function may or may not be altered. Any given gene, whether natural or recombinant, can have none, one, or many allelic forms. Common mutational changes, which give rise to alleles, are generally ascribed to natural deletions, additions, or substitutions of nucleotides. Each of these types of changes can occur alone, or in combination with the others, one or more times in a given sequence.

"Peptide nucleic acid" (PNA) refers to an antisense molecule or anti-gene agent which comprises an oligonucleotide ("oligo") linked via an amide bond, similar to the peptide backbone of amino acid residues. PNAs typically comprise oligos of at least 5 nucleotides linked via amide bonds. PNAs may or may not terminate in positively charged amino acid residues to enhance binding affinities to DNA. Such amino acids include, for example, lysine and arginine, among others. These small molecules stop transcript elongation by binding to their complementary strand of nucleic acid (P. E. Nielsen et al., 1993, *Anticancer Drug Des.*, 8:53-63). PNA can be pegylated to extend their lifespan in the cell where they preferentially bind to complementary single stranded DNA and RNA.

"Oligonucleotides" or "oligomers" refer to a protein kinase nucleic acid sequence comprising contiguous nucleotides of at least about 5 nucleotides to about 60 nucleotides, preferably at least about 8 to 10 nucleotides in length, more preferably at least about 12 nucleotides in length, for example, about 15 to 35 nucleotides, or about 15 to 25 nucleotides, or about 20 to 35 nucleotides, which can be typically used in PCR amplification assays, hybridization assays, or in microarrays. It will be understood that the term oligonucleotide is substantially equivalent to the terms primer, probe, or amplimer, as commonly defined in the art.

The term "antisense" refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNAs and can be produced by any method, including synthesis or transcription. Once introduced into a cell, the complementary nucleotides combine with natural sequences produced by the cell to form duplexes, which block either transcription or translation. The designation "negative" is sometimes used in reference to the antisense strand, and "positive" is sometimes used in reference to the sense strand. Antisense oligonucleotides may be single or double stranded. Double stranded RNA's may be designed based upon the teachings of Paddison et al., Proc. Nat. Acad. Sci., 99:1443-1448 (2002); and International Publication Nos. WO 01/29058, and WO 99/32619; which are hereby incorporated herein by reference.

"Altered" nucleic acid sequences encoding a CitK-related kinase polypeptide include nucleic acid sequences containing deletions, insertions and/or substitutions of different nucleotides resulting in a polynucleotide that encodes the same or a functionally equivalent CitK-related kinase polypeptide. Altered nucleic acid sequences can further include polymorphisms of the polynucleotide encoding a protein kinase polypeptide; such polymorphisms may or may not be readily detectable using a particular oligonucleotide probe.

The term "Expressed Sequence Tag" or "EST" refers to the partial sequence of a cDNA insert which has been made by reverse transcription of mRNA extracted from a tissue, followed by insertion into a vector as commonly known in the art (Adams, M. D., et al. *Science* (1991) 252:1651-1656; Adams, M. D. et al., *Nature*, (1992) 355:632-634; Adams, M. D., et al., *Nature* (1995) 377 Supp:3-174).

The term "activates" refers to increasing the cellular activity of a kinase. The term "inhibit" refers to decreasing the cellular activity of a kinase, where kinase activity can be measured by phosphorylation of a substrate, activation of a protein, a change in the expression of genes that are up- or down-regulated in response to the protein kinase-dependent signal cascade.

The term "biologically active", i.e., functional, refers to a protein or polypeptide or fragment thereof, having structural, regulatory, or biochemical functions of a naturally occurring molecule. Likewise, "immunologically active" refers to the capability of a natural, recombinant, or synthetic protein kinase, or an oligopeptide thereof, to induce a specific immune response in appropriate animals or cells, for example, to generate antibodies, to bind with specific antibodies, and/or to elicit a cellular immune response.

The term "recombinant kinase polypeptide" is meant a polypeptide produced by recombinant DNA techniques such that it is distinct from a naturlly occuring polypeptide produced by recombinant DNA techniques and is distinct from a naturally occuring polypeptide either in its location (e.g. present in a different cell or tissue than found in nature), purity, or structure. The polypeptide to be expressed in host cells can also be a fusion protein which includes regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) can be fused in-frame to the polynucleotide sequence so that the polypeptide is translated as a fusion protein comprising the signal peptide.

A signal peptide that is functional in the intended host cell promotes extracellular secretion of the polypeptide. Preferably, the signal sequence can be cleaved from the polypeptide upon secretion of the polypeptide from the cell. Thus, preferred fusion proteins can be produced in which the N-terminus of a kinase polypeptide is fused to a carrier peptide. In one embodiment, the polypeptide comprises a fusion protein which includes a heterologous region used to facilitate purification of the polypeptide. Many of the available peptides used for such a function allow selective binding of the fusion protein to a binding partner. A preferred binding partner includes one or more of the IgG binding domains of protein A which are easily purified to homogeneity by affinity chromatography on, for example, IgG-coupled Sepharose. Alternatively, many vectors have the advantage of carrying a stretch of histidine residues that can be expressed, at the N-terminal or C-terminal end of the target protein, and thus the protein of interest can be recovered by metal chelation chromatography. A nucleotide sequence encoding a recognition site for a proteolytic enzyme such as enterokinase, factor X procollagenase or thrombin may immediately precede the sequence for a kinase polypeptide to permit cleavage of the fusion protein to obtain the mature kinase polypeptide. Additional examples of fusion-protein binding partners include, but are not limited to, the yeast I-factor, the honeybee melatin leader in sf9 insect cells, 6-His tag, thioredoxin tag, hemaglutinin tag, GST tag, and OmpA signal sequence tag. As will be understood by one of skill in the art, the binding partner which recognizes and binds to the peptide may be any ion, molecule or compound including metal ions (e.g., metal affinity columns), antibodies, or fragments thereof, and any protein or peptide which binds the peptide, such as the FLAG tag (DYKDDDDK; SEQ ID NO:73).

The term "modulates" refers to the ability of a compound to alter the activity or function of a kinase of the invention. A modulator preferably activates or inhibits the activity of a kinase of the invention depending on the concentration of the compound exposed to the kinase. The term "modulates" also refers to altering the function of kinases of the invention by increasing or decreasing the probability that a complex forms between the kinase and a natural binding partner depending on the concentration of the compound exposed to the kinase, and most preferably decreases the probability that a complex forms between the kinase and a natural binding partner.

An "agonist" refers to a molecule which, when bound to, or associated with, a protein kinase polypeptide, or a functional fragment thereof, increases or prolongs the duration of the effect of the protein kinase polypeptide. Agonists can include proteins, nucleic acids, carbohydrates, or any other molecules that bind to and modulate the effect of protein kinase polypeptide. Agonists typically enhance, increase, or augment the function or activity of a protein kinase molecule.

An "antagonist" refers to a molecule which, when bound to, or associated with, a protein kinase polypeptide, or a functional fragment thereof, decreases the amount or duration of the biological or immunological activity of protein kinase polypeptide. Antagonists can include proteins, nucleic acids, carbohydrates, antibodies, or any other molecules that decrease or reduce the effect of a protein kinase polypeptide. Antagonists typically, diminish, inhibit, or reduce the function or activity of a protein kinase molecule.

The term "complementary" or "complementarity" refers to the natural binding of polynucleotides under permissive salt and temperature conditions by base pairing. For example, the sequence "A-G-T" binds to the complementary sequence "T-C-A". Complementarity between two single-stranded molecules can be "partial", in which only some of the nucleic acids bind, or it can be "complete" when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term "homology" refers to a degree of complementarity. There can be partial homology or complete homology, wherein complete homology is equivalent to identity. A partially complementary sequence that at least partially inhibits an identical sequence from hybridizing to a target nucleic acid is referred to as the functional term "substantially homologous". The inhibition of hybridization of the completely complementary sequence to the target sequence can be examined using a hybridization assay (for example, Southern or Northern blot, solution hybridization, and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding can be tested by the use of a second target sequence which lacks even a partial degree of complementarity (for example, less than about 25-30% identity). In the absence of non-specific binding, the probe will not hybridize to the second non-complementary target sequence.

Those having skill in the art will know how to determine percent identity between/among sequences using, for example, algorithms such as those based on the CLUSTALW computer program (J. D. Thompson et al., 1994, *Nucleic Acids Research*, 2(22):4673-4680), or FASTDB, (Brutlag et al., 1990, *Comp. App. Biosci.*, 6:237-245), as commonly known in the art. Although the FASTDB algorithm typically does not consider internal non-matching deletions or additions in sequences, i.e., gaps, in its calculation, this can be corrected manually to avoid an overestimation of the percent identity. CLUSTALW, however, does take sequence gaps into account in its identity calculations.

The present invention is also directed to polynucleotide sequences which comprise, or alternatively consist of, a polynucleotide sequence which is at least about 80%, 85%, 90%, 90.8%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a BMSNKC_0020/0021 related polypeptide having an amino acid sequence as shown in the sequence listing and described herein; (b) a nucleotide sequence encoding a mature BMSNKC_0020/0021 related polypeptide having the amino acid sequence as shown in the sequence listing and described herein; (c) a nucleotide sequence encoding a biologically active fragment of a BMSNKC_0020/0021 related polypeptide having an amino acid sequence as shown in the sequence listing and described herein; (d) a nucleotide sequence encoding an antigenic fragment of a BMSNKC_0020/0021 related polypeptide having an amino acid sequence as shown in the sequence listing and described herein; (e) a nucleotide sequence encoding a BMSNKC_0020/0021 related polypeptide having an comprising the complete amino acid sequence encoded by a human cDNA described herein; (f) a nucleotide sequence encoding a mature BMSNKC_0020/0021 related polypeptide having an amino acid sequence encoded by a human cDNA described herein: (g) a nucleotide sequence encoding a biologically active fragment of a BMSNKC_0020/0021 related polypeptide having an amino acid sequence encoded by a human cDNA described herein; (h) a nucleotide sequence encoding an antigenic fragment of a BMSNKC_0020/0021 related polypeptide having an amino acid sequence encoded by a human cDNA and described herein; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 90.8%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 90.4%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 90.4%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, a polypeptide sequence encoded by the nucleotide sequence in SEQ ID NO:1, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced herein, the ORF (open reading frame), or any fragment specified as described herein.

As a practical matter, whether any particular nucleic acid molecule or polypeptide is at least about 80%, 85%, 90%, 90.4%, 90.8%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 90.4%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both amino acid sequences. The result of said global sequence alignment is in percent identity. Preferred parameters used in a CLUSTALW alignment of polypeptide sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

Also available to those having skill in this art are the BLAST and BLAST 2.0 algorithms (Altschul et al., 1977, *Nuc. Acids Res.*, 25:3389-3402 and Altschul et al., 1990, *J. Mol. Biol.*, 215:403-410). The BLASTN program for nucleic acid sequences uses as defaults a wordlength (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff & Henikoff, 1989, *Proc. Natl. Acad. Sci., USA*, 89:10915) uses alignments (B) of 50, expectation (E) of 10, M=5, N=4, and a comparison of both strands.

The term "complex" refers to an assembly of at least two molecules bound to one another. Signal transduction complexes often contain at least two protein molecules bound to one another. For example, a protein tyrosine receptor protein kinase, Grb2, SOS, Raf, and Ras assemble to form a signal transduction complex in response to a mitogenic ligand.

The term "natural binding partner" refers to polypeptides, lipids, small molecules, or nucleic acids that bind to kinases in cells. A change in the interaction between a kinase and a natural binding partner can manifest itself as an increased or decreased probability that the interaction forms, or an increased or decreased concentration of kinase or natural binding partner complex.

"Contacting" as used herein refers to mixing a solution comprising the test compound with a liquid medium bathing the cells of the methods. The solution comprising the compound can also comprise at least one other component, such as dimethyl sulfoxide (DMSO), which facilitates the uptake of the test compound or compounds into the cells of the methods. The solution comprising the test compound can be added to the medium bathing the cells by utilizing a delivery apparatus, such as a pipette-based device or syringe-based device.

The term "hybridization" refers to any process by which a strand of nucleic acids binds with a complementary strand through base pairing. The term "hybridization complex" refers to a complex formed between two nucleic acid sequences by virtue of the formation of hydrogen bonds between complementary G and C bases and between complementary A and T bases. The hydrogen bonds can be further stabilized by base stacking interactions. The two complementary nucleic acid sequences hydrogen bond in an anti-parallel configuration. A hybridization complex can be formed in solution (for example, $C_o t$ or $R_o t$ analysis), or between one nucleic acid sequence present in solution and another nucleic acid sequence immobilized on a solid phase or support (for example, membranes, filters, chips, pins, or glass slides, or any other appropriate substrate to which cells or their nucleic acids have been affixed).

The term "stringency" or "stringent conditions" refers to the conditions for hybridization as defined by nucleic acid composition, salt, and temperature. These conditions are well known in the art and can be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (for example, formamide, dextran sulfate and/or polyethylene glycol) and reaction temperature (within a range of from about 5° C. below the melting temperature of the probe to about 20° C. to 25° C. below the melting temperature). One or more factors can be varied to generate conditions, either low or high stringency that is different from but equivalent to the aforementioned conditions.

As will be understood by those of skill in the art, the stringency of hybridization can be altered in order to identify or detect identical or related polynucleotide sequences. As will be further appreciated by the skilled practitioner, the melting temperature, $T_m$, can be approximated by the formulas as well known in the art, depending on a number of parameters, such as the length of the hybrid or probe in number of nucleotides, or hybridization buffer ingredients and conditions (see, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-2.10.16; G. M. Wahl and S. L. Berger (1987; *Methods Enzymol.* 152:399-407); and A. R. Kimmel, 1987; *Methods of Enzymol.* 152:507-511).

As a general guide, $T_m$ decreases approximately 1° C.-1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, for example, high, moderate, or low stringency, typically relates to such washing conditions. It is to be understood that the low, moderate and high stringency hybridization or washing conditions can be varied using a variety of ingredients, buffers and temperatures well known to and practiced by the skilled artisan.

A "composition" refers broadly to any composition comprising the novel protein kinase polynucleotide, polypeptide, derivative, or mimetic thereof, or antibodies thereto. The composition can comprise a dry formulation or an aqueous solution. Compositions comprising the protein kinase polynucleotide sequence of SEQ ID NO:1 encoding the protein kinase polypeptide of SEQ ID NO:2, or fragments thereof, can be employed as hybridization probes. The probes can be stored in a freeze-dried form and can be in association with a stabilizing agent such as a carbohydrate. In hybridizations, the probe can be employed in an aqueous solution containing salts (for example, NaCl), detergents or surfactants (for example, SDS) and other components (for example, Denhardt's solution, dry milk, salmon sperm DNA, and the like).

The term "substantially purified" refers to nucleic acid sequences or amino acid sequences that are removed from their natural environment, isolated or separated, and are at least 60% free, preferably 75% to 85% free, and most preferably 90% to 95%, or greater, free from other components with which they are naturally associated.

The term "sample", or "biological sample", is meant to be interpreted in its broadest sense. A non-limiting example of a biological sample suspected of containing a protein kinase nucleic acid encoding protein kinase protein, or fragments thereof, or a protein kinase protein itself, can comprise, but is not limited to, a body fluid, an extract from cells or tissue, chromosomes isolated from a cell (for example, a spread of metaphase chromosomes), organelle, or membrane isolated from a cell, a cell, nucleic acid such as genomic protein kinase DNA (in solution or bound to a solid support such as, for example, for Southern analysis), protein kinase RNA (in solution or bound to a solid support such as for Northern analysis), protein kinase cDNA (in solution or bound to a solid support), a tissue, a tissue print, and the like.

The term "correlates with expression of a polynucleotide" indicates that the detection of the presence of ribonucleic acid that is similar to the nucleic acid sequence of the protein kinase of the invention by Northern analysis is indicative of the presence of mRNA encoding the protein kinase polypeptide of SEQ ID NO:2 in a sample and thereby correlates with expression of the transcript from the polynucleotide encoding the protein.

An alteration in the polynucleotide of SEQ ID NO:1 comprises any alteration in the sequence of the polynucleotides encoding the protein kinase polypeptide, including deletions, insertions, and point mutations that can be detected using hybridization assays. Included within this definition is the detection of alterations to the genomic DNA sequence which encodes the protein kinase polypeptide (e.g., by alterations in the pattern of restriction fragment length polymorphisms capable of hybridizing to the nucleic acid sequence of SEQ ID NO:1), the inability of a selected fragment of SEQ ID NO:1 to hybridize to a sample of genomic DNA (e.g., using allele-specific oligonucleotide probes), and improper or unexpected hybridization, such as hybridization to a locus other than the normal chromosomal locus for the polynucleotide sequence encoding the protein kinase polypeptide (e.g., using fluorescent in situ hybridization (FISH) to metaphase chromosome spreads).

The term "antibody" refers to intact molecules which are capable of binding an epitopic or antigenic determinant. The term "antibody fragment" refers to a portion of an antibody, often the hypervariable region and portions of the surrounding heavy and light chains, such as Fab, $F(ab')_2$, Fv, that displays specific binding affinity for a particular molecule. A hypervariable region is a portion of an antibody that physically binds to the polypeptide target. Antibodies can be used to identify an endogenous source of kinase polypeptides, to monitor cell cycle regulation, and for immuno-localization of kinase polypeptides within the cell.

An antibody or antibody fragment with specific binding affinity to the protein kinase polypeptide of the invention can be isolated, enriched, or purified from a prokaryotic or eukaryotic organism. Routine methods known to those skilled in the art enable the production of antibodies or antibody fragments in both types of organisms. Further, antibodies that bind to the protein kinase polypeptide can be prepared using intact polypeptides or fragments containing small peptides of interest or prepared recombinantly for use as the immunizing antigen. The polypeptide or oligopeptide used to immunize an animal can be derived from RNA translation of SEQ ID NO:1 or synthesized chemically, and can be conjugated to a carrier protein, if desired. Commonly used carriers that are chemically coupled to peptides include, but are not limited to, bovine serum albumin (BSA), keyhole limpet hemocyanin (KLH), and thyroglobulin. The coupled peptide is then used to immunize the animal (for example, a mouse, a rat, or a rabbit).

Antibodies having specific binding affinity to the protein kinase polypeptide of this invention can be used in methods for detecting the presence and/or amount of the protein kinase polypeptide in a sample by contacting the sample with the antibody under conditions such that an immunocomplex forms; and detecting the presence and/or amount of the antibody conjugated to the kinase polypeptide. Diagnostic kits for performing such methods can be constructed to include a first container having the antibody and a second container having a conjugate of a binding partner of the antibody and a detectable label, such as for example, a radioisotope or fluorescent molecule. The diagnostic kit can also include notification of an FDA approved use and instructions therefor.

A hybridoma according to the invention produces an antibody having specific binding affinity to the protein kinase polypeptide or a domain within the kinase polypeptide, where the polypeptide has an amino acid sequence as set forth in SEQ ID NO:2. By "hybridoma" is meant an immortalized cell line that is capable of secreting an antibody, for example, an antibody directed to the kinase of the invention. In preferred embodiments, the antibody to the kinase comprises a sequence of amino acids that is able to specifically bind to an epitope or epitopic region of the kinase polypeptide of the invention.

The term "humanized" antibody refers to antibody molecules in which amino acids have been replaced in the non-antigen binding regions (i.e., framework regions) of the immunoglobulin in order to more closely resemble a human antibody, while still retaining the original binding capability, for example, as described in U.S. Pat. No. 5,585,089 to C. L. Queen et al. In the present instance, humanized antibodies are preferably anti-protein kinase specific antibodies.

The term "antigenic determinant" refers to that portion of a molecule that makes contact with a particular antibody (i.e., an epitope). When a protein or fragment of a protein, preferably the protein kinase protein, or peptides thereof, is used to immunize a host animal, numerous regions of the protein can induce the production of antibodies which bind specifically to a given region or three-dimensional structure on the protein; these regions or structures are referred to as antigenic determinants or epitopes. An antigenic determinant can compete with the intact antigen (i.e., the immunogen used to elicit the immune response) for binding to an antibody.

In yet another aspect, the present invention is also directed to kits comprising antibodies that bind to a polypeptide encoded by any one of the nucleic acid molecules of SEQ ID NO:1, and a negative control antibody, which refers to an antibody derived from a similar source as the antibody having specific binding affinity, but does not display binding affinity to the polypeptide of the invention.

The term "specific binding" or "specifically binding" refers to the interaction between a protein or peptide, preferably the protein kinase protein described herein, and a binding molecule, such as an agonist, an antagonist, or an antibody. The interaction is dependent upon the presence of a particular structure (i.e., an antigenic determinant or epitope) of the protein that is recognized by the binding molecule.

DETAILED DESCRIPTION OF THE INVENTION

One embodiment of the present invention features a kinase polypeptide binding agent able to bind to the novel kinase polypeptide having the amino acid sequence as set forth in SEQ ID NO:2. The binding agent is preferably a purified antibody that recognizes an epitope present on the kinase polypeptide of the invention. Other binding agents include molecules that bind to kinase polypeptides and analogous molecules that bind to a kinase polypeptide. Such binding agents can be identified using assays that measure the kinase binding partner activity, such as those that measure platelet-derived growth factor receptor (PDGFR) activity.

In a further embodiment, methods of identifying compounds that bind to the kinase polypeptide of the present invention comprise of contacting the kinase polypeptide with a compound, and determining whether the compound binds to the kinase polypeptide. For example, examining the ability to bind or be activated by chemically synthesized peptide ligands, metal ions such as calcium, hormones, chemokines, neuropeptides, neurotransmitters, nucleotides, lipids, odorants, and photons. Binding can be determined by binding assays which are well known to the skilled artisan, including, but not limited to, gel-shift assays, Western blots, radiolabeled competition assays, phage-based expression cloning, co-fractionation by chromatography, co-precipitation, cross-linking, interaction trap/two-hybrid analysis, southwestern analysis, ELISAs, and the like, which are described in, for example, Ausbel et al., *Current Protocols in Molecular Biology*, 1999, John Wiley and Sons, NY, N.Y. which is incorporated herein by reference in its entirety. The assay can take the form of a yeast growth assay, an Aequorin assay, a Luciferase assay, a mitogenesis assay, a MAP Kinase activity assay, as well as other binding or function-based assays of kinase activity that are generally known in the art. The compounds to be screened include, but are not limited to, compounds of extracellular, intracellular, biological or chemical origin.

The methods of the invention also embrace compounds that are attached to a label, such as a radiolabel (for example, $^{125}$I, $^{32}$P, $^{33}$P, $^{3}$H), a fluorescent label, a chemiluminescent label, an enzymatic label and an immunogenic label. The kinase polypeptide employed in such a test can either be free in solution, attached to a solid support, borne on a cell surface, located intracellularly, or associated with a portion of a cell. One skilled in the art can, for example, measure the formation of complexes between the kinase polypeptide and the compound being tested. Alternatively, the skilled artisan can examine the decrease in complex formation between the kinase polypeptide and its substrate caused by the compound being tested.

Other assays that can be used to examine enzymatic activity include, but are not limited to, photometric, radiometric, HPLC, electrochemical, and the like, which are described in, for example, *Enzyme Assays: A Practical Approach*, eds. R. Eisenthal and M. J. Danson, 1992, Oxford University Press, incorporated herein by reference in its entirety. A further method for identifying ligands of a target protein is described by Wieboldt et al. (*Anal. Chem.* 69:1683-1691, 1997). This technique screens combinatorial libraries of 20-30 agents at a time in solution phase for binding to the target protein.

Another embodiment of the invention features methods for screening for human cells containing the kinase polypeptide of the invention or an equivalent sequence. The method involves identifying the novel polypeptide in human cells using techniques that are routine and standard in the art, such as those described herein for identifying the kinase of the invention (for example, cloning, Southern or Northern blot analysis, in situ hybridization, PCR amplification, etc.).

The human protein kinase polynucleotide and encoded protein kinase polypeptide of this invention are preferably full-length. More specifically, serine-threonine kinases can include sensory protein kinases, chemokine protein kinases, orphan protein kinases, and very large protein kinases. Protein kinases can also include CitK: Citron Kinase: DM, myotonic dystrophy kinase; PsPK5: Pisum sativum protein kinase 5; SGK1: Serum and glucocorticoid-regulated kinase; COT-1, COUP transcription factor 1 (also called COUP-TF1, COUP-TF I, and V-ERBA related protein EAR-3); MAST250: Microtubule-associated Kinase; ATPK5: *Arabidopsis thaliana* protein kinase 5; ATPK64: *Arabidopsis thaliana* Protein kinase 64; ATPK67: *Arabidopsis thaliana* protein kinase 67, and EGFR kinase: Epidermal Growth Factor receptor kinase.

The protein kinase polynucleotide and/or polypeptide of the invention are useful for diagnosing diseases related to over- or under-expression of the protein kinase polynucleotide and/or protein. For example, protein kinase-associated diseases can be assessed by identifying mutations in the protein kinase gene of the invention using protein kinase probes or primers, or by determining the protein kinase protein or mRNA expression levels. The protein kinase polypeptide of the invention, or peptides thereof, is also useful for screening compounds which affect activity of the protein. The invention further encompasses the polynucleotide encoding the protein kinase polypeptides and the use of the protein kinase polynucleotide or polypeptide, or compositions thereof, in the screening, diagnosis, treatment, or prevention of disorders associated with aberrant or uncontrolled cellular growth and/or function, such as neoplastic diseases (for example, cancers and tumors).

CitK-related protein kinase probes or primers can be used, for example, to screen for diseases associated with the protein kinase of the invention. Predicted left, right, and internal primers, can be determined from the disclosed protein kinase nucleic acid sequence of SEQ ID NO:1, and disclosed in Tables 2-4. One program for designing appropriate primers is the primer3 program (Steve Rozen, Helen J. Skaletsky (1996, 1997) Primer3.

Another embodiment of the present invention encompasses the novel human protein kinase polypeptide comprising the amino acid sequence of SEQ ID NO:2. Additionally, the kinase polypeptide comprises an amino acid sequence having an amino acid sequence of SEQ ID NO:2, except that it lacks one or more of the domains selected from the group consisting of a C-terminal catalytic domain, an N-terminal domain, a catalytic domain, a C-terminal domain, a coiled-coil structure region, a proline-rich region, a spacer region, and a C-terminal tail. Variants of the human protein kinase polypeptide are also encompassed by the present invention. Preferably, the human protein kinase variant has at least 75 to 80%, more preferably at least 85 to 90%, and even more preferably at least 90% amino acid sequence identity to the protein kinase amino acid sequence disclosed herein, and more preferably, retains at least one biological, immunological, or other functional characteristic or activity of the non-variant protein kinase polypeptide. Most preferred are protein kinase variants or substantially purified fragments thereof having at least 95% amino acid sequence identity to SEQ ID NO:2. Variants of human protein kinase polypeptides or substantially purified fragments of the polypeptides can also include amino acid sequences that differ from the SEQ ID NO:2 amino acid sequence only by conservative substitutions. The invention also encompasses polypeptide homologues and recombinant kinase polypeptides of the amino acid sequence as set forth in SEQ ID NO:2.

In another embodiment, the present invention encompasses polynucleotides which encode the protein kinase polypeptide as described and shown in SEQ ID NO:2. Accordingly, any nucleic acid sequence that encodes the amino acid sequence of the protein kinase polypeptide of the invention can be used to produce recombinant molecules that express the protein kinase protein. More particularly, the invention encompasses the protein kinase polynucleotide comprising the nucleic acid sequence of SEQ ID NO:1.

As will be appreciated by the skilled practitioner in the art, the degeneracy of the genetic code results in many nucleotide sequences that can encode the described protein kinase polypeptide. Some of the sequences bear minimal or no homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of naturally occurring protein kinase, and all such variations are to be considered as being specifically disclosed and able to be understood by the skilled practitioner.

Although nucleic acid sequences which encode the protein kinase polypeptide and variants thereof are preferably capable of hybridizing to the nucleotide sequence of the naturally occurring protein kinase polypeptide under appropriately selected conditions of stringency, it can be advantageous to produce nucleotide sequences encoding the protein kinase polypeptide, or derivatives thereof, which possess a substantially different codon usage. For example, codons can be selected to increase the rate at which expression of the peptide/polypeptide occurs in a particular prokaryotic or eukaryotic host in accordance with the frequency with which particular codons are utilized by the host. Another reason for substantially altering the nucleotide sequence encoding a protein kinase polypeptide, or its derivatives, without altering the encoded amino acid sequences, includes the production of RNA transcripts having more desirable properties, such as a greater half-life, than transcripts produced from the naturally occurring sequence.

The present invention also encompasses the production of DNA sequences, or portions thereof, which encode the protein kinase polypeptide, or derivatives thereof, entirely by synthetic chemistry. After production, the synthetic sequence can be inserted into any of the many available expression vectors and cell systems using reagents that are well known and practiced by those in the art. Moreover, synthetic chemistry can be used to introduce mutations into the sequence encoding a protein kinase polypeptide, or any fragment thereof.

In an embodiment of the present invention, a gene delivery vector containing the protein kinase polynucleotide, or functional fragment thereof is provided. Preferably, the gene delivery vector contains the polynucleotide, or functional fragment thereof, comprising an isolated and purified polynucleotide encoding the human protein kinase having the sequence as set forth in SEQ ID NO:1.

It will also be appreciated by those skilled in the pertinent art that in addition to the primers disclosed in Tables 2-3 herein, and oligonucleotides in Example 3, a longer oligonucleotide probe, or mixtures of probes, for example, degenerate probes, can be used to detect longer, or more complex, nucleic acid sequences, such as, for example, genomic or full length DNA. In such cases, the probe can comprise at least 20-300 nucleotides, preferably, at least 30-100 nucleotides, and more preferably, 50-100 nucleotides. Specifically, Tables 2 and 3 present single exon primers and multiple exon primers for BMSNKC_0020/0021; capture oligos for BMSNKC_0020/0021 are presented in Example 3.

The present invention also provides methods of obtaining the full length sequence of the CitK-related protein kinase polypeptide as described herein. In one instance, the method of multiplex cloning was devised as a means of extending large numbers of bioinformatic gene predictions into full length sequences by multiplexing probes and cDNA libraries in an effort to minimize the overall effort typically required for cDNA cloning. The method relies on the conversion of plasmid-based, directionally cloned cDNA libraries into a population of pure, covalently-closed, circular, single-stranded molecules and long biotinylated DNA oligonucleotide probes designed from predicted gene sequences.

Probes and libraries are subjected to solution hybridization in a formamide buffer which has been found to be superior to aqueous buffers typically used in other biotin/ streptavidin cDNA capture methods (i.e., GeneTrapper). The hybridization is performed without prior knowledge of the clones represented in the libraries. Hybridization is performed two times. After the first selection, the isolated sequences are is screened with PCR primers specific for the targeted clones. The second hybridization is carried out with only those oligo probes whose gene-specific PCR assays give positive results.

The secondary hybridization serves to 'normalize' the selected library, thereby decreasing the amount of screening needed to identify particular clones. The method is robust and sensitive. Typically, dozens of cDNAs are isolated for any one particular gene, thereby increasing the chances of obtaining a full length cDNA. The entire complexity of any cDNA library is screened in the solution hybridization process, which is advantageous for finding rare sequences. The procedure is scaleable, with 50 oligonucleotide probes per experiment currently being used, although this is not to be considered a limiting number.

Using bioinformatic predicted gene sequence, the following types of PCR primers and cloning oligos can be designed: (A) PCR primer pairs that reside within a single predicted exon; (B) PCR primer pairs that cross putative exon/intron boundaries; and (C) 80 mer antisense and sense oligos containing a biotin moiety on the 5' end. The primer pairs of the (A) type above are optimized on human genomic DNA; and the (B) type primer pairs are optimized on a mixture of first strand cDNAs made with and without reverse transcriptase. Primers will be optimized using mRNA derived from appropriate tissues sources, for example, brain, lung, uterus, cartilage, and testis poly A+ RNA.

The information obtained with the (B) type primers is used to assess those putative expressed sequences which can be experimentally observed to have reverse transcriptase-dependent expression. The primer pairs of the (A) type are less stringent in terms of identifying expressed sequences. However, because they amplify genomic DNA as well as cDNA, their ability to amplify genomic DNA provides for the necessary positive control for the primer pair. Negative results with the (B) type are subject to the caveat that the sequence(s) can not be expressed in the tissue first strand that is under examination.

The biotinylated 80-mer oligonucleotides are added en mass to pools of single strand cDNA libraries. Up to 50 probes have been successfully used on pools for 15 different libraries. After the primary selection is performed, all of the captured DNA is repaired to double stranded form using the T7 primer for the commercial libraries in pCMVSPORT, and the Sp6 primer for other constructed libraries in pSPORT. The resulting DNA is electroporated into E. coli DH12S and plated onto 150 mm plates with nylon filters. The cells are scraped and a frozen stock is made, thereby comprising the primary selected library.

One-fifth of the library is generally converted into single strand form and the DNA is assayed with gene specific primer pairs (GSPs). The next round of solution hybridization capture is carried out with 80 mer oligos for only those sequences that are positive with the gene-specific-primers. After the second round, the captured single strand DNAs are repaired with a pool of GSPs, where only the primer complementary to polarity of the single-stranded circular DNA is used (i.e., the antisense primer for pCMVSPORT and pSPORT1 and the sense primer for pSPORT2).

The resulting colonies are screened by PCR using the GSPs. Typically, greater than 80% of the clones are positive for any given GSP. The entire 96 well block of clones is subjected to "mini-prep", as known in the art, and each of clones is sized by either PCR or restriction enzyme digestion. A selection of different sized clones for each targeted sequence is chosen for transposon-hopping and DNA sequencing.

Preferably, as for established cDNA cloning methods used by the skilled practitioner, the libraries employed are of high quality. High complexity and large average insert size are optimal. High Pressure Liquid Chromatography (HPLC) can be employed as a means of fractionating cDNA for the purpose of constructing libraries.

Another embodiment of the present invention provides a method of identifying full-length gene encoding the disclosed polypeptide. The human protein kinase polynucleotide of the present invention, the polynucleotide encoding the human protein kinase polypeptide of the present invention, or the polypeptide encoded by the deposited clone(s) preferably represent the complete coding region (i.e., full-length gene).

Several methods are known in the art for the identification of the 5' or 3' non-coding and/or coding portions of a given gene. The methods described herein are exemplary and should not be construed as limiting the scope of the invention. These methods include, but are not limited to, filter probing, clone enrichment using specific probes, and protocols similar or identical to 5' and 3' "RACE" protocols that are well known in the art. For instance, a method similar to 5 RACE is available for generating the missing 5' end of a desired full-length transcript. (Fromont-Racine et al., Nucleic Acids Res. 21(7):1683-1684 (1993)).

Briefly, in the RACE method, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product can then be sequenced and used to generate the full-length gene.

The above method utilizes total RNA isolated from the desired source, although poly-A+ RNA can be used. The RNA preparation is treated with phosphatase, if necessary, to eliminate 5 phosphate groups on degraded or damaged RNA that can interfere with the later RNA ligase step. The phosphatase is preferably inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

The above-described modified RNA preparation is used as a template for first strand cDNA synthesis employing a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. It can also be advantageous to optimize the RACE protocol to increase the probability of isolating additional 5' or 3' coding or non-coding sequences. Various methods of optimizing a RACE protocol are known in the art; for example, a detailed description summarizing these methods can be found in B. C. Schaefer, Anal. Biochem., 227:255-273, (1995).

An alternative method for carrying out 5' or 3' RACE for the identification of coding or non-coding nucleic acid sequences is provided by Frohman, M. A., et al.,

*Proc.Nat'l.Acad.Sci.USA,* 85:8998-9002 (1988). Briefly, a cDNA clone missing either the 5' or 3' end can be reconstructed to include the absent base pairs extending to the translational start or stop codon, respectively. In some cases, cDNAs are missing the start of translation for an encoded product. A brief description of a modification of the original 5' RACE procedure is as follows. Poly A+ or total RNA is reverse transcribed with Superscript II (Gibco/BRL) and an antisense or an [I] complementary primer specific to any one of the cDNA sequences of the invention. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SalI and ClaI) at the 5' end and a primer containing just these restriction sites. This double-stranded cDNA is PCR amplified for 40 cycles with the same primers, as well as a nested cDNA-specific antisense primer. The PCR products are size-separated on an ethidium bromide-agarose gel and the region of gel containing cDNA products having the predicted size of missing protein-coding DNA is removed.

cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech (Palo Alto; Calif.) which is a modification of a related technique, called single-stranded ligation to single-stranded cDNA, (SLIC), developed by Dumas et al., *Nucleic Acids Res.,* 19:5227-32(1991). The major difference in the latter procedure is that the RNA is alkaline hydrolyzed after reverse transcription and RNA ligase is used to join a restriction site-containing anchor primer to the first-strand cDNA. This obviates the necessity for the dA-tailing reaction which results in a polyT stretch that can impede sequencing.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

Also encompassed by the present invention are polynucleotide sequences that are capable of hybridizing to the novel protein kinase nucleic acid sequences, as set forth in SEQ ID NO:1, under various conditions of stringency. Hybridization conditions are typically based on the melting temperature ($T_m$) of the nucleic acid binding complex or probe (see, G. M. Wahl and S. L. Berger, 1987; *Methods Enzymol.,* 152:399-407 and A. R. Kimmel, 1987; *Methods of Enzymol.,* 152:507-511), and can be used at a defined stringency. For example, included in the present invention are sequences capable of hybridizing under moderately stringent conditions to the protein kinase sequence of SEQ ID NO:1 and other sequences which are degenerate to those which encode the novel protein kinase polypeptide. For example, a non-limiting example of moderate stringency conditions include prewashing solution of 2×SSC, 0.5% SDS, 1.0 mM EDTA, pH 8.0, and hybridization conditions of 50° C., 5×SSC, overnight.

The nucleic acid sequence encoding the novel protein kinase protein of the present invention can be extended by utilizing a partial nucleotide sequence and employing various methods known in the art to detect upstream sequences such as promoters and regulatory elements. For example, one method that can be employed is restriction-site PCR, which utilizes universal primers to retrieve unknown sequence adjacent to a known locus (See, e.g., G. Sarkar, 1993, *PCR Methods Applic.,* 2:318-322). In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR can also be used to amplify or extend sequences using divergent primers based on a known region or sequence (T. Triglia et al., 1988, *Nucleic Acids Res.,* 16:8186). The primers can be designed using OLIGO 4.06 Primer Analysis software (National Biosciences, Inc., Plymouth, Minn.), or another appropriate program, to be 22-30 nucleotides in length, to have a GC content of 50% or more, and to anneal to the target sequence at temperatures about 68° C.-72° C. The method uses several restriction enzymes to generate a suitable fragment in the known region of a gene. The fragment is then circularized by intramolecular ligation and used as a PCR template.

Another method which can be used to amplify or extend sequences is capture PCR which involves PCR amplification of DNA fragments adjacent to a known sequence in human and yeast artificial chromosome (YAC) DNA (M. Lagerstrom et al., 1991, *PCR Methods Applic.,* 1:111-119). In this method, multiple restriction enzyme digestions and ligations can also be used to place an engineered double-stranded sequence into an unknown portion of the DNA molecule before performing PCR. J. D. Parker et al. (1991; *Nucleic Acids Res.,* 19:3055-3060) provide another method which can be used to retrieve unknown sequences. Bacterial artificial chromosomes (BACs) are also used for such applications. In addition, PCR, nested primers, and PROMOTERFINDER libraries can be used to "walk" genomic DNA (Clontech; Palo Alto, Calif.). This process avoids the need to screen libraries and is useful in finding intron/exon junctions. The predicted intron/exon structure of BMSNKC__0020/0021 was determined by homology to the mouse citron kinase 310805 (P1__310805) using the GenewiseDB program (Table 1).

TABLE 1

Predicted Intron/Exon Structure of BMSNKC_0020/0021

| Exon | Start | Stop | Sequence | SEQ ID NO: |
|---|---|---|---|---|
| 1 | 51232 | 51327 | 5'-ATGTTGAAGTTCAAATATGGAG CGCGGAATCCTTTGGATGCTGG | 5 |

TABLE 1-continued

Predicted Intron/Exon Structure of BMSNKC_0020/0021

| Exon | Start | Stop | Sequence | SEQ ID NO: |
|---|---|---|---|---|
| | | | TGCTGCTGAACCCATTGCCAGC | |
| | | | CGGGCCTCCAGGCTGAATCTGT | |
| | | | TCTTCCAG-3' | |
| 2 | 44219 | 44360 | 5'-GGGAAACCACCCTTTATGACTC | 6 |
| | | | AACAGCAGATGTCTCCTCTTTCC | |
| | | | CGAGAAGGGATATTAGATGCCC | |
| | | | TCTTTGTTCTCTTTGAAGAATGC | |
| | | | AGTCAGCCTGCTCTGATGAAGA | |
| | | | TTAAGCACGTGAGCAACTTTGT | |
| | | | CCGGAAGT-3' | |
| 3 | 32682 | 32857 | 5'-ATTCCGACACCATAGCTGAGTT | 7 |
| | | | ACAGGAGCTCCAGCCTTCGGCA | |
| | | | AAGGACTTCGAAGTCAGAAGTC | |
| | | | TTGTAGGTTGTGGTCACTTTGCT | |
| | | | GAAGTGCAGGTGGTAAGAGAGA | |
| | | | AAGCAACCGGGGACATCTATGC | |
| | | | TATGAAAGTGATGAAGAAGAAG | |
| | | | GCTTTATTGGCCCAGGAGCAG-3' | |
| 4 | 25333 | 25434 | 5'-GTTTCATTTTTTGAGGAAGAGCG | 8 |
| | | | GAACATATTATCTCGAAGCACA | |
| | | | AGCCCGTGGATCCCCCAATTAC | |
| | | | AGTATGCCTTTCAGGACAAAAA | |
| | | | TCACCTTTATCTG-3' | |
| 5 | 9245 | 9387 | 5'-GTCATGGAATATCAGCCTGGAG | 9 |
| | | | GGGACTTGCTGTCACTTTTGAAT | |
| | | | AGATATGAGGACCAGTTAGATG | |
| | | | AAAACCTGATACAGTTTTACCT | |
| | | | AGCTGAGCTGATTTTGGCTGTTC | |
| | | | ACAGCGTTCATCTGATGGGATA | |
| | | | CGTGCATCG-3' | |
| 6 | 7930 | 8023 | 5'-AGACATCAAGCCTGAGAACATT | 10 |
| | | | CTCGTTGACCGCACAGGACACA | |
| | | | TCAAGCTGGTGGATTTTGGATCT | |
| | | | GCCGCGAAAATGAATTCAAACA | |
| | | | AGATG-3' | |
| 7 | 324 | 527 | 5'-GTGAATGCCAAACTCCCGATTG | 11 |
| | | | GGACCCCAGATTACATGGCTCC | |
| | | | TGAAGTGCTGACTGTGATGAAC | |
| | | | GGGGATGGAAAAGGCACCTACG | |
| | | | GCCTGGACTGTGACTGGTGGTC | |
| | | | AGTGGGCGTGATTGCCTATGAG | |
| | | | ATGATTTATGGCAGATCCCCCTT | |
| | | | CGCAGAGGGAACCTCTGCCAGA | |
| | | | ACCTTCAATAACATTATGAATTT | |
| | | | CCAG-3' | |

Exon start and stop coordinates (in nucleotides, relative to the human BAC sequence—AC004813/BMSNKC_0020/0021) and exon sequences listed in Table 1.

When screening for full-length cDNAs, it is preferable to use libraries that have been size-selected to include larger cDNAs. Also, random-primed libraries are preferable, since such libraries contain more sequences that comprise the 5' regions of genes. The use of a randomly primed library can be especially preferable for situations in which an oligo d(T) library does not yield a full-length cDNA. Genomic libraries can be useful for extension of sequence into the 5' and 3' non-transcribed regulatory regions.

As described herein, the BMSNKC_0020/0021 polypeptide of the present invention (SEQ ID NO:2) shares significant identity to the mouse citron kinase polypeptide (CRIK; Di Cunto et al., JBC, 273(45):29706-29711 (1998)). The kinase domain of the CRIK polypeptide extends from amino acids 96 to 359 (Ronco et al., JBC, 269:277-283 (1994); Songyang, Z., et al., Mol. Cell. Biol., 16:6486-6493 (1996)). The kinase domain of the BMSNKC_0020/0021 polypeptide shares significant identity to the kinase domain of the CRIK polypeptide, having 91.1% identity, and 95.1% similarity of overlapping amino acids (amino acids 96-319 of SEQ ID NO:2 aligned with amino acids 96-318 of CRIK), as determined using the CLUSTALW algorithm with default parameters.

The kinase domain of the BMSNKC_0020/0021 polypeptide resides from about amino acid 96 to about amino acid 319 of SEQ ID NO:2. In this context, the term "about" may be construed to mean 1, 2, 3, 4, 5, 6, 7, 8, 9, or 10 amino acids beyond the terminii of the above referenced kinase domain.

In preferred embodiments, the present invention encompasses the full-length polynucleotide including the initiating start codon, in addition to, the resulting encoded polypeptide of BMSNKC_0020/0021. Specifically, the present invention encompasses the polynucleotide corresponding to nucleotides 1 thru 957 of SEQ ID NO:1, and the polypeptide corresponding to amino acids 1 thru 319 of SEQ ID NO:2.

Also encompassed are recombinant vectors comprising said encoding sequence, and host cells comprising said vector.

In preferred embodiments, the present invention encompasses a polynucleotide lacking the initiating start codon, in addition to, the resulting encoded polypeptide of BMSNKC_0020/0021. Specifically, the present invention encompasses the polynucleotide corresponding to nucleotides 4 thru 957 of SEQ ID NO:1, and the polypeptide corresponding to amino acids 2 thru 319 of SEQ ID NO:2. Also encompassed are recombinant vectors comprising said encoding sequence, and host cells comprising said vector.

Since the BMSNKC_0020/0021 polypeptide is believed to represent the human ortholog of the mouse citron kinase, BMSNKC_0020/0021 is expected to share significant biological activity with the mouse citron kinase. Moreover, the BMSNKC_0020/0021 polypeptide, and modulators thereof, are expected to be useful for treating diseases and/or disorders that have been associated with the mouse citron kinase, some of which are described by Di Cunto et al. (Neuron. 28:115-127 (2000); which is hereby incorporated by reference herein in its entirety), and others are described herein.

The BMSNKC_0020/0021 polynucleotide has been localized to chromosome 12q24 1-3 (Van Aelst, et al., Genes Dev, 11:2295-2322 (1997)). BMSNKC_0020/0021 polynucleotides and polypeptides, including modulators or fragments thereof, are useful for treating, ameliorating, and/or detecting disorders associated with the 12q24 1-3 chromosome locus.

Expression profiling of the BMSNKC_0020/0021 determined that it was predominately expressed in bone marrow, Jurkat cells, testis, and in specific regions of the brain, particularly amygdala (see FIGS. 4-14).

An additional analysis of BMSNKC_0020/0021 expression levels by TAQMAN™ quantitative PCR (see FIG. 16) in disease cells and tissues indicated that the BMSNKC_0020/0021 polypeptide is differentially expressed in lung-squamous cell carcinoma tumors, and in ovarian tumor tissues. In the lung-squamous cell carcinoma tumors tissue results, 4 samples showed a 9 fold to 65-fold induction in BMSNKC_0020/0021 steady state RNA over that observed in 4 normal samples. These data support a role of BMSNKC_0020/0021 in regulating various lung functions, particularly proliferative responses. BMSNKC_0020/0021 may also be associated with the incidence of lung cancer and modulators of BMSNKC_0020/0021 function may represent a novel therapeutic option in the treatment of lung diseases and disorders, particularly lung cancer, and specifically lung-squamous cell carcinoma.

In the ovarian tumor tissue results, 3 samples showed a 25- to 65-fold induction in BMSNKC_0020/0021 steady state RNA over that observed in 4 normal samples. These data support a role of BMSNKC_0020/0021 in regulating various ovarian functions, particularly proliferative responses. BMSNKC_0020/0021 may also be associated with the incidence of ovarian cancer and modulators of BMSNKC_0020/0021 function may represent a novel therapeutic option in the treatment of ovarian diseases and disorders, particularly ovarian cancers.

The strong expression in immune cells and tissues indicates a role in regulating the proliferation; survival; differentiation; and/or activation of hematopoietic cell lineages, including blood stem cells.

The BMSNKC_0020/0021 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The BMSNKC_0020/0021 polypeptide may be useful for modulating cytokine production, antigen presentation, or other processes, such as for boosting immune responses, etc.

Moreover, the protein may represent a factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong expression in in testis tissue suggests the potential utility for BMSNKC_0020/0021 polynucleotides and polypeptides in treating, diagnosing, prognosing, and/or preventing testicular, in addition to reproductive disorders.

In preferred embodiments, BMSNKC_0020/0021 polynucleotides and polypeptides including agonists and fragements thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The BMSNKC_0020/0021 polynucleotides and polypeptides including agonists and fragements thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the predominate localized expression in testis tissue also emphasizes the potential utility for BMSNKC_0020/0021 polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

The differential expression in lung cancer tissue suggests a potential utility for BMSNKC_0020/0021 polynucleotides and polypeptides in treating, diagnosing, prognosing, and/or preventing pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immumocompromised, HIV, etc.), for example.

Moreover, polynucleotides and polypeptides, including fragments and/or antagonists thereof, have uses which include, directly or indirectly, treating, preventing, diagnosing, and/or prognosing the following, non-limiting, pulmonary infections: pneumonia, bacterial pneumonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pnemonia (for example, as caused by *Mycobacterium tuberculosis*, etc.) mycoplasma pnemonia, fungal pnemonia (for example, as caused by *Pneumocystis carinii, Histoplasma capsulatum, Coccidioides immitis, Blastomyces dermatitidis, Candida* sp., *Cryptococcus neoformans, Aspergillus* sp., Zygomycetes, etc.), Legionnaires' Disease, Chlamydia pnemonia, aspiration pnemonia, Nocordia sp. Infections, *parasitic pnemonia* (for example, as caused by Strongyloides, *Toxoplasma gondii*, etc.) necrotizing pneumonia, in addition to any other pulmonary disease and/or disorder (e.g., non-pneumonia) implicated by the causative agents listed above or elsewhere herein.

The differential expression in ovarian cancer tissue suggests a potential utility for BMSNKC_0020/0021 polynucleotides and polypeptides in treating, diagnosing, prognosing, and/or preventing pulmonary diseases and disorders which include the following, not limiting examples: ovaran cancer; dysfunctional uterine bleeding; amenorrhea; primary dysmenorrhea; sexual dysfunction; infertility; pelvic inflammatory disease; endometriosis; placental aromatase deficiency; premature menopause; placental dysfunction; hormone deficiency; estrogen deficiency; aberrant androgen metabolism; gaberrant onset of female puberty; aberrant showing of female primary sexual characteristics; aberrant showing of female secondary sexual characteristics; precocious puberty; precocious pseudopuberty; incomplete isosexual precocity; premature thelarche; premature adrenarche; premature pubarche; polycystic ovarian disease; aberrant ovarian cycle; menorrhagia; metrorrhagia; menometrorrhagia; dysmenorrhea; hypomenorrhea; polymenorrhea; dysfunctional uterine bleeding; resistant-ovary syndrome; hermaphroditism.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

In preferred embodiments, the following N-terminal BMSNKC_0020/0021 deletion polypeptides are encompassed by the present invention: M1-Q319, L2-Q319, K3-Q319, F4-Q319, K5-Q319, Y6-Q319, G7-Q319, A8-Q319, R9-Q319, N10-Q319, P11-Q319, L12-Q319, D13-Q319, A14-Q319, G15-Q319, A16-Q319, A17-Q319, E18-Q319, P19-Q319, I20-Q319, A21-Q319, S22-Q319, R23-Q319, A24-Q319, S25-Q319, R26-Q319, L27-Q319, N28-Q319, L29-Q319, F30-Q319, F31-Q319, Q32-Q319, G33-Q319, K34-Q319, P35-Q319, P36-Q319, F37-Q319, M38-Q319, T39-Q319, Q40-Q319, Q41-Q319, Q42-Q319, M43-Q319, S44-Q319, P45-Q319, L46-Q319, S47-Q319, R48-Q319, E49-Q319, G50-Q319, I51-Q319, L52-Q319, D53-Q319, A54-Q319, L55-Q319, F56-Q319, V57-Q319, L58-Q319, F59-Q319, E60-Q319, E61-Q319, C62-Q319, S63-Q319, Q64-Q319, P65-Q319, A66-Q319, L67-Q319, M68-Q319, K69-Q319, I70-Q319, K71-Q319, H72-Q319, V73-Q319, S74-Q319, N75-Q319, F76-Q319, V77-Q319, R78-Q319, K79-Q319, Y80-Q319, S81-Q319, D82-Q319, T83-Q319, I84-Q319, A85-Q319, E86-Q319, L87-Q319, Q88-Q319, E89-Q319, L90-Q319, Q91-Q319, P92-Q319, S93-Q319, A94-Q319, K95-Q319, D96-Q319, F97-Q319, E98-Q319, V99-Q319, R100-Q319, S101-Q319, L102-Q319, V103-Q319, G104-Q319, C105-Q319, G106-Q319, H107-Q319, F108-Q319, A109-Q319, E110-Q319, V111-Q319, Q112-Q319, V113-Q319, V114-Q319, R115-Q319, E116-Q319, K117-Q319, A118-Q319, T119-Q319, G120-Q319, D121-Q319, I122-Q319, Y123-Q319, A124-Q319, M125-Q319, K126-Q319, V127-Q319, M128-Q319, K129-Q319, K130-Q319, K131-Q319, A132-Q319, L133-Q319, L134-Q319, A135-Q319, Q136-Q319, E137-Q319, Q138-

Q319, V139-Q319, S140-Q319, F141-Q319, F142-Q319, E143-Q319, E144-Q319, E145-Q319, R146-Q319, N147-Q319, I148-Q319, L149-Q319, S150-Q319, R151-Q319, S152-Q319, T153-Q319, S154-Q319, P155-Q319, W156-Q319, I157-Q319, P158-Q319, Q159-Q319, L160-Q319, Q161-Q319, Y162-Q319, A163-Q319, F164-Q319, Q165-Q319, D166-Q319, K167-Q319, N168-Q319, H169-Q319, L170-Q319, Y171-Q319, L172-Q319, V173-Q319, M174-Q319, E175-Q319, Y176-Q319, Q177-Q319, P178-Q319, G179-Q319, G180-Q319, D181-Q319, L182-Q319, L183-Q319, S184-Q319, L185-Q319, L186-Q319, N187-Q319, R188-Q319, Y189-Q319, E190-Q319, D191-Q319, Q192-Q319, L193-Q319, D194-Q319, E195-Q319, N196-Q319, L197-Q319, I198-Q319, Q199-Q319, F200-Q319, Y201-Q319, L202-Q319, A203-Q319, E204-Q319, L205-Q319, I206-Q319, L207-Q319, A208-Q319, V209-Q319, H210-Q319, S211-Q319, V212-Q319, H213-Q319, L214-Q319, M215-Q319, G216-Q319, Y217-Q319, V218-Q319, H219-Q319, R220-Q319, D221-Q319, I222-Q319, K223-Q319, P224-Q319, E225-Q319, N226-Q319, I227-Q319, L228-Q319, V229-Q319, D230-Q319, R231-Q319, T232-Q319, G233-Q319, H234-Q319, I235-Q319, K236-Q319, L237-Q319, V238-Q319, D239-Q319, F240-Q319, G241-Q319, S242-Q319, A243-Q319, A244-Q319, K245-Q319, M246-Q319, N247-Q319, S248-Q319, N249-Q319, K250-Q319, M251-Q319, V252-Q319, N253-Q319, A254-Q319, K255-Q319, L256-Q319, P257-Q319, I258-Q319, G259-Q319, T260-Q319, P261-Q319, D262-Q319, Y263-Q319, M264-Q319, A265-Q319, P266-Q319, E267-Q319, V268-Q319, L269-Q319, T270-Q319, V271-Q319, M272-Q319, N273-Q319, G274-Q319, D275-Q319, G276-Q319, K277-Q319, G278-Q319, T279-Q319, Y280-Q319, G281-Q319, L282-Q319, D283-Q319, C284-Q319, D285-Q319, W286-Q319, W287-Q319, S288-Q319, V289-Q319, G290-Q319, V291-Q319, I292-Q319, A293-Q319, Y294-Q319, E295-Q319, M296-Q319, I297-Q319, Y298-Q319, G299-Q319, R300-Q319, S301-Q319, P302-Q319, F303-Q319, A304-Q319, E305-Q319, G306-Q319, T307-Q319, S308-Q319, A309-Q319, R310-Q319, T311-Q319, F312-Q319, and/or N313-Q319 of SEQ ID NO:2. Polynucleotide sequences encoding these polypeptides are also provided. The present invention also encompasses the use of these N-terminal BMSNKC__0020/0021 deletion polypeptides as immunogenic and/or antigenic epitopes as described elsewhere herein.

In preferred embodiments, the following C-terminal BMSNKC__0020/0021 deletion polypeptides are encompassed by the present invention: M1-Q319, M1-F318, M1-N317, M1-M316, M1-I315, M1-N314, M1-N313, M1-F312, M1-T311, M1-R310, M1-A309, M1-S308, M1-T307, M1-G306, M1-E305, M1-A304, M1-F303, M1-P302, M1-S301, M1-R300, M1-G299, M1-Y298, M1-I297, M1-M296, M1-E295, M1-Y294, M1-A293, M1-I292, M1-V291, M1-G290, M1-V289, M1-S288, M1-W287, M1-W286, M1-D285, M1-C284, M1-D283, M1-L282, M1-G281, M1-Y280, M1-T279, M1-G278, M1-K277, M1-G276, M1-D275, M1-G274, M1-N273, M1-M272, M1-V271, M1-T270, M1-L269, M1-V268, M1-E267, M1-P266, M1-A265, M1-M264, M1-Y263, M1-D262, M1-P261, M1-T260, M1-G259, M1-I258, M1-P257, M1-L256, M1-K255, M1-A254, M1-N253, M1-V252, M1-M251, M1-K250, M1-N249, M1-S248, M1-N247, M1-M246, M1-K245, M1-A244, M1-A243, M1-S242, M1-G241, M1-F240, M1-D239, M1-V238, M1-L237, M1-K236, M1-I235, M1-H234, M1-G233, M1-T232, M1-R231, M1-D230, M1-V229, M1-L228, M1-I227, M1-N226, M1-E225, M1-P224, M1-K223, M1-I222, M1-D221, M1-R220, M1-H219, M1-V218, M1-Y217, M1-G216, M1-M215, M1-L214, M1-H213, M1-V212, M1-S211, M1-H210, M1-V209, M1-A208, M1-L207, M1-I206, M1-L205, M1-E204, M1-A203, M1-L202, M1-Y201, M1-F200, M1-Q199, M1-I198, M1-L197, M1-N196, M1-E195, M1-D194, M1-L193, M1-Q192, M1-D191, M1-E190, M1-Y189, M1-R188, M1-N187, M1-L186, M1-L185, M1-S184, M1-L183, M1-L182, M1-D181, M1-G180, M1-G179, M1-P178, M1-Q177, M1-Y176, M1-E175, M1-M174, M1-V173, M1-L172, M1-Y171, M1-L170, M1-H169, M1-N168, M1-K167, M1-D166, M1-Q165, M1-F164, M1-A163, M1-Y162, M1-Q161, M1-L160, M1-Q159, M1-P158, M1-I157, M1-W156, M1-P155, M1-S154, M1-T153, M1-S152, M1-R151, M1-S150, M1-L149, M1-I148, M1-N147, M1-R146, M1-E145, M1-E144, M1-E143, M1-F142, M1-F141, M1-S140, M1-V139, M1-Q138, M1-E137, M1-Q136, M1-A135, M1-L134, M1-L133, M1-A132, M1-K131, M1-K130, M1-K129, M1-M128, M1-V127, M1-K126, M1-M125, M1-A124, M1-Y123, M1-I122, M1-D121, M1-G120, M1-T119, M1-A118, M1-K117, M1-E116, M1-R115, M1-V114, M1-V113, M1-Q112, M1-V111, M1-E110, M1-A109, M1-F108, M1-H107, M1-G106, M1-C105, M1-G104, M1-V103, M1-L102, M1-S101, M1-R100, M1-V99, M1-E98, M1-F97, M1-D96, M1-K95, M1-A94, M1-S93, M1-P92, M1-Q91, M1-L90, M1-E89, M1-Q88, M1-L87, M1-E86, M1-A85, M1-I84, M1-T83, M1-D82, M1-S81, M1-Y80, M1-K79, M1-R78, M1-V77, M1-F76, M1-N75, M1-S74, M1-V73, M1-H72, M1-K71, M1-I70, M1-K69, M1-M68, M1-L67, M1-A66, M1-P65, M1-Q64, M1-S63, M1-C62, M1-E61, M1-E60, M1-F59, M1-L58, M1-V57, M1-F56, M1-L55, M1-A54, M1-D53, M1-L52, M1-I51, M1-G50, M1-E49, M1-R48, M1-S47, M1-L46, M1-P45, M1-S44, M1-M43, M1-Q42, M1-Q41, M1-Q40, M1-T39, M1-M38, M1-F37, M1-P36, M1-P35, M1-K34, M1-G33, M1-Q32, M1-F31, M1-F30, M1-L29, M1-N28, M1-L27, M1-R26, M1-S25, M1-A24, M1-R23, M1-S22, M1-A21, M1-I20, M1-P19, M1-E18, M1-A17, M1-A16, M1-G15, M1-A14, M1-D13, M1-L12, M1-P11, M1-N10, M1-R9, M1-A8, and/or M1-G7 of SEQ ID NO:2. Polynucleotide sequences encoding these polypeptides are also provided. The present invention also encompasses the use of these C-terminal BMSNKC__0020/0021 deletion polypeptides as immunogenic and/or antigenic epitopes as described elsewhere herein.

The embodiments of the present invention can be practiced using methods for DNA sequencing which are well known and generally available in the art. The methods can employ such enzymes as the Klenow fragment of DNA polymerase I, SEQUENASE (US Biochemical Corp.; Cleveland, Ohio), Taq polymerase (PE Biosystems), thermostable T7 polymerase (Amersham Pharmacia Biotech; Piscataway, N.J.), or combinations of recombinant polymerases and proofreading exonucleases such as the ELONGASE Amplification System marketed by Life Technologies (Gaithersburg, Md.). Preferably, the process is automated with machines such as the Hamilton Micro Lab 2200 (Hamilton; Reno, Nev.), Peltier Thermal Cycler (PTC200; MJ Research; Watertown, Mass.) and the ABI Catalyst and 373 and 377 DNA sequencers (PE Biosystems). Commercially available capillary electrophoresis systems can be used to analyze the size or confirm the nucleotide sequence of sequencing or PCR products. Capillary electrophoresis is especially preferable for the sequencing of small pieces of DNA, which might be present in limited amounts in a particular sample.

In another embodiment of the present invention, polynucleotide sequences or portions thereof which encode the protein kinase polypeptide or peptides thereof, can comprise recombinant DNA molecules to direct the expression of protein kinase polypeptide products, peptide fragments, or functional equivalents thereof, in appropriate host cells. Because of the inherent degeneracy of the genetic code, other DNA sequences, which encode substantially the same or a functionally equivalent amino acid sequence, can be produced and these sequences can be used to clone and express the protein kinase protein as described.

As will be appreciated by those having skill in the art, it can be advantageous to produce a protein kinase polypeptide-encoding nucleotide sequence possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequence of the present invention can be engineered using methods generally known in the art in order to alter the protein kinase polypeptide-encoding amino acid sequence for a variety of reasons, including, but not limited to, alterations which modify the cloning, processing, and/or expression of the gene product. DNA shuffling by random fragmentation, PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, or introduce mutations, and the like.

In another embodiment of the present invention, natural, modified, or recombinant nucleic acid sequences encoding the protein kinase polypeptide can be ligated to a heterologous sequence to encode a fusion (or chimeric or hybrid) protein. For example, a fusion protein can comprise the amino acid sequence as set forth in SEQ ID NO:2 and an amino acid sequence of an Fc portion (or constant region) of a human immunoglobulin protein. The fusion protein can further comprise an amino acid sequence that differs from SEQ ID NO:2 only by conservative substitutions. As another example, to screen peptide libraries for inhibitors of the protein kinase activity, it can be useful to encode a chimeric protein kinase protein that can be recognized by a commercially available antibody. A fusion protein can also be engineered to contain a cleavage site located between the protein kinase protein-encoding sequence and the heterologous protein sequence, so that the protein kinase protein can be cleaved and purified away from the heterologous moiety.

In a further embodiment, sequences encoding the protein kinase polypeptides can be synthesized in whole, or in part, using chemical methods well known in the art (see, for example, M. H. Caruthers et al., 1980, *Nucl. Acids Res. Symp. Ser.*, 215-223 and T. Horn et al., 1980, *Nucl. Acids Res. Symp. Ser.*, 225-232). Alternatively, the CitK-related protein kinase protein itself, or a fragment or portion thereof, can be produced using chemical methods to synthesize the amino acid sequence of the protein kinase polypeptide, or a fragment or portion thereof. For example, peptide synthesis can be performed using various solid-phase techniques (J. Y. Roberge et al., 1995, *Science,* 269:202-204) and automated synthesis can be achieved, for example, using the ABI 431A Peptide Synthesizer (PE Biosystems).

The newly synthesized CitK-related protein kinase polypeptide or peptide can be substantially purified by preparative high performance liquid chromatography (e.g., T. Creighton, 1983, *Proteins, Structures and Molecular Principles*, W.H. Freeman and Co., New York, N.Y.), by reverse-phase high performance liquid chromatography (HPLC), or other purification methods as known and practiced in the art. The composition of the synthetic peptides can be confirmed by amino acid analysis or sequencing (e.g., the Edman degradation procedure; Creighton, supra). In addition, the amino acid sequence of the protein kinase polypeptide, or any portion thereof, can be altered during direct synthesis and/or combined using chemical methods with sequences from other proteins, or any part thereof, to produce a variant protein kinase polypeptide.

To express a biologically active protein kinase polypeptide or peptide, the nucleotide sequence encoding the protein kinase polypeptide, or functional equivalents, can be inserted into an appropriate expression vector, i.e., a vector, which contains the necessary elements for the transcription and translation of the inserted coding sequence.

In another embodiment of the present invention, an expression vector contains the isolated and purified CitK-related protein kinase polynucleotide sequence as set forth in SEQ ID NO:1, or fragments thereof, encoding the human protein kinase, or a fragment thereof, in which the human CitK-related protein kinase comprises the amino acid sequence as set forth in SEQ ID NO:2. Alternatively, an expression vector can contain the complement of the aforementioned protein kinase nucleic acid sequence.

Expression vectors derived from retroviruses, adenovirus, herpes or vaccinia viruses, or from various bacterial plasmids can be used for the delivery of nucleotide sequences to a target organ, tissue or cell population. Methods, which are well known to those skilled in the art, can be used to construct expression vectors containing sequences encoding the protein kinase polypeptide along with appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vector/host systems can be utilized to contain and express sequences encoding the human protein kinase polypeptide or peptides thereof. Such expression vector/host systems include, but are not limited to, microorganisms such as bacteria (e.g. *E. coli*) transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems, including mammalian cell systems. The host cell employed is not limiting to the present invention. Preferably, the host cell of the invention contains an expression vector comprising the isolated and purified polynucleotide having the nucleic acid sequence of SEQ ID NO:1 and encoding the human protein kinase of this invention, or a functional fragment thereof, comprising the amino acid sequence as set forth in SEQ ID NO:2, or peptide-encoding portion thereof.

Bacterial artificial chromosomes (BACs) can be used to deliver larger fragments of DNA than can be contained and expressed in a plasmid vector. BACs are vectors used to clone DNA sequences of 100-300 kb, on average 150 kb, in size in *E. coli* cells. BACs are constructed and delivered via conventional delivery methods (e.g., liposomes, polycationic amino polymers, or vesicles) for therapeutic purposes.

"Control elements" or "regulatory sequences" are those non-translated regions of the vector, e.g., enhancers, promoters, 5' and 3' untranslated regions, which interact with host cellular proteins to carry out transcription and translation. Such elements can vary in their strength and specificity. Depending on the vector system and host utilized, any number of suitable transcription and translation elements, including constitutive and inducible promoters, can be used. Specific initiation signals can also be used to achieve more efficient translation of sequences encoding the protein kinase polypeptide. Such signals include the ATG initiation codon and adjacent sequences. In cases where sequences encoding the full length protein kinase polypeptide, its initiation codon, and upstream sequences are inserted into the appropriate expression vector, no additional transcriptional or translational control signals may be needed. However, in cases where only the protein kinase coding sequence, or a fragment thereof, is inserted, exogenous translational control signals, including the ATG initiation codon, are optimally provided. Furthermore, the initiation codon should be in the correct reading frame to insure translation of the entire insert. Exogenous translational elements and initiation codons can be of various origins, both natural and synthetic. The efficiency of expression can be enhanced by the inclusion of enhancers which are appropriate for the particular cell system that is used, such as those described in the literature (see, e.g., D. Scharf et al., 1994, *Results Probl. Cell Differ.*, 20:125-162).

In bacterial systems, a number of expression vectors can be selected, depending upon the use intended for the expressed protein kinase product. For example, when large quantities of expressed protein are needed for the generation of antibodies, vectors that direct high level expression of fusion proteins that can be readily purified can be used. Such vectors include, but are not limited to, the multifunctional *E. coli* cloning and expression vectors such as BLUESCRIPT (Stratagene), in which the sequence encoding the protein kinase polypeptide can be ligated into the vector in-frame with sequences for the amino-terminal Met and the subsequent 7 residues of 8-galactosidase, so that a hybrid protein is produced; pIN vectors (see, G. Van Heeke and S. M. Schuster, 1989, *J. Biol. Chem.*, 264:5503-5509); and the like. pGEX vectors (Promega; Madison, Wis.) can also be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. Proteins made in such systems can be designed to include heparin, thrombin, or factor XA protease cleavage sites so that the cloned polypeptide of interest can be released from the GST moiety at will.

In mammalian host cells, a number of viral-based expression systems can be utilized. In cases where an adenovirus is used as an expression vector, sequences encoding the protein kinase polypeptide can be ligated into an adenovirus transcription/translation complex containing the late promoter and tripartite leader sequence. Insertion into a non-essential E1 or E3 region of the viral genome can be used to obtain a viable virus which is capable of expressing the protein kinase polypeptide in infected host cells (J. Logan and T. Shenk, 1984, *Proc. Natl. Acad. Sci.*, 81:3655-3659). In addition, transcription enhancers, such as the Rous sarcoma virus (RSV) enhancer, can be used to increase expression in mammalian host cells. Other expression systems can also be used, for example, but not limited to, yeast, plant, and insect vectors.

Moreover, a host cell strain can be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein can also be used to facilitate correct insertion, folding and/or function. Different host cells having specific cellular machinery and characteristic mechanisms for such post-translational activities (e.g., CHO, HeLa, MDCK, HEK293, and W138) are available from the American Type Culture Collection (ATCC), 10801 University Boulevard, Manassas, Va. 20110-2209, and can be chosen to ensure the correct modification and processing of the foreign protein.

Host cells, transformed with nucleotide sequences encoding the protein kinase protein, or fragments thereof, can be cultured under conditions suitable for the expression and recovery of the protein from cell culture. The protein produced by a recombinant cell can be secreted or contained intracellularly depending on the sequence and/or the vector used. As will be understood by those having skill in the art, expression vectors containing polynucleotides which encode a protein kinase protein can be designed to contain signal sequences which direct secretion of the protein kinase protein through a prokaryotic or eukaryotic cell membrane. Other constructions can be used to join nucleic acid sequences encoding a protein kinase protein to a nucleotide sequence encoding a polypeptide domain, which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp.; Seattle, Wash.). The inclusion of cleavable linker sequences such as those specific for Factor XA or enterokinase (Invitrogen; San Diego, Calif.) between the purification domain and protein kinase protein can be used to facilitate purification. One such expression vector provides for expression of a fusion protein containing, for example, the protein kinase of the present invention and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263-281, while the enterokinase cleavage site provides a means for purifying the protein kinase from the fusion protein. For a discussion of suitable vectors for fusion protein production, see D. J. Kroll et al., 1993; *DNA Cell Biol.*, 12:441-453.

Any number of selection systems can be used to recover transformed cell lines. These include, but are not limited to, the Herpes Simplex Virus thymidine kinase (HSV TK), (M. Wigler et al., 1977, *Cell,* 11:223-32) and adenine phosphoribosyltransferase (I. Lowy et al., 1980, *Cell,* 22:817-23) genes which can be employed in tk$^-$ or aprt$^-$ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.*, 77:3567-70); npt, which confers resistance to the aminoglycosides neomycin and G-418 (F. Colbere-Garapin et al., 1981, *J. Mol. Biol.*, 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.*, 85:8047-51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.*, 55:121-131).

Although the presence or absence of marker gene expression suggests that the gene of interest is also present, the presence and expression of the desired gene of interest may need to be confirmed. For example, if the nucleic acid sequence encoding the protein kinase polypeptide is inserted within a marker gene sequence, recombinant cells containing the polynucleotide sequence encoding the protein kinase polypeptide can be identified by the absence of marker gene function. Alternatively, a marker gene can be placed in tandem with a sequence encoding the protein kinase polypeptide under the control of a single promoter. Expression of the marker gene in response to induction or selection typically indicates co-expression of the tandem gene.

A wide variety of labels and conjugation techniques are known and employed by those skilled in the art and can be used in various nucleic acid and amino acid assays. Means for producing labeled hybridization or PCR probes for detecting sequences related to polynucleotides encoding the protein kinase polypeptide include oligo-labeling, nick translation, end-labeling, or PCR amplification using a labeled nucleotide. Alternatively, the sequences encoding the protein kinase polypeptide of this invention, or any portion or fragment thereof, can be cloned into a vector for the production of an mRNA probe. Such vectors are known in the art, are commercially available, and can be used to synthesize RNA probes in vitro by addition of an appropriate RNA polymerase, such as T7, T3, or SP(6) and labeled nucleotides. These procedures can be conducted using a variety of commercially available kits (e.g., Amersham Pharmacia Biotech, Promega and U.S. Biochemical Corp.). Suitable reporter molecules or labels which can be used include radionuclides, enzymes, fluorescent, chemiluminescent, or chromogenic agents, as well as substrates, cofactors, inhibitors, magnetic particles, and the like.

Alternatively, host cells which contain the nucleic acid sequence coding for the protein kinase polypeptide of the invention and which express the CitK-related protein kinase polypeptide product can be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

The presence of a polynucleotide sequence encoding the protein kinase polypeptide can be detected by DNA-DNA or DNA-RNA hybridization, or by amplification using probes, portions, or fragments of the polynucleotide encoding the protein kinase polypeptide. Nucleic acid amplification based assays involve the use of oligonucleotides or oligomers based on the nucleic acid sequence encoding the protein kinase polypeptide to detect transformants containing DNA or RNA encoding the protein kinase polypeptide.

In addition to recombinant production, fragments of protein kinase polypeptides can be produced by direct peptide synthesis using solid phase techniques (J. Merrifield, 1963, *J. Am. Chem. Soc.*, 85:2149-2154). Protein synthesis can be performed using manual techniques or by automation. Automated synthesis can be achieved, for example, using an ABI 431A Peptide Synthesizer (PE Biosystems). Various fragments of the protein kinase polypeptide can be chemically synthesized separately and then combined using chemical methods to produce the full length molecule.

Diagnostic Assays

In another embodiment of the present invention, antibodies which specifically bind to the BMSNKC_0020/0021 polypeptide can be used for the diagnosis of conditions or diseases characterized by expression (or overexpression) of the protein kinase polynucleotide or polypeptide, or in assays to monitor patients being treated with the protein kinase polypeptide, or agonists, antagonists, or inhibitors of the novel protein kinase. The antibodies useful for diagnostic purposes can be prepared in the same manner as those described herein for use in therapeutic methods. Diagnostic assays for the BMSNKC_0020/0021 polypeptide include methods which utilize the antibody and a label to detect the protein in human body fluids or extracts of cells or tissues. The antibodies can be used with or without modification, and can be labeled by joining them, either covalently or non-covalently, with a reporter molecule. A wide variety of reporter molecules known to those in the art can be used, several of which are described herein.

In particular, antibodies or antibody fragments having specific binding affinity to the CitK-related protein kinase polypeptide in a sample can be used to probe the sample with the antibody under conditions suitable for kinase-antibody immunocomplex formation and to detect of the presence and/or amount of the antibody complexed to the kinase polypeptide. Diagnostic kits for performing such methods can be constructed to include antibodies or antibody fragments specific for the kinase as well as a conjugate of a binding partner of the antibodies or the antibodies themselves.

Another embodiment of the present invention involves a method of detecting a homologue of the CitK-related protein kinase or an antibody-reactive fragment thereof, in the sample. The method comprises a) contacting the sample with an antibody specific for the protein kinase polypeptide of the present invention, or an antigenic fragment thereof, under conditions in which an antigen-antibody complex can form between the antibody and the polypeptide or antigenic fragment thereof in the sample; and b) detecting the antigen-antibody complex formed in step a), wherein detection of the complex indicates the presence of the protein kinase polypeptide, or an antigenic fragment thereof, in the sample.

Several assay protocols including enzyme-linked immunosorbent assay (ELISA), radioimmunoassay (RIA), and fluorescence activated cell sorting (FACS) for measuring protein kinase polypeptide are known in the art and provide a basis for diagnosing altered or abnormal levels of protein kinase polypeptide expression. Normal or standard values for protein kinase polypeptide expression are established by combining body fluids or cell extracts taken from normal mammalian subjects, preferably human, with antibody to the protein kinase polypeptide under conditions suitable for complex formation. The amount of standard complex formation can be quantified by various methods; photometric means are preferred. Quantities of protein kinase polypeptide expressed in a subject or test sample, control sample, and disease samples from biopsied tissues are compared with the standard values. Deviation between standard and subject values establishes the parameters for diagnosing disease.

A variety of protocols for detecting and measuring the expression of the protein kinase polypeptide using either polyclonal or monoclonal antibodies specific for the polypeptide, or epitopic portions thereof, are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the protein kinase polypeptide is preferred, but a competitive binding assay can also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211-1216).

In another embodiment of the present invention, a method of using the protein kinase-encoding polynucleotide sequence to purify a molecule or compound in a sample, wherein the molecule or compound specifically binds to the polynucleotide, is contemplated. The method comprises: a) combining the protein kinase-encoding polynucleotide of the invention with a sample undergoing testing to determine if the sample contains the molecule or compound, under conditions to allow specific binding; b) detecting specific binding between the protein kinase-encoding polynucleotide and the molecule or compound, if present; c) recovering the bound polynucleotide; and d) separating the polynucleotide from the molecule or compound, thereby obtaining a purified molecule or compound.

This invention also relates to a method of using the CitK-related protein kinase polynucleotide as a diagnostic reagent. For example, the detection of a mutated form of the protein kinase gene associated with a dysfunction can provide a diagnostic tool that can add to or define diagnosis of a disease or susceptibility to a disease which results from under-expression, over-expression, or altered expression of the protein kinase. Individuals carrying mutations in the protein kinase gene can be detected at the DNA level by a variety of techniques.

Nucleic acids for diagnosis can be obtained from various sources of a subject, for example, from cells, tissue, blood, urine, saliva, tissue biopsy or autopsy material. Genomic DNA can be used directly for detection or can be amplified by using PCR or other amplification techniques prior to analysis. RNA or cDNA can also be used in a similar fashion. Deletions and insertions in the human protein kinase-encoding polynucleotide can be detected by a change in size of the amplified product compared with that of the normal genotype. Hybridizing amplified DNA to the labeled protein kinase polynucleotide sequence can identify point mutations. Perfectly matched sequences can be distinguished from mismatched duplexes by RNase digestion or by differences in melting temperatures. DNA sequence differences can also be detected by alterations in electrophoretic mobility of DNA fragments in gels, with or without denaturing agents, or by direct DNA sequencing. See, for example, Myers et al., *Science* (1985) 230:1242. Sequence changes at specific locations can also be revealed by nuclease protection assays, such as RNase and S1 protection or the chemical cleavage method. (See Cotton et al., *Proc. Natl. Acad. Sci., USA* (1985) 85:43297-4401).

In another embodiment, an array of oligonucleotide probes comprising the CitK-related protein kinase nucleotide sequence or fragments thereof can be constructed to conduct efficient screening of, for example, genetic mutations. Array technology methods are well known, have general applicability and can be used to address a variety of questions in molecular genetics, including gene expression, genetic linkage, and genetic variability (see for example: M. Chee et al., *Science*, 274:610-613, 1996).

Yet another aspect of the present invention involves a method of screening a library of molecules or compounds with the protein kinase-encoding polynucleotide or polypeptide to identify at least one molecule or compound therein which specifically binds to the protein kinase polynucleotide or polypeptide sequence. Such a method includes a) combining a protein kinase-encoding polynucleotide of the present invention with a library of molecules or compounds under conditions to allow specific binding; and b) detecting specific binding, thereby identifying a molecule or compound, which specifically binds to a protein kinase-encoding polynucleotide sequence, wherein the library is selected from DNA molecules, RNA molecules, artificial chromosome constructions, PNAs, peptides and proteins, polypeptides, polynucleotides, or both.

The present invention provides diagnostic assays for determining or monitoring through detection of a mutation in the CitK-related protein kinase gene (polynucleotide) described herein susceptibility to the following conditions, diseases, or disorders: cancers; immune-related diseases and disorders, cardiovascular disease, brain or neuronal-associated diseases, and metabolic disorders. More specifically, disorders including cancers of tissues, blood, or hematopoietic origin, particularly those involving breast, colon, lung, prostate, cervical, brain, ovarian, bladder, or kidney; central or peripheral nervous system diseases and conditions including migraine, pain, sexual dysfunction, mood disorders, attention disorders, cognition disorders, hypotension, and hypertension; psychotic and neurological disorders, including anxiety, schizophrenia, manic depression, delirium, dementia, severe mental retardation and dyskinesias, such as Huntington's disease or Tourette's Syndrome, neurodegenerative diseases including Alzheimer's, Parkinson's, multiple sclerosis, and amyotrophic lateral sclerosis; viral or non-viral infections caused by HIV-1, HIV-2, or other viral- or prion-agents or fungal- or bacterial-organisms; metabolic disorders, including diabetes and obesity and their related syndromes, among others; cardiovascular disorders including reperfusion testenosis, coronary thrombosis, clotting disorders, unregulated cell growth disorders, atherosclerosis; ocular disease including glaucoma, retinopathy, and macular degernation; inflammatory disorders including rhematoid arthritis, chronic inflammatory bowel disease, chronic inflammatory pelvic disease, multiple sclerosis, asthma, osteoarthritis, psoriasis, atherosclerosis, rhinitis, autoimmunity, and organ transplant rejection.

In addition, such diseases, disorder, or conditions, can be diagnosed by methods of determining from a sample derived from a subject having an abnormally decreased or increased level of the protein kinase polypeptide or the protein kinase mRNA. Decreased or increased expression can be measured at the RNA level using any of the methods well known in the art for the quantification of polynucleotides, such as, for example, PCR, RT-PCR, RNase protection, Northern blotting and other hybridization methods. Assay techniques that can be used to determine levels of a protein, such as a protein kinase in a sample derived from a host are well known to those of skill in the art. Such assay methods include, without limitation, radioimmunoassays, competitive-binding assays, Western Blot analysis and ELISA assays.

In another of its aspects, this invention relates to a kit for detecting and diagnosing a protein kinase-associated disease or susceptibility to such a disease, which comprises the CitK-related protein kinase polynucleotide, preferably the nucleotide sequence of SEQ ID NO:1, or a fragment thereof; or a nucleotide sequence complementary to the protein kinase polynucleotide of SEQ ID NO:1; or a CitK-related protein kinase polypeptide, preferably the polypeptide of SEQ ID NO:2, or a fragment thereof; or an antibody to the protein kinase polypeptide, preferably to the polypeptide of SEQ ID NO:2, an epitope-containing portion thereof, or combinations of the foregoing. It will be appreciated that in any such kit, any of the previously mentioned components can comprise a substantial component. Also preferably included are instructions for use.

The protein kinase polynucleotides which can be used in the diagnostic assays according to the present invention include oligonucleotide sequences, complementary RNA and DNA molecules, and PNAs. The polynucleotides can be used to detect and quantify protein kinase-encoding nucleic acid expression in biopsied tissues in which expression (or under- or over-expression) of the protein kinase polynucleotide can be determined, as well as correlated with disease. The diagnostic assays can be used to distinguish between the absence of protein kinase, the presence of protein kinase, or the excess expression of protein kinase, and to monitor the regulation of protein kinase polynucleotide levels during therapeutic treatment or intervention.

In a related aspect, hybridization with PCR probes which are capable of detecting polynucleotide sequences, including genomic sequences, encoding a protein kinase polypeptide according to the present invention, or closely related molecules, can be used to identify nucleic acid sequences which encode a protein kinase polypeptide. The specificity of the probe, whether it is made from a highly specific region, for example, about 8 to 10 contiguous nucleotides in the 5' regulatory region, or a less specific region, for example, especially n the 3' coding region, and the stringency of the hybridization or amplification (maximal, high, intermediate, or low) will determine whether the probe identifies only naturally occurring sequences encoding the protein kinase polypeptide, alleles thereof, or related sequences.

Probes can also be used for the detection of related sequences, and should preferably contain at least 50% of the nucleotides encoding the protein kinase polypeptide. The hybridization probes or primers of this invention can be DNA or RNA and can be derived from the nucleotide sequence of SEQ ID NO:1, or can be derived from genomic sequence, including promoter, enhancer elements, and introns of the naturally occurring protein kinase protein, wherein the probes or primers comprise a polynucleotide sequence capable of hybridizing with the polynucleotide of SEQ ID NO:1, under low, moderate, or high stringency conditions.

Methods for producing specific hybridization probes for DNA encoding the protein kinase polypeptide described herein include the cloning of a nucleic acid sequence that encodes the protein kinase polypeptide, or protein kinase derivatives, into vectors for the production of mRNA probes. Such vectors are known in the art, or are commercially available, and can be used to synthesize RNA probes in vitro by means of the addition of the appropriate RNA polymerases and the appropriate labeled nucleotides. Hybridization probes can be labeled by a variety of detector/reporter groups, including, but not limited to, radionuclides such as $^{32}P$ or $^{35}S$, or enzymatic labels, such as alkaline phosphatase coupled to the probe via avidin/biotin coupling systems, and the like.

The polynucleotide sequences encoding the protein kinase polypeptides of this invention, or fragments thereof, can be used for the diagnosis of disorders associated with expression of protein kinases. The polynucleotide sequence encoding the protein kinase polypeptide can be used in Southern or Northern analysis, dot blot, or other membrane-based technologies; in PCR technologies; or in dipstick, pin, ELISA or chip assays utilizing fluids or tissues from patient biopsies to detect the status of, for example, levels of, or overexpression of, the protein kinase, or to detect altered protein kinase expression or levels. Such qualitative or quantitative methods are commonly practiced in the art.

In a particular aspect, a nucleotide sequence encoding the protein kinase polypeptide as described herein can be useful in assays that detect activation or induction of various neoplasms, cancers, or other protein kinase-related diseases, disorders, or conditions. The nucleotide sequence encoding the protein kinase polypeptide can be labeled by standard methods, and added to a fluid or tissue sample from a patient, under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the protein kinase polypeptide in the sample indicates the presence of the associated disease. Such assays can also be used to evaluate the efficacy of a particular therapeutic treatment regimen in animal studies, in clinical trials, or in monitoring the treatment or responsiveness of an individual patient.

Once disease is established and a treatment protocol is initiated, hybridization assays can be repeated on a regular basis to evaluate whether the level of expression in the patient begins to approximate that which is observed in a normal individual. The results obtained from successive assays can be used to show the efficacy of treatment over a period ranging from several days to months.

With respect to tumors or cancer, the presence of an abnormal amount or level of the CitK-related protein kinase transcript in biopsied tissue from an individual can indicate a predisposition for the development of the disease, or can provide a means for detecting the disease prior to the appearance of actual clinical symptoms. A more definitive diagnosis of this type can allow health practitioners to employ preventative measures or aggressive treatment earlier, thereby preventing the development or further progression of the tumor or cancer.

Additional diagnostic uses for oligonucleotides designed from the nucleic acid sequences encoding the novel protein kinase polypeptide of this invention can involve the use of PCR. Such oligomers can be chemically synthesized, generated enzymatically, or produced from a recombinant source. Oligomers will preferably comprise two nucleotide sequences: one with sense orientation (5'→3') and another with antisense orientation (3'→5'), employed under optimized conditions for identification of a specific gene or condition. The same two oligomers, nested sets of oligomers, or even a degenerate pool of oligomers can be employed under less stringent conditions for detection and/or quantification of closely related DNA or RNA sequences.

Methods suitable for quantifying the expression of protein kinase include radiolabeling or biotinylating nucleotides, co-amplification of a control nucleic acid, and standard curves onto which the experimental results are interpolated (P. C. Melby et al., 1993, *J. Immunol. Methods,* 159:235-244; and C. Duplaa et al., 1993, *Anal. Biochem.,* 229-236). The speed of quantifying multiple samples can be accelerated by running the assay in an ELISA format where the oligomer of interest is presented in various dilutions and a spectrophotometric or colorimetric response gives rapid quantification.

In another embodiment of the invention, a compound to be tested can be radioactively, colorimetrically or fluorimetrically labeled using methods well known in the art and incubated with the protein kinase for testing. After incubation, it is determined whether the test compound is bound to the protein kinase polypeptide. If so, the compound is to be considered a potential agonist or antagonist. Functional assays are performed to determine whether the receptor activity is activated (or enhanced or increased) or inhibited (or decreased or reduced). These assays include, but are not limited to, cell cycle analysis and in vivo tumor formation assays. Responses can also be measured in cells expressing the receptor using signal transduction systems including, but not limited to, protein phosphorylation, adenylate cyclase activity, phosphoinositide hydrolysis, guanylate cyclase activity, ion fluxes (i.e. calcium) and pH changes. These types of responses can either be present in the host cell or introduced into the host cell along with the receptor.

Yet another embodiment of the present invention is directed to methods of identifying compounds which modulate (i.e. increase or decrease) activity of the kinase polypeptide comprising contacting the kinase polypeptide with a compound, and determining whether the compound modifies activity of the kinase polypeptide. As described herein, the kinase polypeptide can include the full length protein, or portion of a full-length sequence, such as a catalytic domain, as defined herein. In some instances, the kinase polypeptide of the invention comprise as less than the entire catalytic domain, yet exhibits kinase or kinase-like activity. Compounds identified by these methods are also referred to as "modulators of protein kinases." The activity in the presence of the test compound is compared to the activity in the absence of the test compound. Where the activity of a sample containing the test compound is higher than the activity in a sample lacking the test compound, the compound will have increased the activity. Similarly, where the activity of a sample containing the test compound is lower than the activity in the sample lacking the test compound, the compound will have inhibited the activity.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as "hits" or "leads" in other drug discovery screens, while others are derived from natural products, and still others arise from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see *Science* 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). Identification of modulators through use of the various libraries described herein permits modification of the candidate "hit" (or "lead") to optimize the capacity of the "hit" to modulate activity. Still other candidate inhibitors contemplated by the invention can be designed and include soluble forms of binding partners, as well as such binding partners as chimeric, or fusion, proteins. A "binding partner" as used herein broadly encompasses both natural binding partners as described above as well as chimeric polypeptides, peptide modulators other than natural ligands, antibodies, antibody fragments, and modified compounds comprising antibody domains that are immunospecific for the expression product of the identified kinase gene.

The invention contemplates a multitude of assays to screen and identify inhibitors of ligand binding to the CitK-related protein kinase polypeptide. In one example, the protein kinase polypeptide is immobilized and interaction with a binding partner is assessed in the presence and absence of a candidate modulator such as an inhibitor compound. In another example, interaction between the kinase polypeptide and its binding partner is assessed in a solution assay, both in the presence and absence of a candidate inhibitor compound. In either assay, an inhibitor is identified as a compound that decreases binding between the kinase polypeptide and its natural binding partner. Another contemplated assay involves a variation of the di-hybrid assay wherein an inhibitor of protein/protein interactions is identified by detection of a positive signal in a transformed or transfected host cell, as described in PCT publication number WO 95/20652, published Aug. 3, 1995 and is included by reference herein including any figures, tables, or drawings.

The present invention is particularly useful for screening candidate compounds by using the CitK-related protein kinase polypeptide in any of a variety of drug screening techniques. The candidate compounds to be screened include, but are not limited to, compounds of extracellular, intracellular, biological or chemical origin. The kinase polypeptide employed in such a screening can be in any form, preferably, free in solution, attached to a solid support, borne on a cell surface or located intracellularly. One skilled in the art can, for example, measure the formation of complexes between a kinase polypeptide and the candidate compound. Alternatively, the skilled artisan can examine the modulation of the activity of the protein kinase as described herein.

The present invention further embraces a method of screening for candidate compounds capable of modulating the activity of a protein kinase-encoding polypeptide. Such a method comprises a) contacting a test compound with a cell or tissue expressing the protein kinase polypeptide of the invention (e.g., recombinant expression); and b) selecting as candidate modulating compounds those test compounds that modulate activity of the protein kinase polypeptide. Those candidate compounds which modulate protein kinase activity are preferably agonists or antagonists, more preferably antagonists of protein kinase activity. By the term "expressing" is meant the production of kinases of the invention from a nucleic acid vector containing kinase genes within a cell. The nucleic acid vector is transfected into cells using well known techniques in the art as described herein.

In particular, the invention features methods for identifying a substance that modulates kinase activity comprising the steps of: (a) contacting the kinase polypeptide having the amino acid sequence of SEQ ID NO:2 with the substance; (b) measuring the activity of the kinase polypeptide; and (c) determining whether the substance modulates the activity of the kinase. The skilled artisan will appreciate that the kinase polypeptide of the invention, including, for example, an active portion of a full-length sequence such as a catalytic domain or a portion thereof, are useful for the identification of a substance which modulates kinase activity. Kinase polypeptide having a functional activity (for example, catalytic activity as defined herein) is useful for identifying a substance that modulates kinase activity.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10\text{-}2$ M, $10\text{-}2$ M, $5\times10\text{-}3$ M, $10\text{-}3$ M, $5\times10\text{-}4$ M, $10\text{-}4$ M, $5\times10\text{-}5$ M, $10\text{-}5$ M, $5\times10\text{-}6$ M, $10\text{-}6$M, $5\times10\text{-}7$ M, $107$ M, $5\times10\text{-}8$ M, $10\text{-}8$ M, $5\times10\text{-}9$ M, $10\text{-}9$ M, $5\times10\text{-}10$ M, $10\text{-}10$ M, $5\times10\text{-}11$ M, $10\text{-}11$ M, $5\times10\text{-}12$ M, $10\text{-}12$ M, $5\times10\text{-}13$ M, $10\text{-}13$ M, $5\times10\text{-}14$ M, $10\text{-}14$ M, $5\times10\text{-}15$ M, or $10\text{-}15$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161 (4):1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9): 1153-1167 (1998); Bartunek et a Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the BMSNKC_0020/0021 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intra-peritoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an BMSNKC_0020/0021 polypeptide or, more preferably, with a BMSNKC_0020/0021 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516, 637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)1 and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the BMSNKC_0020/0021 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media.

The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62:191-217 (1993); May, 1993, TIB TECH 11(5): 155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J, L, Analyst., 126(6):798-802, (2001); Jenkins, A, L., Yin, R., Jensen, J, L, Analyst., 126(6):798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072-3, (2001); and Quaglia, M., Chenon, K., Hall, A, J., De, Lorenzi, E., Sellergren, B, J. Am. Chem, Soc., 123(10):2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Therapeutic Assays

The BMSNKC_0020/0021 protein according to this invention can play a role in cell signaling, in cell cycle regulation, and/or in neurological disorders. The BMSNKC_0020/0021 protein can further be involved in neoplastic, cardiovascular, metabolic, and immunological disorders.

A preferred method of treating a BMSNKC_0020/0021 protein kinase-associated disease, disorder, syndrome, or condition in a mammal comprises administration of a modulator, preferably an inhibitor or antagonist, of the BMSNKC_0020/0021 polypeptide or homologue of the invention, in an amount effective to treat, reduce, and/or ameliorate the symptoms incurred by the protein kinase-associated disease, disorder, syndrome, or condition. In some instances, an agonist or enhancer of the BMSNKC_0020/0021 polypeptide or homologue of the invention is administered in an amount effective to treat and/or ameliorate the symptoms incurred by a protein kinase-related disease, disorder, syndrome, or condition. In other instances, the administration of the BMSNKC_0020/0021 protein kinase polypeptide itself, or homologue thereof of the present invention is envisioned for administration to treat a protein kinase associated disease.

The invention further features methods for identifying a substance that modulates protein kinase activity in a cell comprising the steps of: (a) expressing the kinase polypeptide in a cell, wherein the polypeptide is selected from the amino acid sequence set forth in SEQ ID NO:2; (b) adding a test substance to the cell; and (c) monitoring a change in cell phenotype or in the interaction between the kinase polypeptide and a natural interacting partner. The skilled artisan will appreciate that the kinase polypeptide of the invention, including, for example, a portion of a full-length sequence, such as a catalytic domain or a portion thereof, are useful for the identification of a substance which modulates protein kinase activity.

In yet another embodiment of the present invention, an expression vector containing the complement of the polynucleotide encoding the BMSNKC_0020/0021 protein kinase polypeptide is administered to an individual to treat or prevent any one of the types of diseases, disorders, or conditions previously described above, in an antisense therapy method.

The BMSNKC_0020/0021 protein; modulators, including antagonists, antibodies, and agonists; complementary sequences; or vectors of the present invention can also be administered in combination with other appropriate therapeutic agents as necessary or desired. The skilled practitioner in the art, according to conventional pharmaceutical and clinical principles can make selection of the appropriate agents for use in combination therapy. The combination of therapeutic agents can act synergistically to effect the treatment or prevention of the various disorders described above. Using this approach, therapeutic efficacy can be achieved with lower dosages of each agent, thus reducing the potential for adverse side effects or adverse events.

Antagonists or inhibitors of the BMSNKC_0020/0021 polypeptide of this invention can be produced using methods which are generally known in the art. In particular, purified protein kinase protein, or fragments thereof, can be used to produce antibodies, or to screen libraries of pharmaceutical agents, to identify those agents which specifically bind to the novel protein kinase polypeptides as described herein.

Antibodies specific for BMSNKC_0020/0021 polypeptide, or immunogenic peptide fragment thereof, can be generated using methods that have long been known and conventionally practiced in the art. Such antibodies can include, but are not limited to, polyclonal, monoclonal, neutralizing antibodies, (i.e., those which inhibit dimer formation), chimeric, single chain, Fab fragments, and fragments produced by an Fab expression library.

For the production of antibodies, various hosts, including goats, rabbits, sheep, rats, mice, humans, and others, can be immunized by injection with the BMSNKC_0020/0021 polypeptide, or any immunogenic and/or epitope-containing fragment or oligopeptide thereof, which has immunogenic properties. Depending on the host species, various adjuvants can be used to increase the immunological response. Non-limiting examples of suitable adjuvants include Freund's (incomplete) adjuvant, mineral gels such as aluminum hydroxide or silica, and surface-active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvumn*.

Preferably, the BMSNKC_0020/0021 polypeptide, peptides, fragments, or oligopeptides used to induce antibodies to the BMSNKC_0020/0021 polypeptide immunogen have an amino acid sequence of at least five amino acids in length, and more preferably, at least 7-10, or more, amino acids. It is also preferable that the immunogens are identical to a portion of the amino acid sequence of the natural protein, as well as the entire amino acid sequence. The peptides, fragments or oligopeptides can comprise a single epitope or antigenic determinant or multiple epitopes. Short stretches of BMSNKC__0020/0021 amino acids can be fused with another protein as carrier, such as KLH, such that antibodies are produced against the chimeric molecule.

Monoclonal antibodies to the BMSNKC__0020/0021 polypeptide, or immunogenic fragments thereof, can be prepared using any technique which provides for the production of antibody molecules by continuous cell lines in culture. Such techniques are conventionally used in the art. These include, but are not limited to, the hybridoma technique, the human B-cell hybridoma technique, and the EBV-hybridoma technique (G. Kohler et al., 1975, *Nature,* 256:495-497; D. Kozbor et al., 1985, *J. Immunol. Methods,* 81:31-42; R. J. Cote et al., 1983, *Proc. Natl. Acad. Sci. USA,* 80:2026-2030; and S. P. Cole et al., 1984, *Mol. Cell Biol.,* 62:109-120). The production of monoclonal antibodies to immunogenic proteins and peptides is well known and routinely used in the art.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA,* 81:6851-6855; M. S. Neuberger et al., 1984, *Nature,* 312: 604-608; and S. Takeda et al., 1985, *Nature,* 314:452-454). Alternatively, techniques described for the production of single chain antibodies can be adapted, using methods known in the art, to produce BMSNKC__0020/0021 polypeptide-specific single chain antibodies. Antibodies with related specificity, but of distinct idiotypic composition, can be generated by chain shuffling from random combinatorial immunoglobulin libraries (D. R. Burton, 1991, *Proc. Natl. Acad. Sci. USA,* 88:11120-3). Antibodies can also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA,* 86:3833-3837 and G. Winter et al., 1991, *Nature,* 349:293-299).

Antibody fragments, which contain specific binding sites for the BMSNKC__0020/0021 polypeptide, can also be generated. For example, such fragments include, but are not limited to, $F(ab')_2$ fragments which can be produced by pepsin digestion of the antibody molecule and Fab fragments which can be generated by reducing the disulfide bridges of the $F(ab')_2$ fragments. Alternatively, Fab expression libraries can be constructed to allow rapid and easy identification of monoclonal Fab fragments with the desired specificity (e.g., W. D. Huse et al., 1989, *Science,* 254.1275-1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between the BMSNKC__0020/0021 polypeptide and its specific antibody. A two-site, monoclonal-based immunoassay utilizing monoclonal antibodies reactive with two non-interfering BMSNKC__0020/0021 polypeptide epitopes is suitable, but a competitive binding assay can also be employed (Maddox, supra).

To induce an immunological response in a mammal, a host animal is inoculated with the BMSNKC__0020/0021 polypeptide, or an immunogenic fragment thereof, of this invention in an amount adequate to produce an antibody and/or a T cell immune response. Yet another aspect of the invention relates to a method of inducing immunological response in a mammal, if applicable or required. Such a method comprises delivering the BMSNKC__0020/0021 polypeptide via a vector directing expression of BMSNKC__0020/0021 polynucleotide in vivo in order to induce such an immunological response to produce antibody to protect the host animal from BMSNKC__0020/0021-related diseases.

A further aspect of the invention relates to an immunological vaccine or immunogen formulation or composition which, when introduced into a mammalian host, induces an immunological response in that mammal to the BMSNKC__0020/0021 polypeptide, wherein the composition contains BMSNKC__0020/0021 polypeptide or BMSNKC__0020/0021 encoding gene. The vaccine or immunogen formulation can further comprise a suitable carrier. Since the BMSNKC__0020/0021 polypeptide can be broken down in the stomach, it is preferably administered parenterally (including subcutaneous, intramuscular, intravenous, intradermal, etc., injection). Formulations suitable for parenteral administration include aqueous and non-aqueous sterile injection solutions which can contain anti-oxidants, buffers, bacteriostats and solutes which render the formulation isotonic with the blood of the recipient; and aqueous and non-aqueous sterile suspensions which can include suspending agents or thickening agents.

The formulations can be presented in unit-dose or multi-dose containers, for example, sealed ampoules and vials, and can be stored in a freeze-dried condition requiring only the addition of the sterile liquid carrier immediately prior to use. A vaccine formulation can also include adjuvant systems for enhancing the immunogenicity of the formulation, such as oil-in-water systems and other systems known in the art. The dosage will depend on the specific activity of the vaccine and can be readily determined by routine experimentation.

In an aspect of the present invention, the polynucleotide encoding the BMSNKC__0020/0021 polypeptide, or any fragment or complement thereof, as described herein can be used for therapeutic purposes. For instance, antisense to a polynucleotide encoding the BMSNKC_0020/0021 polypeptide, can be used in situations in which it would be desirable to block the transcription of BMSNKC_0020/0021 mRNA. In particular, cells can be transformed, transfected, or injected with sequences complementary to polynucleotides encoding the BMSNKC_0020/0021 polypeptide. Thus, complementary molecules can be used to modulate BMSNKC_0020/0021 polynucleotide and polypeptide activity, or to achieve regulation of gene function. Such technology is well known in the art, and sense or antisense oligomers or oligonucleotides, or larger fragments, can be designed from various locations along the coding or control regions of the BMSNKC_0020/0021 polynucleotide sequences encoding the novel BMSNKC_0020/0021 polypeptide.

Polypeptides used in treatment can also be generated endogenously in the subject, in treatment modalities often referred to as "gene therapy". Thus for example, cells from a subject can be engineered with a polynucleotide, such as DNA or RNA, to encode a polypeptide ex vivo, for example, by the use of a retroviral plasmid vector. The cells can then be introduced into the subject's body in which the desired polypeptide is expressed.

Transforming a cell or tissue with an expression vector that expresses high levels of a BMSNKC_0020/0021 polypeptide-encoding polynucleotide, or a fragment thereof can turn off a gene encoding the BMSNKC_0020/0021 polypeptide. Such constructs can also be used to introduce untranslatable sense or antisense sequences into a cell. Even in the absence of integration into the DNA, such vectors can continue to transcribe RNA molecules until they are disabled by endogenous nucleases. Transient expression can last for a month or more with a non-replicating vector, and even longer if appropriate replication elements are designed to be part of the vector system.

Modifications of gene expression can be obtained by designing antisense molecules or complementary nucleic acid sequences (DNA, RNA, or PNA), to the control, 5', or regulatory regions of the BMSNKC_0020/0021 polynucleotide sequence encoding the BMSNKC_0020/0021 polypeptide, (e.g., a signal sequence, promoters, enhancers, and introns). Oligonucleotides can be derived from the transcription initiation site, for example, between positions −10 and +10 from the start site.

Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (see, for example, J. E. Gee et al., 1994, In: B. E. Huber and B. I. Carr, *Molecular and Immunologic Approaches*, Futura Publishing Co., Mt. Kisco, N.Y.). The antisense molecule or complementary sequence can also be designed to block translation of mRNA by preventing the transcript from binding to ribosomes.

Many methods for introducing vectors into cells or tissues are available and are equally suitable for use in vivo, in vitro, and ex vivo. For ex vivo therapy, vectors can be introduced into stem cells or bone marrow cells obtained from the patient and clonally propagated for autologous transplant back into that same patient. Delivery by transfection, direct injection (e.g., microparticle bombardment) and by liposome injections can be achieved using methods which are well known in the art.

Any of the therapeutic methods described above can be applied to any individual in need of such therapy, including, for example, mammals such as dogs, cats, cows, horses, rabbits, monkeys, and most preferably, humans.

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Administration

A further embodiment of the present invention embraces the administration of a pharmaceutical composition, in conjunction with a pharmaceutically acceptable carrier, diluent, or excipient, to achieve any of the above-described therapeutic uses and effects. Such pharmaceutical compositions can comprise BMSNKC_0020/0021 nucleic acid, polypeptide, or peptides, antibodies to BMSNKC_0020/0021 polypeptide, mimetics, and BMSNKC_0020/0021 modulators, such as agonists, antagonists, or inhibitors of a BMSNKC_0020/0021 polypeptide or polynucleotide. The compositions can be administered alone, or in combination with at least one other agent or reagent, such as a stabilizing compound, which can be administered in any sterile, biocompatible pharmaceutical carrier, including, but not limited to, saline, buffered saline, dextrose, and water. The compositions can be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (e.g., BMSNKC__0020/0021 nucleic acid or polypeptide, or functional fragments thereof, or a BMSNKC__0020/0021 agonist or antagonist), the pharmaceutical compositions can contain pharmaceutically acceptable/physiologically suitable carriers or excipients comprising auxiliaries which facilitate processing of the active compounds into preparations that can be used pharmaceutically. Further details on techniques for formulation and administration are provided in the latest edition of *Remington's Pharmaceutical Sciences* (Mack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

In addition, pharmaceutical preparations for oral use can be obtained by the combination of active compounds with a solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents can be added, such as cross-linked polyvinyl pyrrolidone, agar, alginic acid, or a physiologically acceptable salt thereof, such as sodium alginate.

Dragee cores can be used in conjunction with physiologically suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification, or to characterize the quantity of active compound, i.e., dosage.

Pharmaceutical preparations, which can be used orally, further include push-fit capsules made of gelatin, as well as soft, scaled capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances, which increase the viscosity of the suspension, such as sodium carboxymethyl cellulose, sorbitol, or dextran. In addition, suspensions of the active compounds can be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension can also contain suitable stabilizers or agents which increase the solubility of the compounds to allow for the preparation of highly concentrated solutions.

For topical or nasal administration, penetrants or permeation agents (enhancers) that are appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes.

A pharmaceutical composition can be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, a preferred preparation can be a lyophilized powder which can contain any or all of the following: 1-50 mM histidine, 0.1%-2% sucrose, and 2-7% mannitol, at a pH range of 4.5 to 5.5, combined with a buffer prior to use. After the pharmaceutical compositions have been prepared, they can be placed in an appropriate container and labeled for treatment of an indicated condition. For administration of a BMSNKC__0020/0021 product, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, for example, using neoplastic cells, or in animal models, usually mice, rabbits, dogs, pigs, or non-human primates. The animal model can also be used to determine the appropriate concentration range and route of administration. Such information can then be used and extrapolated to determine useful doses and routes for administration in humans.

A therapeutically effective dose refers to that amount of active ingredient, for example, BMSNKC__0020/0021 polynucleotide, BMSNKC__0020/0021 polypeptide, or fragments thereof, antibodies to BMSNKC__0020/0021 polypeptide, agonists, antagonists or inhibitors of BMSNKC__0020/0021 polypeptide, which ameliorates, reduces, diminishes, or eliminates the symptoms or condition. Therapeutic efficacy and toxicity can be determined by standard pharmaceutical procedures in cell cultures or in experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the $ED_{50}$ with little or no toxicity. The dosage varies within this range depending upon the dosage form employed, the sensitivity of the patient, and the route of administration.

The practitioner, who will consider the factors related to an individual requiring treatment, can determine the exact dosage. Dosage and administration are adjusted to provide sufficient levels of the active component, or to maintain the desired effect. Factors which can be taken into account include the severity of the individual's disease state; the general health of the patient; the age, weight, and gender of the patient; diet; time and frequency of administration; drug combination(s); reaction sensitivities; and tolerance/response to therapy. As a general guide, long-acting pharmaceutical compositions can be administered every 3 to 4 days, every week, or once every two weeks, depending on half-life and clearance rate of the particular formulation. Variations in these dosage levels can be adjusted using standard empirical routines for optimization, as is well understood in the art.

As a guide, normal dosage amounts can vary from 0.1 to 100,000 micrograms (μg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors or activators. Similarly, the delivery of polynucleotides or polypeptides will be specific to particular cells, conditions, locations, and the like.

Microarrays and Screening Assays

In another embodiment of the present invention, oligonucleotides, or longer fragments derived from the BMSNKC_0020/0021 polynucleotide sequence described herein can be used as targets in a microarray. The microarray can be used to monitor the expression levels of large numbers of genes simultaneously (to produce a transcript image), and to identify genetic variants, mutations and polymorphisms. This information can be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology*, 14:1675-1680; and M. Schena et al., 1996, *Proc. Natl. Acad. Sci. USA*, 93:10614-10619). Microarrays are further described in U.S. Pat. No. 6,015,702 to P. Lal et al.

In another embodiment of this invention, a nucleic acid sequence which encodes the novel protein kinase polypeptide, can also be used to generate hybridization probes, which are useful for mapping the naturally occurring genomic sequence. The sequences can be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.*, 7:127-134 and by B. J. Trask, 1991, *Trends Genet.*, 7:149-154.

In another embodiment of the present invention, the protein kinase polypeptide of this invention, its catalytic or immunogenic fragments, or oligopeptides thereof, can be used for screening libraries of compounds in any of a variety of drug screening techniques. The BMSKNKC-0020 polypeptide, or portion thereof, employed in such screening can be free in solution, affixed to a solid support, borne on a cell surface, or located intracellularly. The formation of binding complexes between the BMSNKC_0020/0021 polypeptide, or a portion thereof, and the agent being tested can be measured utilizing techniques commonly practiced in the art, and as discussed above.

Another technique for drug screening, which can be employed, provides for high throughput screening of compounds having suitable binding affinity to the protein of interest as described in WO 84/03564 (Venton, et al.). In this method, as applied to the BMSNKC_0020/0021 protein, large numbers of different small test compounds are synthesized on a solid substrate, such as plastic pins or some other surface. The test compounds are reacted with the BMSNKC_0020/0021 polypeptide, or fragments thereof, and washed. Bound BMSNKC_0020/0021 polypeptide or its fragments is then detected by methods well known in the art. Purified BMSNKC_0020/0021 polypeptide or its fragments can also be coated directly onto plates for use in the aforementioned drug screening techniques. Alternatively, non-neutralizing antibodies can be used to capture the peptide and immobilize it on a solid support.

The use of cDNAs encoding kinases in drug discovery programs is well known as are assays capable of testing thousands of unknown compounds per day in high-throughput screens (HTSs). HTS-binding assays for drug discovery using radiolabelled ligands are described in the art (Williams et al. *Medicinal Research Reviews* 11:147-184, 1991; Sweetnam et al., *J. Natural Products* 56:441-455, 1993). Recombinant receptors can be preferred for HTS binding assays because they allow for better specificity or higher relative purity, provide the ability to generate large amounts of receptor material, and can be used in a broad variety of formats (Hodgson. *BioTechnology* 10:973-980, 1992).

In a further embodiment, competitive drug screening assays can be used in which neutralizing antibodies, capable of binding the BMSNKC_0020/0021 polypeptide according to this invention, specifically compete with a test compound, e.g., peptide, for binding to the BMSNKC_0020/0021 polypeptide. In this manner, the antibodies can be used to detect the presence of any compound, e.g., peptide, that shares one or more antigenic determinants with the BMSNKC_0020/0021 polypeptide. Radiolabeled competitive binding studies are described in Lin, et al. Antimicrobial Agents and Chemotherapy 41:2127-2131, 1997.

The human BMSNKC_0020/0021 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a BMSNKC_0020/0021 polypeptide, or a bindable peptide fragment, of this invention, comprising providing a plurality of compounds, combining the BMSNKC_0020/0021 polypeptide, or a bindable peptide fragment, with each of a plurality of compounds for a time sufficient to allow binding under suitable conditions and detecting binding of the BMSNKC_0020/0021 polypeptide or peptide to each of the plurality of test compounds, thereby identifying the compounds that specifically bind to the BMSNKC_0020/0021 polypeptide or peptide.

Methods of identifying compounds that modulate the activity of the novel human BMSNKC_0020/0021 polypeptides and/or peptides are provided by the present invention and comprise combining a potential or candidate compound or drug modulator of serine-threonine protein kinase biological activity with an BMSNKC_0020/0021 polypeptide or peptide, for example, the BMSNKC_0020/0021 amino acid sequence as set forth in SEQ ID NO:2, and measuring an effect of the candidate compound or drug modulator on the biological activity of the BMSNKC_0020/0021 polypeptide or peptide. Such measurable effects include, for example, physical binding interaction; the ability to cleave a suitable serine-threonine protein kinase substrate; effects on native and cloned BMSNKC_0020/0021-expressing cell line; and effects of modulators or other serine-threonine protein kinase-mediated physiological measures.

Another method of identifying compounds that modulate the biological activity of the novel BMSNKC_0020/0021 polypeptides of the present invention comprises combining a potential or candidate compound or drug modulator of a serine-threonine protein kinase biological activity with a host cell that expresses the BMSNKC_0020/0021 polypeptide and measuring an effect of the candidate compound or drug modulator on the biological activity of the BMSNKC_0020/0021 polypeptide. The host cell can also be capable of being induced to express the BMSNKC_0020/0021 polypeptide, e.g., via inducible expression. Physiological effects of a given modulator candidate on the BMSNKC_0020/0021 polypeptide can also be measured. Thus, cellular assays for particular serine-threonine protein kinase modulators may be either direct measurement or quantification of the physical biological activity of the BMSNKC_0020/0021 polypeptide, or they may be measurement or quantification of a physiological effect. Such methods preferably employ a BMSNKC_0020/0021 polypeptide as described herein, or an overexpressed recombinant BMSNKC_0020/0021 polypeptide in suitable host cells containing an expression vector as described herein, wherein the BMSNKC_0020/0021 polypeptide is expressed, overexpressed, or undergoes upregulated expression.

Another aspect of the present invention embraces a method of screening for a compound that is capable of modulating the biological activity of a BMSNKC_0020/0021 polypeptide, comprising providing a host cell containing an expression vector harboring a nucleic acid sequence encoding a BMSNKC_0020/0021 polypeptide, or a functional peptide or portion thereof (e.g., SEQ ID NOS: 2); determining the biological activity of the expressed BMSNKC_0020/0021 polypeptide in the absence of a modulator compound; contacting the cell with the modulator compound and determining the biological activity of the expressed BMSNKC_0020/0021 polypeptide in the presence of the modulator compound. In such a method, a difference between the activity of the BMSNKC_0020/0021 polypeptide in the presence of the modulator compound and in the absence of the modulator compound indicates a modulating effect of the compound.

Essentially any chemical compound can be employed as a potential modulator or ligand in the assays according to the present invention. Compounds tested as serine-threonine protein kinase modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel BMSNKC_0020/0021 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.,* 37:487-493; and Houghton et al., 1991, *Nature,* 354:84-88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA,* 90:6909-6913), vinylogous polypeptides (Hagihara et al., 1992, *J. Amer. Chem. Soc.,* 114:6568), nonpeptidal peptidomimetics with glucose scaffolding (Hirschmann et al., 1992, *J. Amer. Chem. Soc.,* 114:9217-9218), analogous organic synthesis of small compound libraries (Chen et al., 1994, *J. Amer. Chem. Soc.,* 116:2661), oligocarbamates (Cho et al., 1993, *Science,* 261: 1303), and/or peptidyl phosphonates (Campbell et al., 1994, *J. Org. Chem.,* 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology,* 14(3):309-314) and PCT/US96/10287), carbohydrate libraries (e.g., Liang et al., 1996, *Science,* 274:1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a BMSNKC_0020/0021 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, PA.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a BMSNKC_0020/0021 polypeptide or peptide to measure a biological binding or ligand binding activity, the source may be a whole cell lysate that can be prepared by successive freeze-thaw cycles (e.g., one to three) in the presence of standard protease inhibitors. The BMSNKC_0020/0021 polypeptide may be partially or completely purified by standard protein purification methods, e.g., affinity chromatography using specific antibody described infra, or by ligands specific for an epitope tag engineered into the recombinant BMSNKC_0020/0021 polypeptide molecule, also as described herein. Binding activity can then be measured as described.

Compounds which are identified according to the methods provided herein, and which modulate or regulate the biological activity or physiology of the BMSNKC_0020/0021 polypeptides according to the present invention are a preferred embodiment of this invention. It is contemplated that such modulatory compounds may be employed in treatment and therapeutic methods for treating a condition that is mediated by the novel BMSNKC_0020/0021 polypeptides by administering to an individual in need of such treatment a therapeutically effective amount of the compound identified by the methods described herein.

In addition, the present invention provides methods for treating an individual in need of such treatment for a disease, disorder, or condition that is mediated by the BMSNKC_0020/0021 polypeptides of the invention, comprising administering to the individual a therapeutically effective amount of the BMSNKC_0020/0021-modulating compound identified by a method provided herein.

EXAMPLES

The Examples herein are meant to exemplify the various aspects of carrying out the invention and are not intended to limit the scope of the invention in any way. The Examples do not include detailed descriptions for conventional methods employed, such as in the construction of vectors, the insertion of cDNA into such vectors, or the introduction of the resulting vectors into the appropriate host. Such methods are well known to those skilled in the art and are described in numerous publications, for example, Sambrook, Fritsch, and Maniatis, *Molecular Cloning: A Laboratory Manual*, $2^{nd}$ Edition, Cold Spring Harbor Laboratory Press, USA, (1989).

Example 1

Bioinformatics Analysis and Characterization of the BMSNKC_0020/0021 Protein Kinase Currently, one approach used for identifying and characterizing the genes distributed in the human genome includes utilizing large fragments of genomic DNA which are isolated, cloned, and sequenced. Potential open reading frames in these genomic sequences were identified using bioinformatics software.

The human protein kinase of the invention was identified from a public database via sequence similarity searching and phylogenetic analysis. The human BMSNKC_0020/0021 molecule was a protein kinase identified as a serine/threonine kinase (STK); its sequence is shown in SEQ ID NO:1. In particular, BMSNKC_0020/0021 was identified as a novel human kinase by parsimony-based phylogenetic comparison to the COT-1 kinase (Acc. No.: AF070066), where COT-1 is a serine/threonine protein kinase from the fungi *Neurospora crassa*. The phylogenetic relationship of the human protein kinase of the invention to other kinases was found by the use of Phylogenetic Analysis Using Parsimony (PAUP; Sinaur Associates; Reading, Mass.) and MacClade (Sinaur Associates, Reading Mass.). The sequence was identified through the use of a bioinformatics strategy. The complete sequence of this kinase is presented here, together with its classification and determined protein structure.

The genomic structure of BMSNKC_0020/0021 was determined by alignment to a known mouse citron kinase 310805 (P1_310805). The alignment of BMSNKC_0020/0021 to the mouse citron kinase 310805 (P1_310805) as determined by the GenewiseDB algorithm of Birney et al. was determined. The three nucleotides within a codon are oriented vertically beneath the corresponding amino acid. Post alignment scores resulted in 597.74 bits over the entire alignment. This score will be different from pre-alignment scores.

The deduced amino acid sequence of BMSNKC_0020/0021 was scanned for motifs from the Prosite database (Falquet L, Pagni M, Bucher P, Hulo N, Sigrist C J, Hofmann K, Bairoch A. The PROSITE database; *Nucleic Acids Res.* Jan. 1, 2002;30(1):235-8) using the GCG Motifs program (Accelrys; San Diego, Calif.) with no mismatches allowed. The BMSKNC_0020 human protein kinase of the invention was found to contain a protein kinase C (PKC) phosphorylation site according to the GCG Motifs algorithm having the following conserved domains: (S,T)×(R,K), specifically comprising QELQP SAK DFEVR (SEQ ID NO:12); AAKMN SNK MVNAK (SEQ ID NO:13); and FAEGT SAR TFNNI (SEQ ID NO:14). In addition, BMSNKC_0020/0021 was found to contain an ATP protein kinase motif (ATP) motif: (L,I,V,) G (P) G (P) (F,Y,W,M,G,S,T,N,H) (S,G,A) (P,W) (L,I,V,C,A,T) (P,D)×(G,S,T,A,C,L,I,V,M,F,Y)×5, 8 (L,I,V,M,F,Y,W,C,S,T,A,R) (A,I,V,P) (L,I,V,M,F,A,G,C,K,R). In particular, the human protein kinase of the present invention contains the following ATP protein kinase sequence motif: EVRSL VGCGHFAEVQVVREKATGDIYAMK VMKKK (SEQ ID NO:15).

The BMSNKC_0020/0021 human protein kinase of the invention was also found to contain a serine-threonine kinase motif: (L, I, V,M,F,Y,C)×(H,Y)×D (L,I,V,M,F,Y) K×2N (L,I,V,M,F,Y,C,T) 3(Y)×(H)×D(I)K×2N(L,I,V)3. More specifically, the human protein kinase of the present invention has the following serine-threonine kinase motif: VHLMG YVHRDIKPENILV DRTGH (SEQ ID NO: 16), and a cAMP phosphorylation site motif: (R,K)2×(S,T). In particular, the BMSNKC_0020/0021 protein kinase has the following specific motif: VSNFV RKYS DTIAE (SEQ ID NO:17).

BMSNKC_0020/0021 of this invention also contains a casein kinase II phosphorylation site, having a motif of: (S,T)×2 (D,E). More specifically, the BMSNKC_0020/0021 protein kinase has the following specific motives: RKYSD TIAE LQELQ (SEQ ID NO:18); QELQP SAKD FEVRS (SEQ ID NO:19); and AQEQV SHE EERNI (SEQ ID NO:20).

Another sequence motif contained within the BMSNKC_0020/0021 protein kinase is a myristylation domain. In particular, the conserved myristylation sequence has the following motif sequence: G(E,D,R,K,H,P,F,Y,W)×2 (S,T,A,G,C,N), and more specifically, the BMSNKC_0020/0021 protein kinase has the following myristylation sequence motif: PLSRE GILDAL FVLFE (SEQ ID NO:21).

FIG. 2 shows the regions of local identity (89.9%) and similarity (93.1%) between the BMSNKC_0020/0021 human protein kinase amino acid sequence (SEQ ID NO:2) and the mouse citron kinase 310805 sequence (SEQ ID NO:3) over 2056 amino acids with 1 gap, as determined by the GCG Gap implementation of the Needleman and Wunsch global alignment algorithm, with a gap weight of 8, a length weight of 2 and no penalties for end gaps. The results allow the determination of the novel human protein kinase polypeptide of this invention as being highly similar to the citron kinase, CitK. Based upon this finding, it is expected that the novel human protein kinase polypeptide can share at least some biological activity with other protein kinases, in addition to specific members known in the art, or as otherwise described herein.

The bioinformatics sequence information was used for full-length cloning and expression profiling. Primer sequences were obtained using the primer3 program (Steve Rozen, Helen J. Skaletsky (1996,1997) Primer3. The single exon primers as presented in Table 2 were used in the cloning process and the primers designed for two adjacent exons as presented in Table 3.

TABLE 2

Single Exon Primers for BMSNKC_0020/0021

| Template | Prod Size | Start, Length | Tm | Sequence | SEQ ID NO: |
|---|---|---|---|---|---|
| AC004815 Exon 1 Set 1 | 92 | L 4,20 | 56 | TGAAGTTCAAATATGGAGCG | 22 |
| | | R 95,21 | 59 | CTGGAAGAACAGATTCAGCCT | 23 |
| AC004813 Exon 1 Set 2 | 91 | L 4,20 | 56 | TGAAGTTCAAATATGGAGCG | 24 |
| | | R 94,20 | 57 | TGGAAGAACAGATTCAGCCT | 25 |
| AC004813 Exon 2 Set 1 | 109 | L 26,20 | 59 | GCAGATGTCTCCTCTTTCCC | 26 |
| | | R 134,20 | 59 | GACAAAGTTGCTCACGTGCT | 27 |
| AC004813 Exon 2 set 2 | 107 | L 28,20 | 59 | AGATGTCTCCTCTTTCCCGA | 28 |
| | | R 134,20 | 59 | GACAAAGTTGCTCACGTGCT | 29 |
| AC004813 Exon 3 Set 1 | 103 | L 19,20 | 59 | GTTACAGGAGCTCCAGCCTT | 30 |
| | | R 121,20 | 59 | CCCGGTTGCTTTCTCTCTTA | 31 |
| AC004813 Exon 3 Set 2 | 102 | L 20,20 | 60 | TTACAGGAGCTCCAGCCTTC | 32 |
| | | R 121,20 | 59 | CCCGGTTGCTTTCTCTCTTA | 33 |
| AC004813 Exon 5 Set 1 | 135 | L 1,20 | 59 | TCATGGAATATCAGCCTGGA | 34 |
| | | R 135,20 | 59 | CGTATCCCATCAGATGAACG | 35 |
| AC004818 Exon 5 Set 2 | 141 | L 1,20 | 59 | TCATGGAATATCAGCCTGGA | 36 |
| | | R 141,20 | 59 | GATGCACGTATCCCATCAGA | 37 |

TABLE 3

Multiple Exon Primers for BMSNKC_0020/0021

| Template | Prod Size | Start, Length | Tm | Sequence | SEQ ID NO: |
|---|---|---|---|---|---|
| AC004813 Exons 1-2 Set 1 | 124 | L 70,20 | 60 | CCTCCAGGCTCAATCTGTTC | 38 |
| | | R 213, 20 | 59 | GGCTGACTGCATTCTTCAAA | 39 |
| AC004813 Exons 1-2 Set 2 | 161 | L 70,20 | 60 | CCTCCAGGCTGAATCTGTTC | 40 |
| | | R 250, 20 | 59 | GACAAAGTTGCTCACGTGCT | 41 |
| AC004813 Exons 2-3 Set 1 | 154 | L 78,20 | 59 | TTTGAAGAATGCAGTCAGCC | 42 |
| | | R 251,20 | 59 | CAGCAAAGTGACCACAACCT | 43 |
| AC004813 Exons 2-3 Set2 | 206 | L 26,20 | 59 | GCAGATGTCTCCTCTTTCCC | 44 |
| | | R 251, 20 | 59 | CAGCAAAGTGACCACAACCT | 45 |
| AC004813 Exons 3-4 Set1 | 136 | L 70,20 | 59 | AGGTTGTGGTCACTTTGCTG | 46 |
| | | R 225, 20 | 58 | TATGTTCCGCTCTTCCTCAA | 48 |
| AC004813 Exons 3-4 Set2 | 104 | L 102,20 | 59 | TAAGAGAGAAAGCAACCGGG | 49 |
| | | R 225, 20 | 58 | TATGTTCCGCTCTTCCTCAA | 50 |

TABLE 3-continued

Multiple Exon Primers for BMSNKC_0020/0021

| Template | Prod Size | Start, Length | Tm | Sequence | SEQ ID NO: |
|---|---|---|---|---|---|
| AC004813 Exons 4-5 Set 1 | 113 | L 10,20 R 142, 20 | 58 59 | TTGAGGAAGAGCGGAACATA TCCAGGCTGATATTCCATGA | 51 52 |
| AC004813 Exons 4-5 Set 2 | 115 | L 10,20 R 144,20 | 58 59 | TTGAGGAAGAGCGGAACATA CCTCCAGGCTGATATTCCAT | 53 54 |
| AC004813 Exons 5-6 Set 1 | 98 | L 105,20 R 222, 20 | 59 59 | GCTGTTCACAGCGTTCATCT AAATCCACCAGCTTGATGTG | 55 56 |
| AC004813 Exons 5-6 Set 2 | 87 | L 116,20 R 222,20 | 59 59 | CGTTCATCTGATGGGATACG AAATCCACCAGCTTGATGTG | 56 57 |

Example 2

Cloning of the BMSNKC_0020/0021 Human Protein Kinase

EST and cDNA Clones for BMSNKC-0020

Partial transcript sequences for BMSNKC_0020/0021 identified by BLASTN searches of the Incyte LifeSeq Templates (assembled EST and cDNA sequences) found a match having greater than or equal to 95% nucleotide sequence identity over at least 50 nucleotides. The rho/rac-interacting citron kinase short isoform from *Mus musculus* (AAC72822.1; g3599507) having an Incyte Id: 188568.6 was found to match. The query length of 957 nucleotides from 1-957 was matched with the subject length spanning the nucleotides of 54-1010.

Using the EST sequence, an antisense oligonucleotide with biotin on the 5' end complementary to the presumed coding region of BMSNKC_0020/0021 was designed. This biotinylated oligo was incubated with a mixture of single-stranded covalently closed circular cDNA libraries, which contain DNA corresponding to the sense strand. Hybrids between the biotinylated oligo and the circular cDNA are captured on streptavidin magnetic beads. Upon thermal release of the cDNA from the biotinylated oligo, the single stranded cDNA is converted into double strands using a primer homologous to a sequence on the cDNA cloning vector. The double stranded cDNA is introduced into *E. coli* by electroporation and the resulting colonies are screened by PCR, using a primer pair designed from the EST sequence to identify the proper cDNA. Oligos used to identify the cDNA of the BMSNKC_0020/0021 gene of this invention by PCR can be selected from the BMSNKC_0020/0021 sequence as represented in SEQ ID NO:1 and the primers of Table 2-4.

Example 3

Multiplex Cloning

Construction of Size Fractionated cDNA Libraries

PolyA+0 RNA was purchased from Clontech, and was treated with DNase I to remove traces of genomic DNA contamination, and then converted into double stranded cDNA using the SUPERSCRIPT™ Plasmid System for cDNA Synthesis and Plasmid Cloning (Life Technologies). No radioisotope was incorporated in either of the cDNA synthesis steps. The cDNA was then size fractionated on a TransGenomics HPLC system equipped with a size exclusion column (TosoHass) with dimensions of 7.8 mm×30 cm and a particle size of 10 µm. Tris buffered saline (TBS) was used as the mobile phase, and the column was run at a flow rate of 0.5 mL/min. The system was calibrated by running a 1 kb ladder through the column and analyzing the fractions by agarose gel electrophoresis. Using these data, the fractions that are to be pooled to obtain the largest cDNA library can be determined. Generally, fractions that eluted in the range of 12 to 15 minutes were used.

The cDNA was precipitated, concentrated and then ligated into the SalI/NotI sites in pSPORT. After electroporation into *E. coli* DH12S, colonies were subjected to a miniprep procedure and the resulting cDNA was digested using SalI/NotI restriction enzymes. Generally, the average insert size of libraries made in this fashion was greater the 3.5 Kb; the overall complexity of the library was optimally greater than $10^7$ independent clones. The library was amplified in semi-solid agar for 2 days at 30° C. An aliquot (200 microliters) of the amplified library was inoculated into a 200 mL culture for single-stranded DNA isolation by superinfection with an f1 helper phage. The single stranded circular DNA was concentrated by ethanol precipitation, resuspended at a concentration of one microgram per microliter and used for the cDNA capture experiments.

Conversion of Double-Stranded cDNA Libraries into Single-Stranded Circular Form

To prepare cultures, 200 mL LB with 400 µL carbenicillin (100 mg/mL stock solution) was inoculated with from 200 µL to 1 mL of thawed cDNA library and incubated at 37° C. while shaking at 250 rpm for approximately 45 minutes, or until an $OD_{600}$ of 0.025-0.040 was attained. M13K07 helper phage (1 mL) was added to the culture and grown for 2 hours, after which Kanamycin (500 µl; 30 mg/mL) was added and the culture was grown for an additional 15-18 hours.

The culture was then poured into 6 screw-cap tubes (50 mL autoclaved tubes) and the cells were subjected to centrifugation at 10K in an HB-6 rotor for 15 minutes at 4° C. to pellet the cells. The supernatant was filtered through a 0.2 µm filter and 12,000 units of Gibco DNase I was added. The mixture was incubated for 90 minutes at room temperature.

For PEG precipitation, 50 mL of ice-cold 40% PEG 8000, 2.5 M NaCl, and 10 mM $MgSO_4$ were added to the supernatant, mixed, and aliquotted into 6 centrifuge tubes (covered with parafilm). The tubes and contents were incubated for 1 hour on wet ice or at 4° C. overnight. The tubes were then centrifuged at 10K in a HB-6 rotor for 20 minutes at 4° C. to pellet the helper phage.

Following centrifugation, the supernatant was discarded and the sides of the tubes were dried. Each pellet was resuspended in 1 mL TE, pH 8. The resuspended pellets were pooled into a 14 mL tube (Sarstedt; Newton, N.C.), (6 mL total). SDS was added to 0.1% (60 µl of stock 10% SDS). Freshly made proteinase K (20 mg/mL) was added (60 µl) and the suspension was incubated for 1 hour at 42° C.

For phenol/chloroform extractions, 1 mL of NaCl (5M) was added to the suspension in the tube. An equal volume of phenol/chloroform (7 mL total volume) was added and the contents were vortexed or shaken. The suspension was then centrifuged at 5K in an HB-6 rotor for 5 minutes at 4° C. The aqueous (top) phase was transferred to a new tube (Sarstedt) and extractions were repeated until no interface was visible.

Ethanol precipitation was then performed on the aqueous phase, which was then divided into 2 tubes (3 mL each). To each tube, 2 volumes of 100% ethanol were added and precipitation was carried out overnight at −20° C. The precipitated DNA was pelleted at 10K in an HB-6 rotor for 20 minutes at 4° C. The ethanol was discarded. Each pellet was resuspended in 700 μl of 70% ethanol. The contents of each tube were combined into one micro centrifuge tube and centrifuged in a micro centrifuge (Eppendorf) at 14K for 10 minutes at 4° C. After discarding the ethanol, the DNA pellet was dried in a speed vacuum. In order to remove oligosaccharides, the pellet was resuspended in 50 μl TE buffer, pH 8. The resuspension was incubated on dry ice for 10 minutes and centrifuged at 14K in an Eppendorf microfuge for 15 minutes at 4° C. The supernatant was then transferred to a new tube and the final volume was recorded.

To check purity, DNA was diluted 1:100 and added to a micro quartz cuvette, where DNA was analyzed by spectrometry at an $OD_{260}/OD_{280}$. The preferred purity ratio was between 1.7 and 2.0. The DNA was diluted to 1 μg/μL in TE, pH 8 and stored at 4° C. The concentration of DNA was calculated using the formula: (32 μg/mL*OD)(mL/1000 μL)(100)($OD_{260}$). The quality of single-stranded DNA was determined by first mixing 1 μL of 5 ng/μl ssDNA; 11 μl deionized water; 1.5 μL 10 μM T7 sport primer (fresh dilution of stock); 1.5 μl 10× Precision-Taq buffer per reaction. In the repair mix, a cocktail of 4 μl of 5 mM dNTPs (1.25 mM each); 1.5 μL 10× Precision-Taq buffer; 9.25 μL deionized water; and 0.25 μL Precision-Taq polymerase was mixed per reaction and preheated at 70° C. until the middle of the thermal cycle.

The DNA mixes were aliquotted into PCR tubes and the thermal cycle was started. The PCR thermal cycle consisted of 1 cycle at 95° C. for 20 sec.; 59° C. for 1 min. (15 μL repair mix added); and 73° C. for 23 minutes. For ethanol precipitation, 15 μg glycogen, 16 μl ammonium acetate (7.5M), and 125 μL 100% ethanol were added and the contents were centrifuged at 14K in an Eppendorf microfuge for 30 minutes at 4° C. The resulting pellet was washed 1 time with 125 μL 70% ethanol and then the ethanol was discarded. The pellet was dried in a speed vacuum and resuspended in 10 μL TE buffer, pH 8.

Single-stranded DNA was electroporated into *E. coli* DH10B or DH12S cells by pre-chilling the cuvettes and sliding holder and thawing the cells on ice-water. DNA was aliquotted into micro centrifuge tubes (Eppendorf) as follows: 2 μL repaired library, (=1×10$^{-3}$ μg); 1 μL unrepaired library (1 ng/μL), (=1×10$^{-3}$ μg); and 1 μL pUC19 positive control DNA (0.01 μg/μL), (=1×10$^{-5}$ μg). The mixtures were stored on ice until use.

One at a time, 40 μL of cells were added to a DNA aliquot. The cell/DNA mixture was not pipetted up and down more than one time. The mixture was then transferred via pipette into a cuvette between the metal plates and electroporation was performed at 1.8 kV. Immediately afterward, 1 mL SOC medium (i.e., SOB (bacto-tryptone; bacto-yeast extract; NaCl)+glucose (20 mM)+Mg$^{2+}$) (See, J. Sambrook et al., *Molecular Cloning: A Laboratory Manual*, 2nd Ed., A.2, 1989) was added to the cuvette and the contents were transferred 15 mL media as commonly known in the art. The cells were allowed to recover for 1 hour at 37° C. with shaking (225 rpm).

Serial dilutions of the culture were made in 1:10 increments (20 μL into 180 μL LB) for plating the electroporated cells. For the repaired library, dilutions of 1:100, 1:1000, 1:10,000 were made. For the unrepaired library, dilutions of 1:10 and 1:100 were made. Positive control dilutions of 1:10 and 1:100 were made. Each dilution (100 μL) was plated onto small plates containing LB+carbenicillin and incubated at 37° C. overnight. The titer and background were calculated by methods well known in the art. Specifically, the colonies on each plate were counted using the lowest dilution countable. The titer was calculated using the formula: (# of colonies)(dilution factor)(200 μL/100 μL)(1000 μL/20 μL)=CFUs, where CFUs/μg DNA used=CFU/μg. The % background=((unrepaired CFU/μg)/(repaired CFU/μg))×100%.

Solution Hybridization and DNA Capture

One microliter of anti-sense biotinylated oligonucleotides (or sense oligonucleotides when annealing to single-stranded DNA from pSPORT2 vector) containing 150 ng of up to 50 different 80-mer oligonucleotide probes was added to 6 μL (6 μg) of a mixture of up to 15 single-stranded, covalently-closed, circular brain and testis cDNA libraries and 7 μL of 100% formamide in a 0.5 mL PCR tube. The sequence of the 80-mer oligonucleotide used is as follows:

5'-b-TGTCCCCGGTTGCTTTCTCTCTTACCACCTG (SEQ ID NO:58)

CACTTCAGCAAAGTGACCACAACCTACAAGACTTCT

GACTTCGAAGTCC-3'; "b" is biotin;

Anti-sense capture oligos for BMSNKC_0020/0021 that are based on the AC004813 template for use in the cDNA capture experiments are as follows:

5'-TGATATTCCATGACCAGATAAAGGTGATTTTTG (SEQ ID NO:59)

TCCTGAAAGGCATACTGTAATTGGGGATCCACGGG

CTTGTGCTTCG-3'

The mixture was heated in a thermal cycler to 95° C. for 2 minutes. Fourteen microliters of 2× hybridization buffer (50% formamide, 1.5 M NaCl, 0.04 M NaPO$_4$, pH 7.2, 5 mM EDTA, 0.2% SDS) were added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 minutes, and mixed every 5 minutes to resuspend the beads. The beads were separated from the solution with a magnet and washed three times in 200 microliters of 0.1×SSPE, 0.1% SDS at 45° C.

The single stranded cDNAs was released from the biotinylated oligo/streptavidin magnetic bead complex by adding 50 microliters of 0.1 N NaOH and incubating at room temperature for 10 minutes. Six microliters of 3 M sodium acetate was added along with 15 μg of glycogen and the solution was ethanol precipitated with 120 microliters of 100% ethanol. The precipitated DNA was resuspended in 12 μL of TE (10 mM Tris-HCl, pH 8.0, 1 mM EDTA, pH 8.0). The single stranded cDNA was converted into double strands in a thermal cycler by mixing 5 μL of the captured DNA with 1.5 μL of 10 μM of standard SP6 primer for libraries in pSPORT 1 and 2, and T7 primer for libraries in pCMVSPORT, and 1.5 μL of 10×PCR buffer. Sequences of primers used to repair single-stranded circular DNA isolated from the primary selection, are as follows:

```
T7Sport   5'-TAATACGACTCACTATAGGG-3' (SEQ ID NO:60)

SP6Sport  5'-ATTTAGGTGACACTATAG-3'  (SEQ ID NO:61)
```

The mixture was heated to 95° C. for 20 seconds, and then ramped down to 59° C. At this time 15 μL of a repair mix, preheated to 70° C., was added to the DNA (Repair mix contains 4 μL of 5 mM dNTPs (1.25 mM each), 1.5 μL of 10×PCR buffer, 9.25 μL of water, and 0.25 μL of Taq polymerase). The solution was ramped back to 73° C. and incubated for 23 minutes.

The repaired DNA was ethanol precipitated and resuspended in 10 μL of TE. Two μL were electroporated per tube containing 40 μL of *E. coli* DH12S cells. Three hundred and thirty three microliters were plated onto one 150 mm plate of LB agar plus 100 μg/mL of ampicillin. After overnight incubation at 37° C., the colonies from all plates were harvested by scraping into 10 mL of LB+50 μg/mL of ampicillin and 2 mL of sterile glycerol.

The second round of selection was initiated by making single-strand circular DNA from the primary selected library using the above-described method. The purified single-stranded circular DNA was then assayed with gene-specific primers for each of the targeted sequences using standard PCR conditions.

The sequences of the Gene-Specific Primer (GSP) pairs used to identify the various targeted cDNAs in the primary selected single-stranded cDNA libraries are as follows:

```
Sense      5'-GCAGATGTCTCCTCTTTCCC-3' (SEQ ID NO:62)
Primer 1

Antisense  5'-GACAAAGTTGCTCACGTGCT-3' (SEQ ID NO:63)
Primer 1
```

The secondary hybridization was performed including only those 80-mer biotinylated probes whose targeted sequences had a positive result with the GSPs. The resulting single-stranded circular DNA was converted into double strands using the antisense oligo for each target sequence as the repair primer (the sense primer was used for material captured from pSPORT2 libraries). The resulting double stranded DNA was electroporated into DH10B cells and the resulting colonies were inoculated into 96 deep well blocks. After overnight growth, DNA was prepared and sequentially screened for each of the targeted sequences using the GSPs. The DNA was also digested with SalI and NotI restriction enzymes and the inserts were sized by agarose gel electrophoresis. Selected cDNAs were then chosen for DNA sequencing.

Example 4

Expression Profiling of Novel Human Citron Kinase-Related Protein Kinase

The PCR primer pairs used to measure the steady state levels of mRNA by quantitative PCR in various tissues included the following citron kinase-related protein kinase primer pairs:

| BATCH 1 | | |
|---|---|---|
| cit.tp2s | 5'-GTTACAGGAGCTCCAGCCTT-3' | (SEQ ID NO:64) |
| cit.tp2a | 5'-CCCGGTTGCTTTCTCTCTTA-3' | (SEQ ID NO:65) |

| BATCH 2 | | |
|---|---|---|
| cit.tp5s | 5'-CAGTCAGCCTGCTCTGATGA-3' | (SEQ ID NO:66) |
| cit.tp4a | 5'-TCAGCAAAGTGACCACAACC-3' | (SEQ ID NO:67) |

The primers of SEQ ID NOS: 64 and 65 were used in FIGS. 5-7 and 10-13, where the novel human citron kinase-related kinase was found to be expressed in tissues such as brain, pancreas, stomach, small intestine, and thymus. Further the primers of SEQ ID NOS: 66 and 67 were used in FIGS. 8-9. Briefly, first strand cDNA was made from commercially available mRNA (Clontech) and subjected to real time quantitative PCR using a PE 5700 instrument (Applied Biosystems, Foster City, Calif.) which detects the amount of DNA amplified during each cycle by the fluorescent output of SYBR green, a DNA binding dye specific for double strands. The specificity of the primer pair for its target was verified by performing a thermal denaturation profile at the end of the run which provided an indication of the number of different DNA sequences present by determining melting Tm. The contribution of contaminating genomic DNA to the assessment of tissue abundance was controlled for by performing the PCR with first strand made with and without reverse transcriptase. In all cases, the contribution of material amplified in the no reverse transcriptase controls was expected to be negligible.

Small variations in the amount of cDNA used in each tube were determined by performing a parallel experiment using a primer pair for the cyclophilin gene, which was expressed in equal amounts in all tissues. These data were used to normalize the data obtained with the primer pairs. The PCR data were converted into a relative assessment of the differences in transcript abundance among the tissues tested.

As indicated in FIG. 4, transcripts corresponding to the novel human protein kinase of the present invention were found to be highly expressed in adult testis, bone marrow and gastrointestinal tract. Expression is also observed in fetal tissues, namley the liver, heart, skin, stomach and brain. Expression levels may be slightly higher in lung, colon, and breast tumors.

Example 5

TAQMAN™ Quantitative PCR Analysis of CitK Methods

Total RNA from tissues was isolated using the TriZol protocol (Invitrogen) and quantified by determining absorbance at 260 nM. An assessment of the 18 s and 28 s ribosomal RNA bands was made by denaturing gel electrophoresis to determine RNA integrity.

The specific sequence to be measured was aligned with related genes found in GenBank to identify regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer or probe sequences were searched against public Genbank databases to ensure target specificity. Primers and probes were obtained from ABI.

The sequences of the CitK primer/probe set are

```
Forward Primer:
5'-GAATGCCAAACTCCCGATTG-3'           (SEQ ID NO:69)

Reverse Primer:
5'-CCATCCCCGTTCATCACAGT-3'           (SEQ ID NO:70)

Probe:
5'-CCCCAGATTACATGGCTCCTGAAGTGCT-3'   (SEQ ID NO:71)
```

DNA Contamination

To access the level of contaminating genomic DNA in the RNA, the RNA was divided into 2 aliquots and one half in treated with Rnase-free Dnase (Invitrogen). Samples from both the Dnase-treated and non-treated were then subjected to reverse transcription reactions with (RT+) and without (RT−) the presence of reverse transcriptase. TAQMAN™ assays were carried out with gene-specific primers and the contribution of genomic DNA to the signal detected was evaluated by comparing the threshold cycles obtained with the RT+/RT− non-DNAse-treated RNA to that of the RT+/RT− Dnase treated RNA. The amount of signal contributed by genomic DNA in the DNAse-treated RT− RNA had to be less that 10% of that obtained with DNAse-treated RT+RNA. If not, the RNA was not used in actual experiments.

Reverse Transcription Reaction and Sequence Detection

DNAse-treated total RNA (100 ng) was annealed to 2.5 µM of the gene-specific reverse primer in the presence of 5.5 mM Magnesium Chloride by heating the sample to 72° C. for 2 min and then cooling to 55° C. for 30 min. MuLv reverse transcriptase (1.25 U/µl) and 500 µM of each dNTP was added to the reaction and the tube was incubated at 37° C. for 30 min. The sample was then heated to 90° C. for 5 min to denature enzyme.

Quantitative sequence detection was carried out on a ABI PRISM 7700 by adding to the reverse transcribed reaction 2.5 µM forward and reverse primers, 500 µM of each dNTP, buffer, and 5U AMPLITAQ GOLD™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$.

Figure 14:
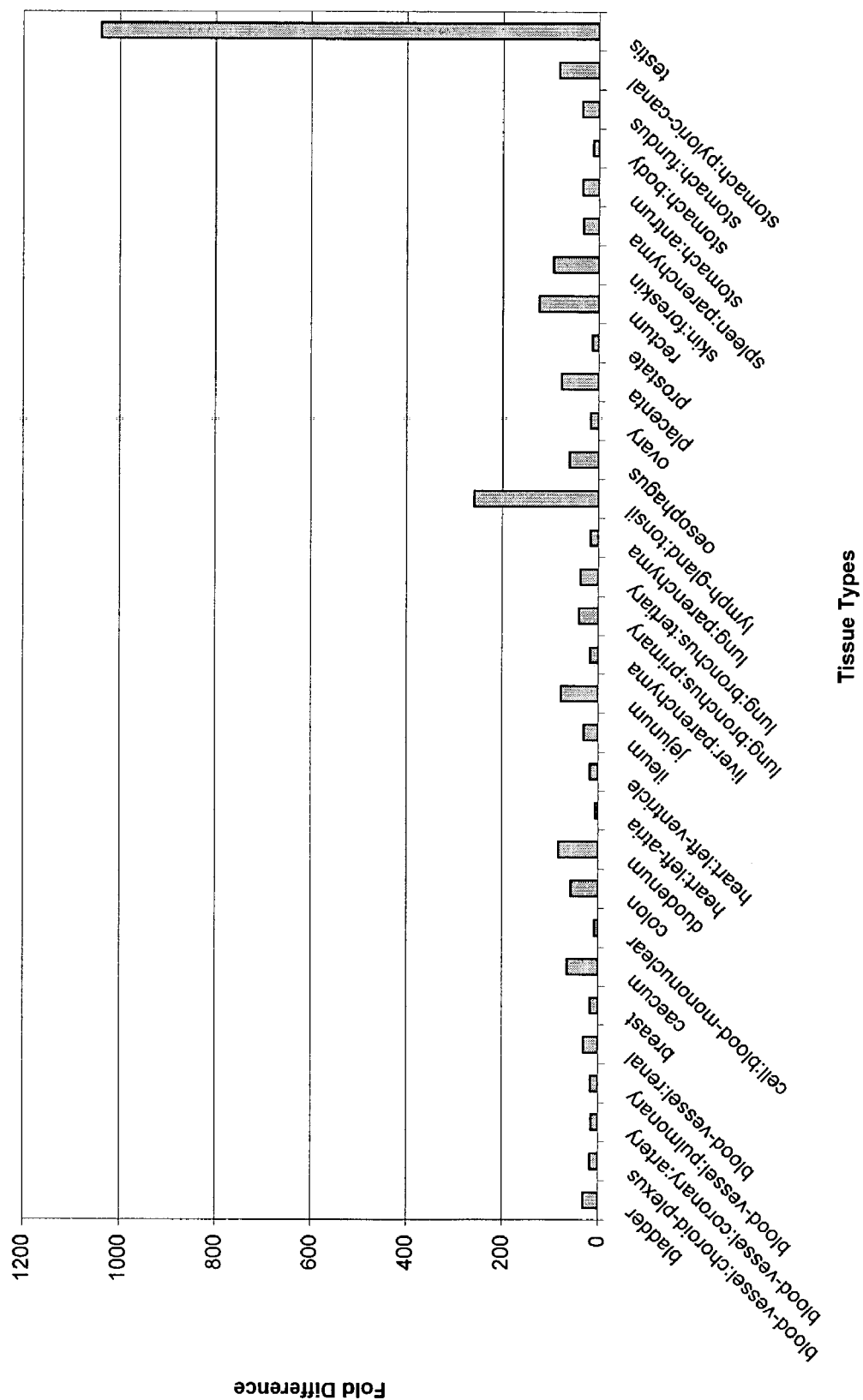
FIG. 14 shows the results of the SYBR green quantitative PCR analysis of CitK in human adult tissue RNAs.

SYBR green quantitative PCR analysis of CitK in human adult tissue RNAs demonstrated that transcripts for this novel kinase were found primarily in the testis and the bone marrow (FIG. 14). Analysis of CitK by TAQMAN™ quantitative PCR on an extended panel of tissue RNAs confirmed and extended these observations. As shown in FIG. 14, CitK is expressed approximately 1,000 fold higher in the testis than most other tissues tested. CitK transcripts were also detected in the lymph gland and throughout the gastrointestinal tract. As observed in the SYBR green experiments, CitK expression is essentially absent in the adult nervous system.

Figure 15:
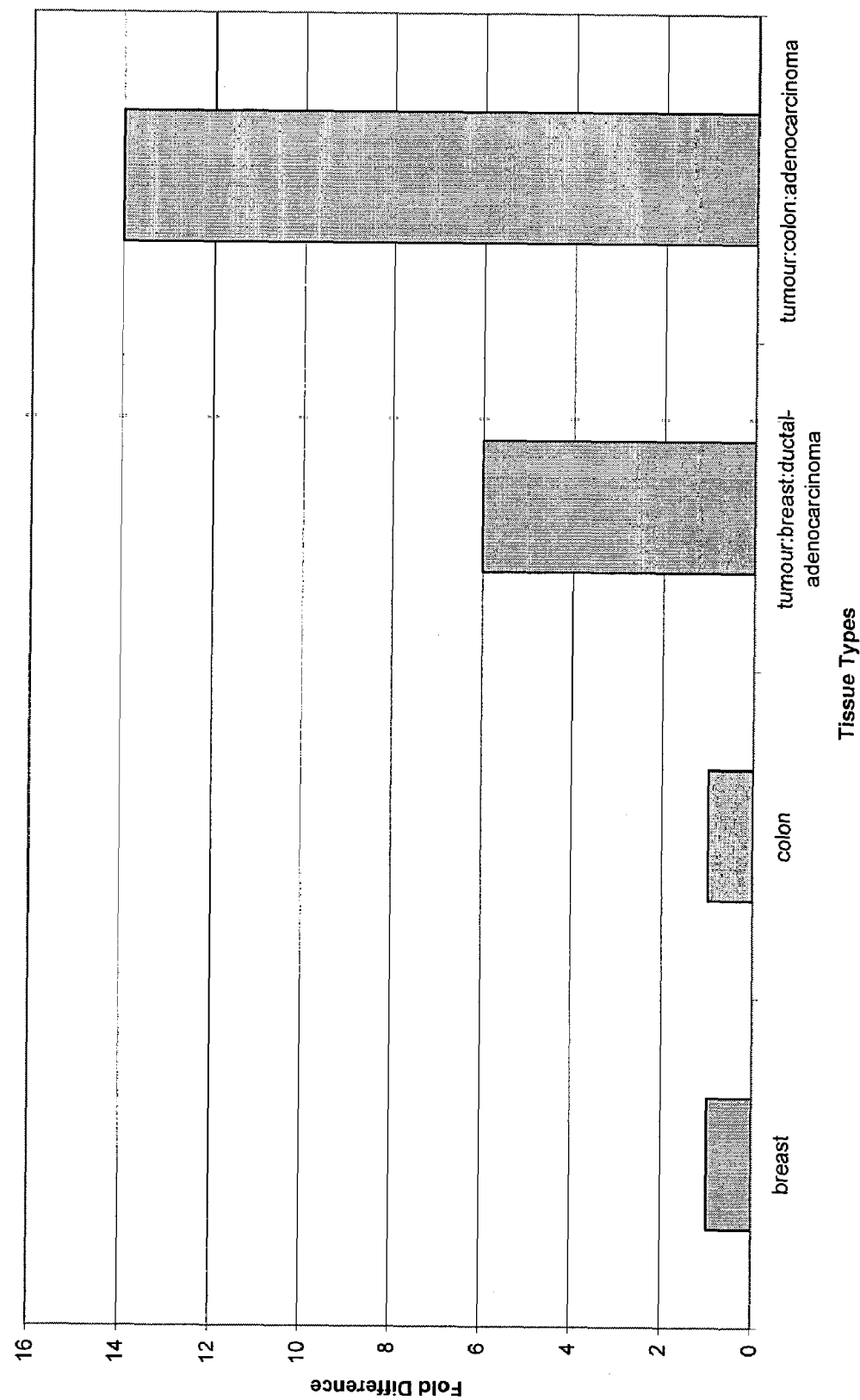
FIG. 15 shows the results of the SYBR green quantitative PCR analysis of CitK in particular human tumor types.

The SYBR green quantitative PCR analysis of CitK in certain human tumor types also suggested increased CitK expression. An analysis of CitK by TAQMAN™ quantitative PCR on a panel of normal and tumor RNAs confirmed these observation (FIG. 15). The results indicated that the steady state level of CitK transcripts is approximately 6 fold higher in ductal-adenocarcinoma than in normal breast tissue and is approximately 14 fold higher in colon adencocarincoma than in matched controls.

These data suggest a CitK association in the etiology of certain types of breast and colon cancers.

Figure 16:
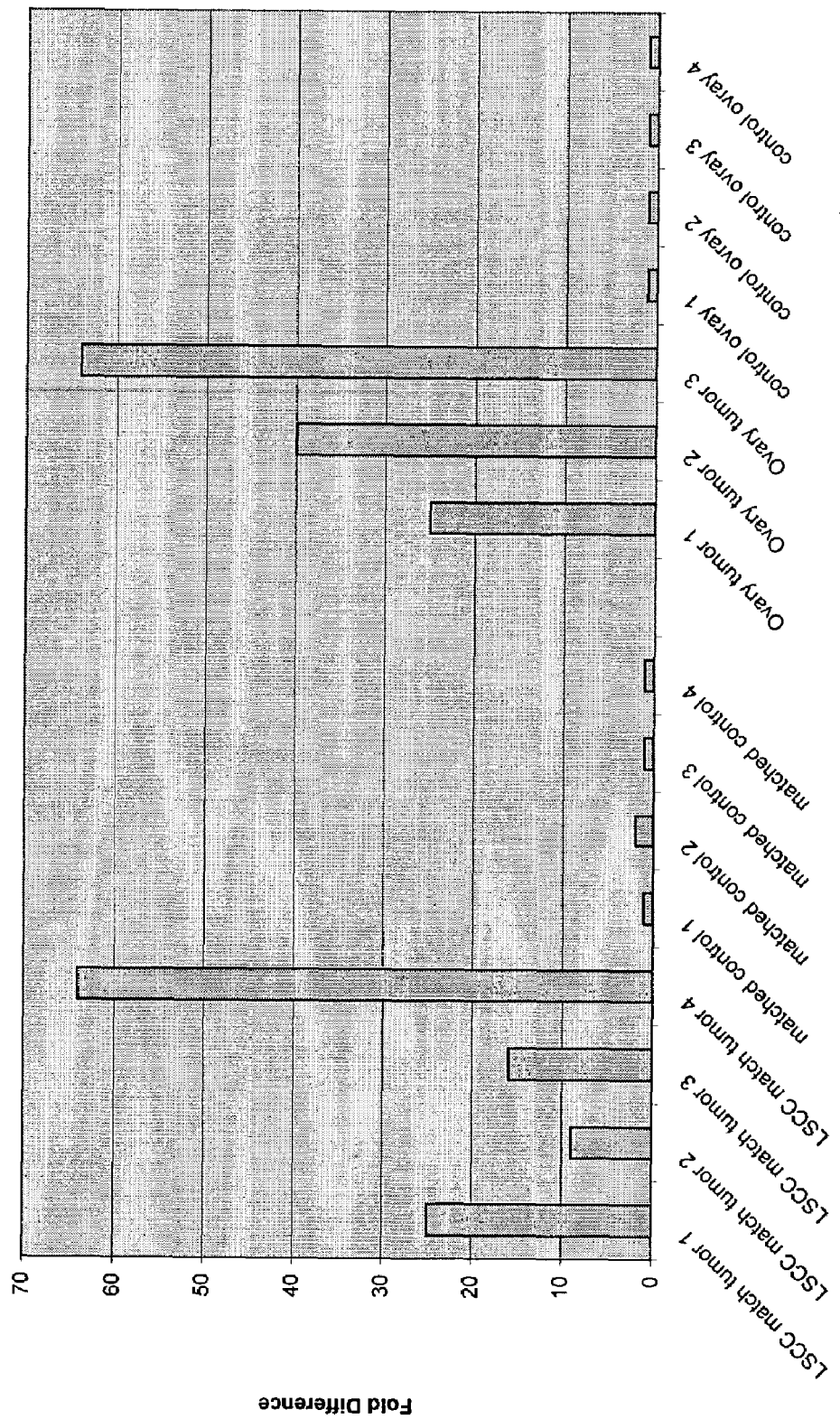
FIG. 16 shows an expanded expression profile of the novel serine/threonine kinase, BMSNKC_0020/0021, of the present invention. The figure illustrates the relative expression level of BMSNKC_0020/0021 amongst various mRNA tissue sources isolated from normal and tumor tissues. As shown, the BMSNKC_0020/0021 polypeptide was differentially expressed in lung-squamous cell carcinoma tumors, and ovarian cancer tissue compared to each respective normal tissue. Expression data was obtained by measuring the steady state BMSNKC_0020/0021 mRNA levels by quantitative PCR using the PCR primer pair provided as SEQ ID NO:69 and 70, and TAQMAN™ probe (SEQ ID NO:71) as described in Example 5 herein.

An additional expression profile is also provided in FIG. 16. The results indicate the steady state level of CitK transcripts were differentially expressed in lung-squamous cell carcinoma tumors compared to control lung tissue with ranges of overexpression from 9 fold to 65 fold over normal tissue. In addition, the results indicate that CitK was differentially expressed in ovarian tumors relative to normal tissue with levels of overexpression ranging from 25 and 65 fold higher in the tumor tissue.

Example 6

Signal Transduction Assays

The activity of the BMSNKC_0020/0021 protein kinase or homologue thereof, can be measured using any assay suitable for the measurement of the activity of a protein kinase, as commonly known in the art. The signal transduction activity of a protein kinase can be determined by monitoring intracellular $Ca^{2+}$, cAMP, inositol-1,4,5-triphosphate ($IP_3$), or 1,2-diacylglycerol (DAG). Assays for the measurement of intracellular $Ca^{2+}$ are described, for example, in Sakurai et al. (EP 480 381). Intracellular $IP_3$ can be measured using a kit available from Amersham, Inc. (Arlington Heights, Ill.). A kit for measuring intracellular cAMP is available from Diagnostic Products, Inc. (Los Angeles, Calif.).

Activation of a protein kinase triggers the release of $Ca^{2+}$ ions sequestered in the mitochondria, endoplasmic reticulum, and other cytoplasmic vesicles into the cytoplasm. Fluorescent dyes, e.g., fura-2, can be used to measure the concentration of free cytoplasmic $Ca^{2+}$. The ester of fura-2, which is lipophilic and can diffuse across the cell membrane, is added to the culture medium of the host cells which recombinantly express BMSNKC_0020/0021. Once inside the cell, the fura-2 ester is hydrolyzed by cytosolic esterases to its non-lipophilic form, and then the dye cannot diffuse out of the cell. The non-lipophilic form of fura-2 fluoresces when it binds to free $Ca^{2+}$. The fluorescence can be measured without lysing the cells at an excitation spectrum of 340 nm or 380 nm and at fluorescence spectrum of 500 nm (Sakurai et al., EP 480 381).

Upon activation of BMSNKC_0020/0021, the rise of free cytosolic $Ca^{2+}$ concentration is preceded by the hydrolysis of phosphatidylinositol 4,5-bisphosphate. Hydrolysis of this phospholipid by the phospholipase, phospholipase C, yields 1,2-diacylglycerol (DAG), which remains in the membrane, and water-soluble inositol 1,4,5-triphosphate ($IP_3$). Binding of ligands or agonists will increase the concentration of DAG and $IP_3$. Thus, signal transduction activity can be measured by monitoring the concentration of these hydrolysis products.

To measure $IP_3$ concentration, radioactively-labeled ([$^3$H])-inositol is added to the culture medium of host cells expressing the BMSNKC_0020/0021 protein kinase. The $^3$H-inositol is taken up by the cells and incorporated into $IP_3$. The resulting inositol triphosphate is separated from the mono- and di-phosphate forms and measured (Sakurai et al., EP 480 381). Alternatively, an inositol 1,4,5-triphosphate assay system (Amersham) is commercially available for such use. With this system, the supplier (Amersham) provides tritium-labeled inositol 1,4,5-triphosphate and a receptor capable of distinguishing the radioactive inositol from other inositol phosphates. With these reagents, an effective and accurate competition assay can be performed to determine the inositol triphosphate levels.

Cyclic AMP levels can be measured according to the methods described in Gilman et al., *Proc. Natl. Acad. Sci.*, 67:305-312 (1970). In addition, a kit for assaying levels of cAMP is available from Diagnostic Products Corp. (Los Angeles, Calif.).

Example 7

Method of Creating N- and C-Terminal Deletion Mutants Corresponding to the BMSNKC_0020/0021 Polypeptide of the Present Invention.

As described elsewhere herein, the present invention encompasses the creation of N- and C-terminal deletion mutants, in addition to any combination of N- and C-terminal deletions thereof, corresponding to the BMSNKC_0020/0021 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length BMSNKC_0020/0021 polypeptide sequence (as described herein, for example), appropriate primers of about 15-25 nucleotides derived from the desired 5' and 3' positions of SEQ ID NO:1 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the D96 to Q319 N-terminal deletion mutant, the following primers could be used to amplify a cDNA fragment corresponding to this deletion mutant:

Representative PCR amplification conditions are provided below, although the skilled artisan would appreciate that other conditions may be required for efficient amplification. A 100 ul PCR reaction mixture may be prepared using 10 ng of the template DNA (cDNA clone of BMSNKC_0020/0021), 200 uM 4 dNTPs, 1 uM primers, 0.25U Taq DNA polymerase (PE), and standard Taq DNA polymerase buffer. Typical PCR cycling condition are as follows:

| 20-25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E. coli* cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the BMSNKC_0020/0021 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))−25), wherein 'S' is equal to the nucleotide position of the

```
5' Primer 5'-GCAGCA GCGGCCGC GACTTCGAAGTCAGAAGTCTTGTAG-3'   (SEQ ID NO:74)
                   NotI
3' Primer 5'-GCAGCA GTCGAC CTGGAAATTCATAATGTTATTGAAG-3'     (SEQ ID NO:75)
                   SalI
```

For example, in the case of the M1 to I315 C-terminal deletion mutant, the following primers could be used to amplify a cDNA fragment corresponding to this deletion mutant:

initiating start codon of the BMSNKC_0020/0021 gene (SEQ ID NO:1), and 'X' is equal to the most C-terminal amino acid of the intended N-terminal deletion mutant. The first term will provide the start 5' nucleotide position of the

```
5' Primer 5'-GCAGCA GCGGCCGC ATGTTGAAGTTCAAATATGGAGCGC-3'   (SEQ ID NO:76)
                   NotI 3' Primer 5'-GCAGCA GTCGAC AATGTTATTGAAGGTTCTGGCAGAG-3'     (SEQ ID NO:77)
                   SalI
```

3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 8

Method of Assessing the Ability of BMSNKC_0020/0021 to Phosphorylate a Kinase Substrate A number of methods may be employed to assess the level of serine/threonine kinase activity of the BMSNKC_0020/0021 of the present invention. One preferred method is described below. Phosphorylation studies may be applied to the BMSNKC_0020/0021 polypeptide. Such studies can be carried out with in host cells stably or transient expressing the BMSNKC_0020/0021 nucleotide as described herein. As described in Papst et al. (J. Biol. Chem., 273: 15077-15084, 1998; which is hereby incorporated by reference herein in its entirety), COS cells stably expressing BMSNKC_0020/0021 nucleotide are grown in phosphate-free medium containing 10% fetal bovine serum and 150 [mu]Ci/ml of [P]orthophosphate. After a 3 hour incubation, the radiolabeled cells are lysed in lysis buffer (25 mM Tris-HCl (pH 7.4), 50 mM NaCl, 0.5% sodium deoxycholate, 2% Nonidet P-40, 0.2% SDS, 1 [mu]M PMSF, 50 [mu]g/ml aprotinin, 50 [mu]M leupeptin). The lysates are immunoprecipitated with either a mouse phosphoserine or mouse phosphothreonine monoclonal antibody (Calbiochem, San Diego, Calif.). The immunoprecipitates are separated on a 7.5% SDS-polyacrylamide gel and the radiolabeled proteins are visualized by autoradiography.

If BMSNKC_0020/0021 polypeptide exhibits ser/thr kinase activity, those cells overexpressing BMSNKC_0020/0021 polypeptide will have elevated levels of phosphorylated proteins as compared to untransfected COS cells. Immunoprecipitation with antibodies specific for phosphoserine or phosphothreonine will demonstrate that BMSNKC_0020/0021 polypeptide phosphorylates serine and threonine residues.

An aspect of the invention involves assays to identify modulators of BMSNKC_0020/0021 kinase activity. It will be apparent that any kinase activity assay, such as the assay described above, can be adapted to screen for inhibitors, e.g., by comparing the kinase activity of BMSNKC_0020/0021 in the presence of a test compound to activity in the absence, to determine if the test compound increases or decreases kinase activity.

Additional studies may be employed, for example, to further assess the kinase activity of the BMSNKC_0020/0021 polypeptide, and in particular, to assess the substrate specificity of BMSNKC_0020/0021. Such studies may utilize the methods described by Songyang, Z., et al, or modifications thereof (Mol. Cell. Biol., 16:6486-6493 (1996); which is hereby incorporated by reference herein in its entirety).

One skilled in the art could easily modify the exemplified studies to test the activity of polynucleotides of the invention, agonists, and/or antagonists of polynucleotides or polypeptides of the invention.

Example 9

Protein Fusions of the BMSNKC_0020/0021 Polypeptide

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc Region:

(SEQ ID NO:73)
GGGATCCGGAGCCCAAATCTTCTGACAAAACTCACACATGCCCACC

GTGCCCAGCACCTGAATTCGAGGGTGCACCGTCAGTCTTCCTCTTCCCCC

CAAAACCCAAGGACACCCTCATGATCTCCCGGACTCCTGAGGTCACATGC

GTGGTGGTGGACGTAAGCCACGAAGACCCTGAGGTCAAGTTCAACTGGTA

CGTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

```
-continued
CCCAACCCCCATCGAGAAAACCATCTCCAAAGCCAAAGGGCAGCCCCGAG

AACCACAGGTGTACACCCTGCCCCCATCCCGGGATGAGCTGACCAAGAAC

CAGGTCAGCCTGACCTGCCTGGTCAAAGGCTTCTATCCAAGCGACATCGC

CGTGGAGTGGGAGAGCAATGGGCAGCCGGAGAACAACTACAAGACCACGC

CTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTC

CGGGTAAATGAGTGCGACGGCCGCGACTCTAGAGGAT
```

The contents of all patents, patent applications, published PCT applications and articles, books, references, reference manuals, abstracts and internet websites cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An isolated nucleic acid molecule consisting of nucleotides 1 to 957 of SEQ ID NO:1.

2. An isolated nucleic acid molecule consisting of nucleotides 4 to 957 of SEQ ID NO:1.

3. An isolated nucleic acid molecule consisting of nucleotides 286 to 957 of SEQ ID NO:1.

4. An isolated nucleic acid molecule consisting of the nucleic acid molecule of claim 1, 2, or 3 fused to a heterologous nucleic acid sequence, wherein said heterologous nucleic acid sequence encodes the Fc domain of immunoglobulin, and wherein said Fc domain encoding nucleic acid is the sequence provided as SEQ ID NO:73.

5. An isolated nucleic acid molecule consisting of the complete complementary sequence of the isolated nucleic acid molecule of claim 1, 2, or 3.

* * * * *